United States Patent
Anderson et al.

(10) Patent No.: US 10,144,733 B2
(45) Date of Patent: *Dec. 4, 2018

(54) NAPHTHYRIDINE DERIVATIVES AS ALPHA V BETA 6 INTEGRIN ANTAGONISTS FOR THE TREATMENT OF E.G. FIBROTIC DISEASES

(71) Applicant: GlaxoSmithKline Intellectual Property Development Limited, Brentford, Middlesex (GB)

(72) Inventors: Niall Andrew Anderson, Stevenage (GB); Ian Baxter Campbell, Stevenage (GB); Matthew Howard James Campbell-Crawford, Stevenage (GB); Ashley Paul Hancock, Stevenage (GB); Seble Lemma, Stevenage (GB); Simon John Fawcett MacDonald, Stevenage (GB); John Martin Pritchard, Stevenage (GB); Panayiotis Alexandrou Procopiou, Stevenage (GB)

(73) Assignee: GlaxoSmithKline Intellectual Property Development Limited, Brentford, Middlesex (GB)

( * ) Notice: Subject to any disclaimer, the term of this patent is extended or adjusted under 35 U.S.C. 154(b) by 0 days.

This patent is subject to a terminal disclaimer.

(21) Appl. No.: 15/514,416

(22) PCT Filed: Sep. 22, 2015

(86) PCT No.: PCT/EP2015/071782
§ 371 (c)(1),
(2) Date: Mar. 24, 2017

(87) PCT Pub. No.: WO2016/046230
PCT Pub. Date: Mar. 31, 2016

(65) Prior Publication Data
US 2017/0291899 A1    Oct. 12, 2017

(30) Foreign Application Priority Data
Sep. 26, 2014  (GB) .................................. 1417094.8

(51) Int. Cl.
C07B 59/00   (2006.01)
C07D 471/04  (2006.01)

(52) U.S. Cl.
CPC .......... C07D 471/04 (2013.01); C07B 59/002 (2013.01); *C07B 2200/05* (2013.01)

(58) Field of Classification Search
CPC .................................................. C07D 471/04
USPC ....................................................... 514/300
See application file for complete search history.

(56) References Cited

U.S. PATENT DOCUMENTS

| | | | | |
|---|---|---|---|---|
| 9,956,209 B2* | 5/2018 | Anderson | ............ | C07D 471/04 |
| 10,000,489 B2* | 6/2018 | Anderson | ............ | C07D 471/04 |
| 10,004,724 B2* | 6/2018 | Anderson | .......... | A61K 31/4375 |
| 10,023,568 B2* | 7/2018 | Anderson | ............ | C07D 471/04 |
| 2004/0092454 A1 | 5/2004 | Schadt et al. | | |
| 2016/0280705 A1* | 9/2016 | Anderson | ............ | C07D 471/04 |
| 2017/0290817 A1* | 10/2017 | Anderson | .......... | A61K 31/4375 |
| 2017/0290818 A1* | 10/2017 | Anderson | .......... | A61K 31/4375 |

FOREIGN PATENT DOCUMENTS

| | | |
|---|---|---|
| WO | WO 99/30709 A1 | 6/1999 |
| WO | WO 99/31061 A1 | 6/1999 |
| WO | WO 00/72801 A2 | 12/2000 |
| WO | WO 00/78317 A1 | 12/2000 |

(Continued)

OTHER PUBLICATIONS

Hall; Biochemical Pharmacology 2016, 117, 88-96. (Year: 2016).*

(Continued)

*Primary Examiner* — Daniel R Carcanague
(74) *Attorney, Agent, or Firm* — Jane F. Djung; Kathryn A. Lutomski

(57) ABSTRACT

A compound of formula (I) or a salt thereof:

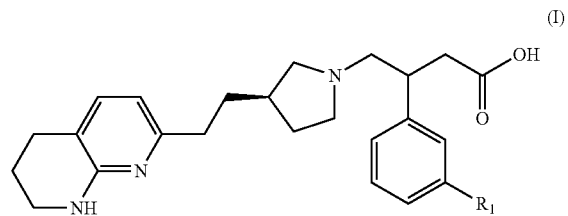

(I)

wherein $R_1$ represents a five-membered aromatic heterocycle selected from a N- or a C-linked mono- or di-substituted pyrazole, an N- or a C-linked optionally mono- or di-substituted triazole or an N- or a C-linked optionally mono- or di-substituted imidazole, which five-membered aromatic heterocycle may be substituted by one or two of the groups selected a methyl group, an ethyl group, a fluorine atom, a hydroxymethyl group, a 2-hydroxypropan-2-yl group, a trifluoromethyl group, a difluoromethyl group or a fluoromethyl group, except that when $R_1$ represents an N-linked mono- or di-substituted pyrazole, $R_1$ does not represent 3,5-Dimethyl-1H-pyrazol-1-yl, 5-Methyl-1H-pyrazol-1-yl, 5-Ethyl-3-methyl-1H-pyrazol-1-yl, 3,5-Diethyl-1H-pyrazol-1-yl, 4-Fluoro-3,5-dimethyl-1H-pyrazol-1-yl, 3-Methyl-1H-pyrazol-1-yl or 1H-pyrazol-1-yl.

13 Claims, No Drawings

(56) References Cited

FOREIGN PATENT DOCUMENTS

| | | | |
|---|---|---|---|
| WO | WO 01/24797 A1 | | 4/2001 |
| WO | WO2001024797 | * | 4/2001 |
| WO | WO 01/34602 A2 | | 5/2001 |
| WO | WO 01/096334 A2 | | 12/2001 |
| WO | WO 02/07730 A1 | | 1/2002 |
| WO | WO 02/22616 A2 | | 3/2002 |
| WO | WO 02/053099 A2 | | 7/2002 |
| WO | WO2004/058254 A1 | | 7/2004 |
| WO | WO 2004/092454 A2 | | 10/2004 |
| WO | WO 2005/082889 A1 | | 9/2005 |
| WO | WO2005082889 | * | 9/2005 |
| WO | WO 2008/118455 A1 | | 10/2008 |
| WO | WO 2009/055418 A1 | | 4/2009 |
| WO | WO 2011/111880 A1 | | 9/2011 |
| WO | WO 2014/154725 A1 | | 10/2014 |
| WO | WO2014154725 | * | 10/2014 |
| WO | WO 2015/048819 A1 | | 4/2015 |
| WO | WO 2016/046225 A1 | | 3/2016 |
| WO | WO 2016/046226 A1 | | 3/2016 |
| WO | WO 2016/046241 A1 | | 3/2016 |
| WO | WO 2016/134223 A2 | | 8/2016 |
| WO | WO 2016/145258 A1 | | 9/2016 |
| WO | WO 2017/158072 A1 | | 9/2017 |
| WO | WO 2017/162570 A1 | | 9/2017 |
| WO | WO 2017/162572 A1 | | 9/2017 |

OTHER PUBLICATIONS

Anderson; Org. Biomol. Chem. 2016, 14, 5992-6009. (Year: 2016).*
International Search Report for International Application No. PCT/EP2015/071776, dated Nov. 5, 2015 (date of completion of the international search).
International Search Report for International Application No. PCT/EP2015/071777, dated Nov. 20, 2015 (date of completion of the international search).
International Search Report for International Application No. PCT/EP2015/071798, dated Nov. 4, 2015 (date of completion of the international search).
International Search Report for International Application No. PCT/EP2015/071782, dated Oct. 21, 2015 (date of completion of the international search).
Cho, et al., "Pirfenidone: an anti-fibrotic and cytoprotective agent as therapy for progressive kidney disease", *Expert Opin. Investig. Drugs*, vol. 19, No. 2, pp. 275-283 (2010).
Goodman et al., "Integrins as therapeutic targets", *Trends in Pharmacological Sciences*, vol. 33, No. 7, pp. 405-412 (2012).
Hahm et al., "avB6 integrin Regulates Renal Fibrosis and Inflammation in Alport Mouse", *The American Journal of Pathology*, vol. 170, No. 1, pp. 110-125 (2007).

Horan et al., "Partial Inhibition of Integrin avB6 Prevents Pulmonary Fibrosis without Exacerbating Inflammation", *Am. J. Respir. Crit. Care Med.*, vol. 177, pp. 56-65 (2008).
Margadant, C. et al., "Integrin-TGF-$\beta$ crosstalk in fibrosis, cancer, and wound healing", *EMBO Reports*, vol. 11, No. 2, pp. 97-105 (2010).
Popov et al, "Integrin avB6 is a marker of the progression of biliary and portal liver fibrosis and a novel target for antifibrotic therapies", *Journal of Hepatology*, vol. 48 pp. 453-464 (2008).
Trevillian et al., "$\alpha_v\beta_6$ integrin expression in diseased and transplanted kidneys", *Kidney International*, vol. 66, pp. 1423-1433 (2004).
Whitman et al., "Nonpeptide $\alpha v\beta 3$ antagonists. Part 9: Improved pharmacokinetic profile through the use of an aliphatic, des-amide backbone", *Bioorganic & Medicinal Chemistry Letters*, vol. 14, No. 17, pp. 4411-4415 (2004).
Woodcock, et al. The treatment of idiopathic pulmonary fibrosis, *F1000Prime Report*, vol. 6, No. 16, pp. 1-9 (2014).
International Search Report for International Application No. PCT/EP2014/056013, dated May 9, 2014, 4 pages.
International Search Report for International Application No. PCT/EP2015/071776, dated Nov. 23, 2015, 4 pages.
International Search Report for International Application No. PCT/EP2015/071777, dated Nov. 26, 2015, 4 pages.
International Search Report for International Application No. PCT/EP2015/071782, dated Nov. 2, 2015, 4 pages.
International Search Report for International application No. PCT/EP2015/071798, dated Nov. 10, 2015, 4 pages.
International Search Report for International application No. PCT/EP2017/056204, dated May 15, 2017, 5 pages.
International Search Report for International application No. PCT/EP2017/056525, dated May 2, 2017, 4 pages.
International Search Report for International application No. PCT/EP2017/056527, dated May 2, 2017, 5 pages.
Restriction Requirement for U.S. Appl. No. 14/778,095, USPTO, dated Sep. 21, 2016, 9 pages.
Non-Final Office Action for U.S. Appl. No. 14/778,095, USPTO, dated Mar. 29, 2017, 14 pages.
Notice of Allowance for U.S. Appl. No. 14/778,095, USPTO, dated Nov. 3, 2017, 11 pages.
Notice of Allowance for U.S. Appl. No. 15/514,407, USPTO, dated Nov. 6, 2017, 16 pages.
Notice of Allowance for U.S. Appl. No. 15/514,414, USPTO, dated Nov. 9, 2017, 19 pages.
Notice of Allowance for U.S. Appl. No. 15/514,399, USPTO, dated Dec. 15, 2017, 13 pages.
Notice of Allowance for U.S. Appl. No. 15/514,399, USPTO, dated Aug. 21, 2017, 11 pages.

* cited by examiner

NAPHTHYRIDINE DERIVATIVES AS ALPHA V BETA 6 INTEGRIN ANTAGONISTS FOR THE TREATMENT OF E.G. FIBROTIC DISEASES

This application is a § 371 of International Application No. PCT/EP2015/071782, filed 22 Sep. 2015, which claims the priority of GB Application No. 1417094.8, filed 26 Sep. 2014, which are incorporated herein in their entireties.

FIELD OF THE INVENTION

The present invention relates to pyrrolidine compounds being $\alpha_v\beta_6$ integrin antagonists, pharmaceutical compositions comprising such compounds and to their use in therapy, especially in the treatment of conditions for which an $\alpha_v\beta_6$ integrin antagonist is indicated, for the use of a compound in the manufacture of a medicament for the treatment of conditions in which an antagonist of $\alpha_v\beta_6$ integrin is indicated and a method for the treatment or prophylaxis of disorders in which antagonism of $\alpha_v\beta_6$ integrin is indicated in a human.

BACKGROUND OF THE INVENTION

Integrin superfamily proteins are heterodimeric cell surface receptors, composed of an alpha and beta subunit. At least 18 alpha and 8 beta subunits have been reported, which have been demonstrated to form 24 distinct alpha/beta heterodimers. Each chain comprises a large extracellular domain (>640 amino acids for the beta subunit, >940 amino acids for the alpha subunit), with a transmembrane spanning region of around 20 amino acids per chain, and generally a short cytoplasmic tail of 30-50 amino acids per chain. Different integrins have been shown to participate in a plethora of cellular biologies, including cell adhesion to the extracellular matrix, cell-cell interactions, and effects on cell migration, proliferation, differentiation and survival (Barczyk et al, *Cell and Tissue Research*, 2010, 339, 269).

Integrin receptors interact with binding proteins via short protein-protein binding interfaces. The integrin family can be grouped into sub-families that share similar binding recognition motifs in such ligands. A major subfamily is the RGD-integrins, which recognise ligands that contain an RGD (arginine-glycine-aspartic acid) motif within their protein sequence. There are 8 integrins in this sub-family, namely $\alpha_v\beta_1$, $\alpha_v\beta_3$, $\alpha_v\beta_5$, $\alpha_v\beta_6$, $\alpha_v\beta_8$, $\alpha_{IIb}\beta_3$, $\alpha_5\beta_1$, $\alpha_5\beta_1$, $\alpha_8\beta_1$, where nomenclature demonstrates that $\alpha_v\beta_1$, $\alpha_v\beta_3$, $\alpha_v\beta_5$, $\alpha_v\beta_6$, & $\alpha_v\beta_6$ share a common $\alpha_v$ subunit with a divergent β subunit, and $\alpha_v\beta_1$, $\alpha_5\beta_1$ & $\alpha_8\beta_1$ share a common $\beta_1$ subunit with a divergent α subunit. The $\beta_1$ subunit has been shown to pair with 11 different α subunits, of which only the 3 listed above commonly recognise the RGD peptide motif (Humphries et al, *Journal of Cell Science*, 2006, 119, 3901).

The 8 RGD-binding integrins have different binding affinities and specificities for different RGD-containing ligands. Ligands include proteins such as fibronectin, vitronectin, osteopontin, and the latency associated peptides (LAPs) of Transforming Growth Factor $\beta_1$ and $\beta_3$ (TGFβ$_1$ and TGFβ$_3$). Integrin binding to the LAPs of TGFβ$_1$ and TGFβ$_3$ has been shown in several systems to enable activation of the TGFβ$_1$ and TGFβ$_3$ biological activities, and subsequent TGFβ-driven biologies (Worthington et al, *Trends in Biochemical Sciences*, 2011, 36, 47). The diversity of such ligands, coupled with expression patterns of RGD-binding integrins, generates multiple opportunities for disease intervention. Such diseases include fibrotic diseases (Margadant et al, EMBO reports, 2010, 11, 97), inflammatory disorders, cancer (Desgrosellier et al, *Nature Reviews Cancer*, 2010, 10, 9), restenosis, and other diseases with an angiogenic component (Weis et al, *Cold Spring. Harb. Perspect. Med.* 2011, 1, a 006478).

A significant number of $\alpha_v$ integrin antagonists (Goodman et al, *Trends in Pharmacological Sciences*, 2012, 33, 405) have been disclosed in the literature including inhibitory antibodies, peptides and small molecules. For antibodies these include the pan-$\alpha_v$ antagonists Intetumumab and Abituzumab (Gras, *Drugs of the Future*, 2015, 40, 97), the selective $\alpha_v\beta_3$ antagonist Etaracizumab, and the selective $\alpha_v\beta_6$ antagonist STX-100. Cilengitide is a cyclic peptide antagonist that inhibits both $\alpha_v\beta_3$ and $\alpha_v\beta_5$ and SB-267268 is an example of a compound (Wilkinson-Berka et al, *Invest. Ophthalmo. Vis. Sci.*, 2006, 47, 1600), that inhibits both $\alpha_v\beta_3$ and $\alpha_v\beta_5$. Invention of compounds to act as antagonists of differing combinations of $\alpha_v$ integrins enables novel agents to be generated tailored for specific disease indications.

Pulmonary fibrosis represents the end stage of several interstitial lung diseases, including the idiopathic interstitial pneumonias, and is characterised by the excessive deposition of extracellular matrix within the pulmonary interstitium. Among the idiopathic interstitial pneumonias, idiopathic pulmonary fibrosis (IPF) represents the commonest and most fatal condition with a typical survival of 3 to 5 years following diagnosis. Fibrosis in IPF is generally progressive, refractory to current pharmacological intervention and inexorably leads to respiratory failure due to obliteration of functional alveolar units. IPF affects approximately 500,000 people in the USA and Europe.

There are in vitro experimental, animal and IPF patient immunohistochemistry data to support a key role for the epithelially restricted integrin, $\alpha_v\beta_6$, in the activation of TGFβ1. Expression of this integrin is low in normal epithelial tissues and is significantly up-regulated in injured and inflamed epithelia including the activated epithelium in IPF. Targeting this integrin, therefore, reduces the theoretical possibility of interfering with wider TGF homeostatic roles. Partial inhibition of the $\alpha_v\beta_6$ integrin by antibody blockade has been shown to prevent pulmonary fibrosis without exacerbating inflammation (Horan G S et al Partial inhibition of integrin $\alpha_v\beta_6$ prevents pulmonary fibrosis without exacerbating inflammation. *Am J Respir Crit Care Med* 2008 177 56-65). Outside of pulmonary fibrosis, $\alpha_v\beta_6$ is also considered an important promoter of fibrotic disease of other organs, including liver and kidney (Reviewed in Henderson N C et al Integrin-mediated regulation of TGFβ in Fibrosis, Biochimica et Biophysica Acta—Molecular Basis of Disease 2013 1832891-896), suggesting that an $\alpha_v\beta_6$ antagonist could be effective in treating fibrotic diseases in multiple organs.

Consistent with the observation that several RGD-binding integrins can bind to, and activate, TGFβ, different $\alpha_v$ integrins have recently been implicated in fibrotic disease (Henderson N C et al Targeting of $\alpha_v$ integrin identifies a core molecular pathway that regulates fibrosis in several organs *Nature Medicine* 2013 Vol 19, Number 12: 1617-1627; Sarrazy V et al Integrins αvβ5 and αvβ3 promote latent TGF-β1 activation by human cardiac fibroblast contraction *Cardiovasc Res* 2014 102:407-417; Minagawa S et al Selective targeting of TGF-β activation to treat fibroinflammatory airway disease *Sci Transl Med* 2014 Vol 6, Issue 241: 1-14; Reed N I et al. The $\alpha_v\beta_1$ integrin plays a critical in vivo role in tissue fibrosis *Sci Transl Med* 2015 Vol 7, Issue 288: 1-8). Therefore inhibitors against specific members of the RGD binding integrin families, or with specific selectivity fingerprints within the RGD binding integrin family, may be effective in treating fibrotic diseases in multiple organs.

SAR relationships of a series of integrin antagonists against $\alpha_v\beta_3$ $\alpha_v\beta_5$, $\alpha_v\beta_6$ and $\alpha_v\beta_8$ have been described (Macdonald, S J F et al. Structure activity relationships of a, integrin antagonists for pulmonary fibrosis by variation in aryl substituents. *ACS MedChemLett* 2014, 5, 1207-1212. 19 Sep. 2014).

It is an object of the invention to provide $\alpha_v\beta_6$ antagonists, preferably with activities against other $\alpha_v$ integrins, such as $\alpha_v\beta_1$, $\alpha_v\beta_3$, $\alpha_v\beta_5$ or $\alpha_v\beta_8$.

BRIEF SUMMARY OF THE INVENTION

In a first aspect of the present invention, there is provided a compound of formula (I) or a salt thereof, more particularly a compound of formula (I) or a pharmaceutically acceptable salt thereof:

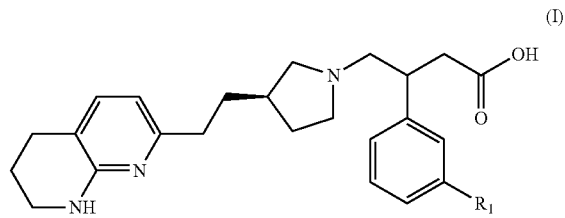

(I)

wherein $R_1$ represents a five-membered aromatic heterocycle selected from a N- or a C-linked mono- or di-substituted pyrazole, an N- or a C-linked optionally mono- or di-substituted triazole or an N- or a C-linked optionally mono- or di-substituted imidazole, which five-membered aromatic heterocycle may be substituted by one or two of the groups selected from a hydrogen atom, a methyl group, an ethyl group, a fluorine atom, a hydroxymethyl group, a 2-hydroxypropan-2-yl group, a trifluoromethyl group, a difluoromethyl group or a fluoromethyl group, except that when $R_1$ represents an N-linked mono- or di-substituted pyrazole, $R_1$ does not represent 3,5-Dimethyl-1H-pyrazol-1-yl, 5-Methyl-1/H-pyrazol-1-yl, 5-Ethyl-3-methyl-1H-pyrazol-1-yl, 3,5-Diethyl-1H-pyrazol-1-yl, 4-Fluoro-3,5-dimethyl-1H-pyrazol-1-yl, 3-Methyl-1H-pyrazol-1-yl, or 1H-pyrazol-1-yl.

Compounds of formula (I) and their salts have $\alpha_v\beta_6$ integrin antagonist activity and are believed to be of potential use for the treatment or prophylaxis of certain disorders. The term $\alpha_v\beta_6$ antagonist activity includes $\alpha_v\beta_6$ inhibitor activity herein.

In a second aspect of the present invention, there is provided a pharmaceutical composition comprising a compound of formula (I) or a pharmaceutically acceptable salt thereof and one or more pharmaceutically acceptable carriers, diluents or excipients.

In a third aspect of the present invention, there is provided a compound of formula (I), or a pharmaceutically acceptable salt thereof for use in therapy, in particular in the treatment of a disease or condition for which an $\alpha_v\beta_6$ integrin antagonist is indicated.

In a fourth aspect of the present invention, there is provided a method of treatment or prophylaxis of a disease or condition for which an $\alpha_v\beta_6$ integrin antagonist is indicated in a human in need thereof which comprises administering to a human in need thereof a therapeutically effective amount of compound of formula (I) or a pharmaceutically acceptable salt thereof.

In a fifth aspect of the present invention, there is provided the use of a compound of formula (I), or a pharmaceutically acceptable salt thereof in the manufacture of a medicament for the treatment of a disease or condition for which an $\alpha_v\beta_6$ integrin antagonist is indicated.

In a sixth aspect of the present invention, there is provided a compound of formula (XI)

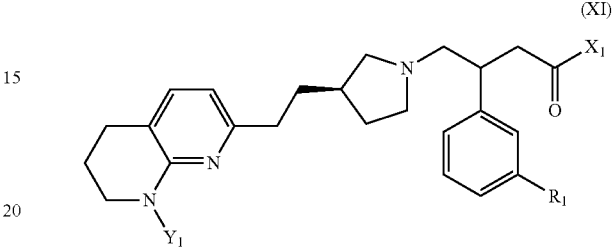

(XI)

wherein $R_1$ is as hereinbefore defined, $X_1$ represents hydroxyl or a moiety which is hydrolysable by metabolism in the human body to form the corresponding acid compound of formula (I) in which $X_1$ is —OH;

$Y_1$ represents hydrogen or a moiety which is hydrolysable by metabolism in the human body to form the corresponding amino compound of formula (I) in which $Y_1$ is hydrogen;

provided that when $X_1$ is hydroxyl, then $Y_1$ is not hydrogen.

DETAILED DESCRIPTION OF THE INVENTION

In a first aspect of the present invention, there is provided a compound of formula (I) or a salt thereof, more particularly a compound of formula (I) or a pharmaceutically acceptable salt thereof:

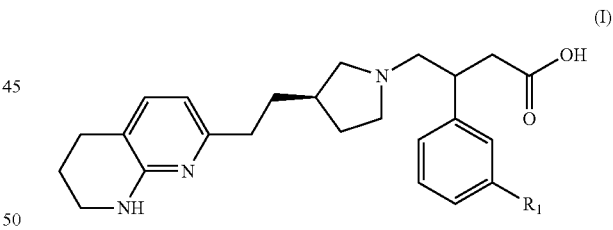

(I)

wherein $R_1$ represents a five-membered aromatic heterocycle selected from a N- or a C-linked mono- or di-substituted pyrazole, an N- or a C-linked optionally mono- or di-substituted triazole or an N- or a C-linked optionally mono- or di-substituted imidazole, which five-membered aromatic heterocycle may be substituted by one or two of the groups selected from a hydrogen atom, a methyl group, an ethyl group, a fluorine atom, a hydroxymethyl group, a 2-hydroxypropan-2-yl group, a trifluoromethyl group, a difluoromethyl group or a fluoromethyl group, except that when $R_1$ represents an N-linked mono- or di-substituted pyrazole, $R_1$ does not represent 3,5-Dimethyl-1H-pyrazol-1-yl, 5-Methyl-1H-pyrazol-1-yl, 5-Ethyl-3-methyl-1H-pyrazol-1-yl, 3,5-Diethyl-1H-pyrazol-1-yl, 4-Fluoro-3,5-dimethyl-1H-pyrazol-1-yl, 3-Methyl-1H-pyrazol-1-yl or 1H-pyrazol-1-yl.

In one embodiment there is provided a compound of formula (I) or a salt thereof, more particularly a compound of formula (I) or a pharmaceutically acceptable salt thereof:

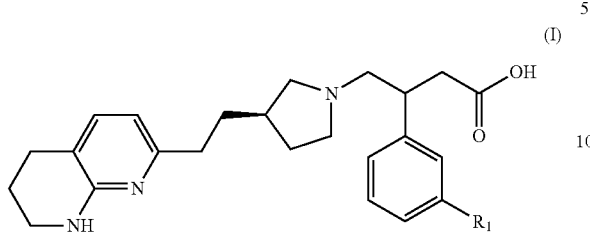

(I)

wherein R₁ represents a five-membered aromatic heterocycle selected from a N- or a C-linked mono- or di-substituted pyrazole, an N- or a C-linked optionally mono- or di-substituted triazole or an N- or a C-linked optionally mono- or di-substituted imidazole, which five-membered aromatic heterocycle may be substituted by one or two of the groups selected from a hydrogen atom, a methyl group, an ethyl group, a fluorine atom, a hydroxymethyl group, a 2-hydroxypropan-2-yl group, a trifluoromethyl group, a difluoromethyl group or a fluoromethyl group, except that when R₁ represents an N-linked mono- or di-substituted pyrazole, R₁ does not represent 3,5-Dimethyl-1H-pyrazol-1-yl, 5-Methyl-1H-pyrazol-1-yl, 5-Ethyl-3-methyl-1H-pyrazol-1-yl, 3,5-Diethyl-1H-pyrazol-1-yl, 4-Fluoro-3,5-dimethyl-1H-pyrazol-1-yl or 3-Methyl-1H-pyrazol-1-yl.

In one embodiment, R₁ is a C-linked mono- or di-substituted pyrazole.

In another embodiment, R₁ is an N-linked mono- or di-substituted pyrazole.

In another embodiment R₁ is an N- or C-linked optionally mono- or di-substituted triazole.

In another embodiment R₁ is an N- or C-linked optionally mono- or di-substituted imidazole.

In one embodiment, R₁ is a C-linked mono- or di-substituted pyrazole selected from 3-methyl-1H-pyrazol-5-yl, and 1,4-dimethyl-1H-pyrazol-5-yl, In another embodiment, R₁ is an N-linked mono- or di-substituted pyrazole selected from -(2-hydroxypropan-2-yl)-5-methyl-1H-pyrazol-1-yl, 3-(trifluoromethyl)-1H pyrazol-1-yl, 3-(hydroxymethyl)-5-methyl-1H-pyrazol-1-yl, and 3-(fluoromethyl)-5-methyl-1H-pyrazol-1-yl.

In another embodiment R₁ is an N- or C-linked optionally mono- or di-substituted triazole selected from 4H-1,2,4-triazol-4-yl, 3,5-dimethyl-1H/1,2,4-triazol-1-yl, 3-methyl-4H-1,2,4-triazol-4-yl, 1H-1,2,3-triazol-1-yl, 1H-1,2,4-triazol-1-yl;

In another embodiment R₁ is an N- or C-linked optionally mono- or di-substituted imidazole selected from 1H-imidazol-1-yl and mono- or di-methyl imidazole 1-methyl-1H-imidazol-2-yl, 4-methyl-1H-imidazol-2-yl, (1,4-dimethyl-1H-imidazol-2-yl) and (2,4-dimethyl-1H-imidazol-5-yl).

In another embodiment R₁ is an N- or C-linked optionally mono- or di-substituted imidazole selected from 1H-imidazol-1-yl and mono- or di-methyl imidazole 1-methyl-1H-imidazol-2-yl, 4-methyl-1H-imidazol-2-yl and (1,4-dimethyl-1H-imidazol-2-yl).

In another embodiment R₁ is an N- or C-linked optionally mono- or di-substituted imidazole selected from 1H-imidazol-1-yl and (1,4-dimethyl-1H-imidazol-2-yl) and (2,4-dimethyl-1H-imidazol-5-yl).

In one embodiment, R₁ is selected from the following heterocycles:

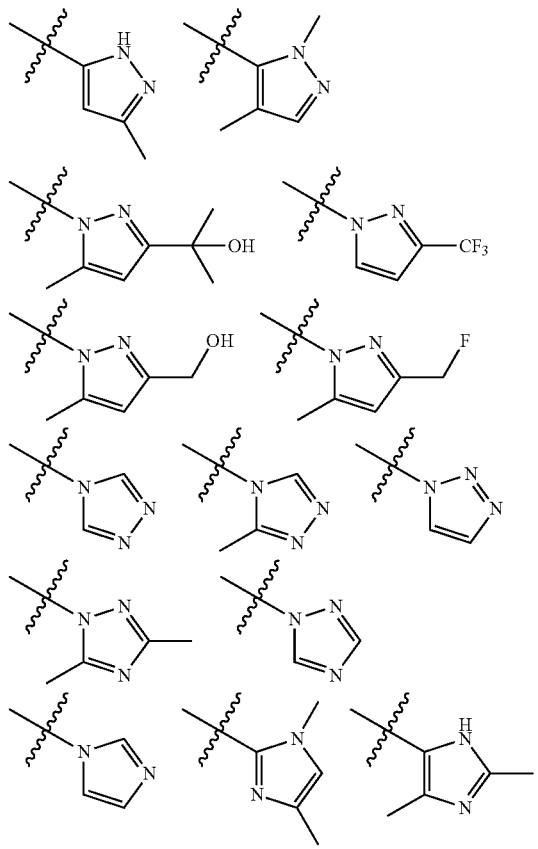

In some embodiments the compound of formula (I) or a salt thereof has the structural formula (IA):

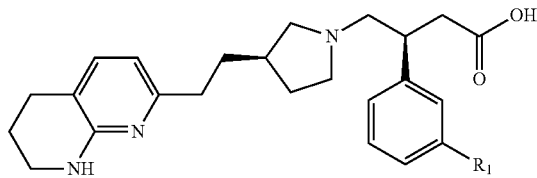

or a pharmaceutically acceptable salt thereof.

In other embodiments the compound of formula (I) or salt thereof has the structural formula (IB): R

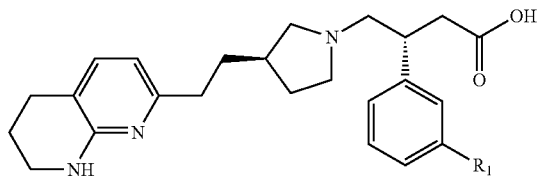

or a pharmaceutically acceptable salt thereof.

It is to be understood that the present invention covers all combinations of particular and preferred groups described hereinabove.

In some embodiments, R₁ represents a 3-methyl-1H-pyrazol-5-yl group, 1,4-dimethyl-1H-pyrazol-5-yl, 3-(2-hydroxypropan-2-yl)-5-methyl-1H-pyrazol-1-yl, 3-(trifluoromethyl)-1H-pyrazol-1-yl, 3-(hydroxymethyl)-5-methyl-1H-pyrazol-1-yl, 3-(fluoromethyl)-5-methyl-1H-pyrazol-1-yl;

In other embodiments $R_1$ is an N- or C-linked optionally mono- or di-substituted triazole selected from 4H-1,2,4-triazol-4-yl, 3,5-dimethyl-1H-1,2,4-triazol-1-yl, 3-methyl-4H-1,2,4-triazol-4-yl, 1H-1,2,3-triazol-1-yl and 1H-1,2,4-triazol-1-yl;

In other embodiments $R_1$ is an N- or C-linked optionally mono- or di-substituted imidazole selected from 1H-imidazol-1-yl and mono- or di-methyl imidazole, 1-methyl-1H-imidazol-2-yl, 4-methyl-1H-imidazol-2-yl, particularly 1H-imidazol-1-yl and (1,4-dimethyl-1H-imidazol-2-yl) and (2,4-dimethyl-1H-imidazol-5-yl).

In some embodiments, $R_1$ represents a 3-methyl-1H-pyrazol-5-yl group

In some embodiments, $R_1$ represents a 1,4-dimethyl-1H-pyrazol-5-yl group,

In some embodiments, $R_1$ represents a 3-(2-hydroxypropan-2-yl)-5-methyl-1H-pyrazol-1-yl group.

In some embodiments, $R_1$ represents a 3-(trifluoromethyl)-1H-pyrazol-1-yl group.

In some embodiments, $R_1$ represents a, 3-(hydroxymethyl)-5-methyl-1H-pyrazol-1-yl.

In some embodiments, $R_1$ represents a 3-(fluoromethyl)-5-methyl-1H-pyrazol-1-yl group.

In some embodiments, $R_1$ represents a 4H-1,2,4-triazol-4-yl group.

In some embodiments, $R_1$ represents a 3,5-dimethyl-1H-1,2,4-triazol-1-yl group, In some embodiments, $R_1$ represents a 3-methyl-4H-1,2,4-triazol-4-yl group.

In some embodiments, $R_1$ represents a 1H-1,2,3-triazol-1-yl group.

In some embodiments, $R_1$ represents a 1H-1,2,4-triazol-1-yl group.

In some embodiments, $R_1$ represents a 1H-imidazol-1-yl group,

In some embodiments, $R_1$ represents a 1,4-dimethyl-1H-imidazol-2-yl group.

In some embodiments, $R_1$ represents a (2,4-dimethyl-1H-imidazol-5-yl) group.

In one embodiment the compound is selected from:
3-(3-(3-methyl-1H-pyrazol-5-yl)phenyl)-4-((R)-3-(2-(5,6,7,8-tetrahydro-1,8-naphthyridin-2-yl)ethyl)pyrrolidin-1-yl)butanoic acid,
3-(3-(4H-1,2,4-triazol-4-yl)phenyl)-4-((R)-3-(2-(5,6,7,8-tetrahydro-1,8-naphthyridin-2-yl)ethyl)pyrrolidin-1-yl)butanoic acid,
3-(3-(4H-1,2,4-triazol-4-yl)phenyl)-4-((R)-3-(2-(5,6,7,8-tetrahydro-1,8-naphthyridin-2-yl)ethyl)pyrrolidin-1-yl)butanoic acid,
3-(3-(3,5-dimethyl-1H-1,2,4-triazol-1-yl)phenyl)-4-((R)-3-(2-(5,6,7,8-tetrahydro-1,8-naphthyridin-2-yl)ethyl)pyrrolidin-1-yl)butanoic acid,
3-(3-(3-methyl-4H-1,2,4-triazol-4-yl)phenyl)-4-((R)-3-(2-(5,6,7,8-tetra hydro-1,8-naphthyridin-2-yl)ethyl)pyrrolidin-1-yl)butanoic acid,
3-(3-(3-(2-hydroxypropa n-2-yl)-5-methyl-1H-pyrazol-1-yl)phenyl)-4-((R)-3-(2-(5,6,7,8-tetra hydro-1,8-naphthyridin-2-yl)ethyl)pyrrolidin-1-yl)butanoic acid,
4-((R)-3-(2-(5,6,7,8-tetrahydro-1,8-naphthyridin-2-yl)ethyl)pyrrolidin-1-yl)-3-(3-(3-(trifluoromethyl)-1H-pyrazol-1-yl)phenyl)butanoic acid,
3-(3-(1H-1,2,3-triazol-1-yl)phenyl)-4-((R)-3-(2-(5,6,7,8-tetrahydro-1,8-naphthyridin-2-yl)ethyl)pyrrolidin-1-yl)butanoic acid,
3-(3-(1H-imidazol-1-yl)phenyl)-4-((R)-3-(2-(5,6,7,8-tetrahydro-1,8-naphthyridin-2-yl)ethyl)pyrrolidin-1-yl)butanoic acid,
3-(3-(3-(hydroxymethyl)-5-methyl-1H-pyrazol-1-yl)phenyl)-4-((R)-3-(2-(5,6,7,8-tetrahydro-1,8-naphthyridin-2-yl)ethyl)pyrrolidin-1-yl)butanoic acid,
3-(3-(3-(fluoromethyl)-5-methyl-1H-pyrazol-1-yl)phenyl)-4-((R)-3-(2-(5,6,7,8-tetrahydro-1,8-naphthyridin-2-yl)ethyl)pyrrolidin-1-yl)butanoic acid,
3-(3-(1,4-dimethyl-1H imidazol-2-yl)phenyl)-4-((R)-3-(2-(5,6,7,8-tetrahydro-1,8-naphthyridin-2-yl)ethyl)pyrrolidin-1-yl)butanoic acid
(S)-3-(3-(2,4-dimethyl-1H-imidazol-5-yl)phenyl)-4-((R)-3-(2-(5,6,7,8-tetrahydro-1,8-naphthyridin-2-yl)ethyl)pyrrolidin-1-yl)butanoic acid and
(S)-3-(3-(1H-1,2,4-triazol-1-yl)phenyl)-4-((R)-3-(2-(5,6,7,8-tetrahydro-1,8-naphthyridin-2-yl)ethyl)pyrrolidin-1-yl)butanoic acid.

or a pharmaceutically acceptable salt thereof.

Compounds of formula (I) or (IA) or (IB) have both a basic amine group and a carboxylic acid group and can consequently form internal salts, i.e. a zwitterion or inner salts. Therefore, in an embodiment the compound of formula (I) is in a zwitterionic salt form. In another embodiment, the compound of formula (IA) is in a zwitterionic salt form. In another embodiment, the compound of formula (IB) is in a zwitterionic salt form.

It will be appreciated that the present invention covers compounds of formula (I) as the parent compound and as salts thereof, for example as a pharmaceutically acceptable salt thereof. In one embodiment the invention relates to compounds of formula (I) or a pharmaceutically acceptable salt thereof.

For a review on suitable salts see Berge et al., *J. Pharm. Sci.*, 66:1-19, (1977). Suitable pharmaceutically acceptable salts are listed in P H Stahl and C G Wermuth, editors, *Handbook of Pharmaceutical Salts; Properties, Selection and Use*, Weinheim/Zurich: Wiley-VCH/VHCA, 2002. Suitable pharmaceutically acceptable salts can include acid addition salts with inorganic acids such, for example, as hydrochloric acid, hydrobromic acid, orthophosphoric acid, nitric acid, phosphoric acid, or sulphuric acid, or with organic acids such, for example as methanesulphonic acid, ethanesulphonic acid, p-toluenesulphonic acid, acetic acid, propionic acid, lactic acid, citric acid, fumaric acid, malic acid, succinic acid, salicylic acid, maleic acid, glycerophosphoric acid, tartaric, benzoic, glutamic, aspartic, benzenesulphonic, naphthalenesulphonic such as 2-naphthalenesulphonic, hexanoic acid or acetylsalicylic acid.

Typically, a pharmaceutically acceptable salt may readily be prepared by using a desired acid or base as appropriate. The resultant salt may precipitate from solution and be collected by filtration or may be recovered by evaporation of the solvent.

Other non-pharmaceutically acceptable salts, e.g. formates, oxalates or trifluoroacetates, may be used, for example in the isolation of the compounds of formula (I), and are included within the scope of this invention.

A pharmaceutically acceptable base addition salt can be formed by reaction of a compound of formula (I) with a suitable organic base, (e.g. triethylamine, ethanolamine, triethanolamine, choline, arginine, lysine or histidine), optionally in a suitable solvent, to give the base addition salt which is usually isolated, for example, by crystallisation and filtration. Pharmaceutically acceptable inorganic base salts include ammonium salts, alkali metal salts such as those of sodium and potassium, alkaline earth metal salts such as those of calcium and magnesium and salts with organic bases, including salts of primary, secondary and tertiary amines, such as isopropylamine, diethylamine, ethanolamine, trimethylamine, dicyclohexyl amine and N-methyl-D-glucamine.

In one embodiment the compound of formula (I) is in the form of a parent compound.

The invention includes within its scope all possible stoichiometric and non-stoichiometric forms of the salts of the compounds of formula (I).

It will be appreciated that many organic compounds can form complexes with solvents in which they are reacted or from which they are precipitated or crystallized. These complexes are known as "solvates". For example, a complex with water is known as a "hydrate". Solvents with high boiling points and/or capable of forming hydrogen bonds such as water, xylene, N-methyl pyrrolidinone, methanol and ethanol may be used to form solvates. Methods for identification of solvates include, but are not limited to, NMR and microanalysis. It will be appreciated that crystalline forms optionally may be solvated to form, for example, pharmaceutically acceptable solvates, such as hydrates which may be stoichiometric hydrates as well as compounds containing variable amounts of water. Solvates include stoichiometric solvates and non-stoichiometric solvates. Compounds of formula (I) may exist in solvated or non-solvated form.

The compounds of formula (I) may be in crystalline or amorphous form. Furthermore, some of the crystalline forms of the compounds of formula (I) may exist as polymorphs, which are included within the scope of the present invention. Polymorphic forms of compounds of formula (I) may be characterized and differentiated using a number of conventional analytical techniques, including, but not limited to, X-ray powder diffraction (XRPD) patterns, infrared (IR) spectra, Raman spectra, differential scanning calorimetry (DSC), thermogravimetric analysis (TGA) and solid state nuclear magnetic resonance (SSNMR).

The compounds described herein contain two asymmetric centres so that optical isomers, e.g. diastereoisomers and enantiomers may be formed. Accordingly, the present invention encompasses isomers of the compounds of formula (I) whether as individual isomers isolated such as to be substantially free of the other isomer (i.e. pure) or as mixtures. An individual isomer isolated such as to be substantially free of the other isomer (i.e. pure) may be isolated such that less than 10%, particularly less than about 1%, for example less than about 0.1% of the other isomer is present.

It will be understood by those skilled in the art that certain diastereoisomers may be less active than others and that the activity of an individual diastereoisomer may fall below a selected limit.

In one embodiment, the compound is (IA):

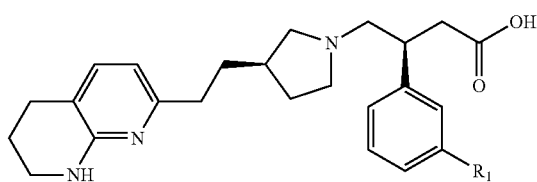

or a pharmaceutically acceptable salt thereof.

In another embodiment the compound is (IB):

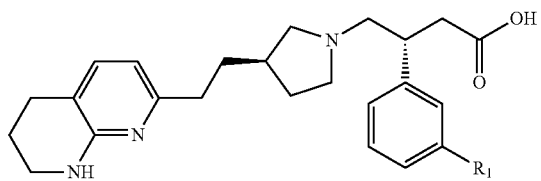

or a pharmaceutically acceptable salt thereof.

Separation of isomers may be achieved by conventional techniques known to those skilled in the art, e.g. by fractional crystallisation, chromatography, HPLC or a combination of these techniques.

Compounds of formula (I) may exist in one of several tautomeric forms. It will be understood that the present invention encompasses all tautomers of the compounds of formula (I) whether as individual tautomers or as mixtures thereof.

It will be appreciated from the foregoing that included within the scope of the invention are solvates, isomers and polymorphic forms of the compounds of formula (I) and salts thereof.

Certain compounds of formula (I) may be labelled with [18F] to form a compound suitable for use as a PET ligand for the diagnosis of diseases, such as idiopathic pulmonary fibrosis. Resulting [18F] labelled compounds are included within the scope of the present invention.

In a sixth aspect of the present invention, there is provided a compound of formula (XI)

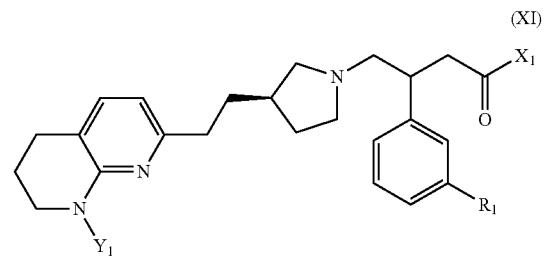

wherein $R_1$ is as hereinbefore defined, $X_1$ represents hydroxyl or a moiety which is hydrolysable by metabolism in the human body to form the corresponding acid compound of formula (I) in which $X_1$ is —OH;

$Y_1$ represents hydrogen or a moiety which is hydrolysable by metabolism in the human body to form the corresponding amino compound of formula (I) in which $Y_1$ is hydrogen;

provided that when $X_1$ is hydroxyl, then $Y_1$ is not hydrogen.

In some embodiments $X_1$ may be a moiety —ORa such that the compound of formula (I) is an ester.

For example the moiety Ra may be selected from $C_{1-6}$ alkyl (with the above-mentioned exceptions) such as methyl, ethyl, n-propyl, iso-propyl, n-butyl, iso-butyl, sec-butyl, tert-butyl, pentyl (and its isomers) or hexyl (and its isomers); or from $C_{1-6}$ alkoxyalkyl such as 2-methoxyethyl; or from $C_{1-6}$ alkylaminoalkyl such as 2-(dimethylamino) ethyl; or from $C_{1-6}$ cyclic carbonate groups such as (5-methyl-2-oxo-1,3-dioxol-4-yl) methyl; or $C_{1-6}$ acyloxyalkyl such as (pivaloyloxy)methyl.

For example the moiety Ra may be selected from aryl groups such as phenyl, 5-indanyl or L-tyrosinyl.

For example the moiety Ra may be selected from groups containing an amino group or an amide group, such as $C_{1-6}$ groups of formula —$(CH_2)_n$NRbRc or —$(CH_2)_n$CO NRbRc where n is 1-3 and Ra and Rb are independently H or $C_{1-6}$ alkyl, cycloalkyl, heterocyclyl or Ra and Rb together form a cyclic group such as morpholinyl. Examples of such moieties include dimethylaminoethyl, 2-(4-morpholino)ethyl, and dimethylamino-2-oxoethyl.

For example the moiety Ra may be selected from a hydroxyl containing an alpha-aminoacid such as L-serine and L-threonine.

For example the moiety Ra may be a cyclic carbonate of formula:

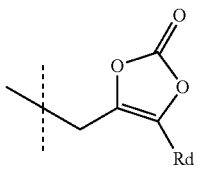

wherein Rd is hydrogen, methyl, ethyl or iso-propyl.

For example, the moiety Ra may be selected from —CHRe—O—CO—Rf in which Re is hydrogen or $C_{1-3}$ alkyl such as methyl, ethyl or iso-propyl, and Rf is $C_{1-4}$ alkyl such as methyl, ethyl, iso-propyl, tert-butyl or $C_{5-6}$ cycloalkyl, or tetrahydropyranyl.

For example, the moiety Ra may be selected from —CH(Rg)-O—CO—O-Ri in which Rg is hydrogen or $C_{1-3}$ alkyl such as methyl, ethyl or iso-propyl, and Ri is $C_{1-4}$ alkyl such as methyl, ethyl, tert-butyl or $C_{5-6}$ cycloalkyl or tetrahydropyranyl.

In some embodiments $X_1$ may be a moiety —NHRj such that the compound of formula (I) is an amide, wherein Rj may for example be $C_{1-6}$ alkyl. For example the compound of formula (I) may be an amide derived from an amino acid linked to the alpha-amino group of the amino acid, e.g. a naturally occurring L-proteinogenic amino acid such as glycine, alanine, phenylalanine, leucine, valine, isoleucine, proline, methionine, cysteine, serine, threonine, histidine, tyrosine, tryptophane, lysine, asparagine, glutamine, glutamic acid, aspartic acid, or arginine, or a di-peptide of the above-mentioned proteinogenic aminoacids. For example Rj may be a proteinogenic amino acid moiety, such as a L-lysine moiety linked to the side-chain epsilon-amino group of the amino acid e.g. —$(CH_2)_4CH(NH_2)CO_2H$.

For example Rj may be a sulfonamide moiety such as —$SO_2$—Rk where Rk is $C_{1-6}$ alkyl, such as methyl, or —NRmRn and Rm and Rn are independently H or $C_{1-6}$ alkyl, cycloalkyl, heterocyclyl or Rm and Rn together form a cyclic group such as morpholinyl.

In some embodiments $Y_1$ may be hydrogen.

In one embodiment (a) $Y_1$ is a $C_{1-6}$ alkyl substituted by a $C_{1-6}$ cyclic carbonate group, for example a (oxodioxolenyl) methyl group such as

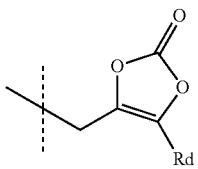

wherein Rd is $C_{1-3}$ alkyl such as methyl, ethyl or iso-propyl.

In another embodiment (b) Y may be a carbamate group, for example

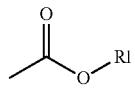

wherein R1 is $C_{1-6}$ alkyl, such as methyl, ethyl, n-propyl, iso-propyl, n-butyl, iso-butyl, n-pentyl, or n-hexyl.

In another embodiment R1 is a $C_{1-6}$ alkyl substituted by a OH or $NMe_2$ group such as —$CH_2CH_2OH$ or —$CH_2CH_2NMe_2$ In another embodiment (c) $Y_1$ may be a group of general structure

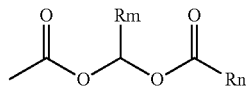

In which Rm is hydrogen, methyl or iso-propyl and Rn is $C_{1-6}$ alkyl, for example methyl, ethyl, iso-propyl, tert-butyl, cycloalkyl for example cyclobutyl, cyclopentyl, cyclohexyl, heterocyclyl for example 4-tetrahydropyranyl, aryl for example phenyl, substituted phenyl, heteroaryl for example 2-, 3- or 4-pyridyl.

In another embodiment (d) $Y_1$ may be a group of general structure

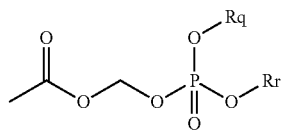

where Rq and Rr are independently hydrogen, phenyl, naphthyl, alkyl, $Et_2NCOCH_2$—, or Rq and Rr may form a $C_{1-6}$ ring, such as a saligenin.

In another embodiment compounds of formula (I) are double prodrugs where $X_1$ and $Y_1$ are as defined above in any combination.

The invention relates to all prodrugs of the compounds of formula (I) and pharmaceutically acceptable salts thereof, which upon administration to the recipient are capable of providing (directly or indirectly) a compound of formula (I) or a pharmaceutically acceptable salt thereof, or an active metabolite or residue thereof. Other suitable prodrugs of the compounds of formula (I) are readily apparent to a person skilled in the art (see for instance Burger's Medicinal Chemistry and Drug Discovery, 5$^{th}$ Edition, Vol 1: Principles and Practice, and J. Rautio et al (Nature Reviews Drug Discovery 2008, 7, 255-270).

Compound Preparation

The compounds of the invention may be made by a variety of methods, including standard chemistry. Any previously defined variable will continue to have the previously defined meaning unless otherwise indicated. Illustrative general synthetic methods are set out below and then specific compounds of the invention are prepared in the working Examples.

Compounds of structural formula (I) may be prepared by a process involving first deprotection i.e. cleavage of the ester group, followed by conversion to a salt, of a compound of structural formula (II):

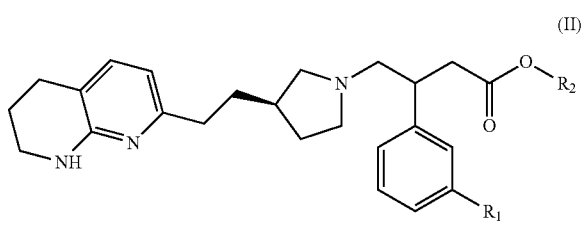

(II)

wherein $R_1$ is a hereinbefore defined, and
$R_2$ is a $C_1$ to $C_6$ alkyl group, for example methyl, or tert-butyl.

The deprotection of compound of structural formula (II) where $R_2$ is methyl may be accomplished by base hydrolysis using for example aqueous sodium hydroxide or potassium hydroxide in a suitable solvent, such as methanol, 1,4-dioxane.

The deprotection of compound of structural formula (II) where $R_2$ is tert-butyl may be accomplished by acid cleavage using for example trifluoroacetic acid or HCl in a suitable solvent such as dichloromethane, 1,4-dioxane, or water.

After the cleavage of the ester group the resulting product may be converted to the required salt by methods well known to those skilled in the art.

Compounds of structural formula (II), where the $R_1$ five-membered heterocyclic aromatic ring is linked via carbon, may be prepared by a coupling process involving a compound of structural formula (III),

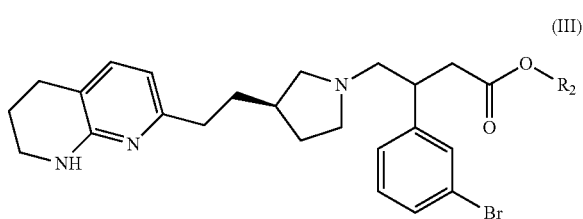

(III)

with a boronate ester or a boronic acid of the said aromatic heterocycle of structural compound (IV)

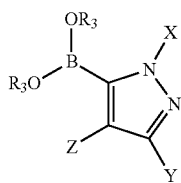

(IV)

where $R_3$ is hydrogen or a cyclic alcohol, such as pinacol. Compounds of structural formula (IV) may be used as the pure boronic acid ($R_3$=H), or as boronic acid ester ($R_3$=alkyl group for example pinacolyl), which may be converted in situ to the boronic acid in the presence of water and a base, such as potassium hydroxide and X, Y and Z are hydrogen or alkyl groups e.g. methyl in the presence of a base, such as tripotassium phosphate, and a catalyst, such as chloro(di-norbonylphosphino)(2'-dimethylamino-1,1'-biphenyl-2-yl)palladium (II) in a suitable solvent, such as aqueous ethanol and at elevated temperature, for example 130° C., optionally in a microwave reactor. During this coupling process the methyl ester group of compound (II) may hydrolyse under the basic reaction conditions to provide compound (I) directly without the need of a separate hydrolysis step.

Compounds of structural formula (III), may be prepared by a coupling process involving a compound of structural formula (V):

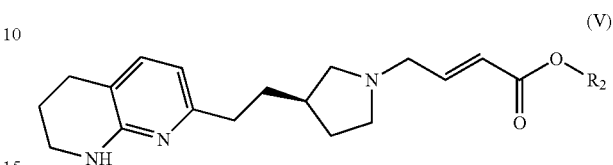

(V)

wherein $R_2$ is as defined previously and the geometry of the double bond may be (E) or mixture of (E) and (Z) isomers, preferably pure (E) isomer, with (3-bromophenyl)boronic acid (available from Aldrich) in the presence of a suitable catalyst, such as chloro(1,5-cyclooctadiene)rhodium(I) dimer or bis(norbornadiene)rhodium(I) tetrafluoroborate, optionally in the presence of a chiral ligand, such as (R)-BINAP, in a suitable solvent, such as 1,4-dioxane and at an elevated temperature, for example 95° C.

The coupling reaction in the presence of (R)-BINAP provided a diastereoisomeric mixture with a predominant isomer. The diastereoisomers may be separated by a variety of separation techniques including crystallisation, chromatography or preferably preparative chiral HPLC on a Chiralpak or Chiralcel column. The predominant diastereoisomer when using (R)-BINAP has the (S) configuration.

Compounds of structural formula (V) may be prepared by an alkylation reaction of compound of structural formula (VI):

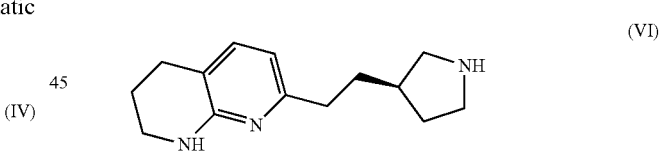

(VI)

with (E)-methyl 4-bromobut-2-enoate where $R_2$ is methyl or with (E)-tert-butyl 4-bromobut-2-enoate where $R_2$ is tert-butyl, and in the presence of a base, such as diisopropylethylamine in a suitable solvent such as dichloromethane.

Alternatively, the alkylation of compound of structural formula (VI) may be effected by coupling a compound of structural formula (VI) with (E)-methyl 4-acetoxybut-2-enoate where $R_2$ is methyl, or with tert-butyl (E)-tert-butyl 4-acetoxybut-2-enoate where $R_2$ is tert-butyl in the presence of a palladium catalyst, such as 1,1'-bis(diphenylphosphino)ferrocene]dichloropalladium(II), in the presence of a base, such as diisopropylethylamine or triethylamine and in a suitable solvent, such as dichloromethane at ambient temperature.

Compounds of structural formula (VI), may be prepared by cleavage of the tert-butoxycarbonyl protecting group of a compound of formula (VII):

(VII)

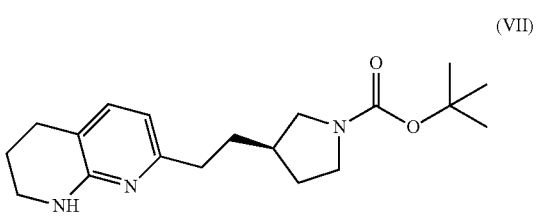 [SMILES: CC(C)(C)OC(=O)N1CC[C@@H](CCc2ccc3c(n2)NCCC3)C1]

using an acid, such as hydrogen chloride in 1,4-dioxane.

Compounds of structural formula (VII), may be prepared from compound of structural formula (VIII):

(VIII)

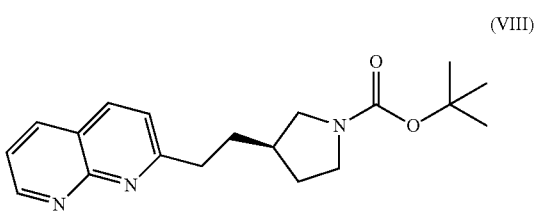 [SMILES: CC(C)(C)OC(=O)N1CC[C@@H](CCc2ccc3cccnc3n2)C1]

by hydrogenation over a catalyst, such as 5% rhodium on carbon in a solvent, such as ethanol.

In an alternative method, compounds of structural formula (II) may be prepared from compounds of formula (V) by reaction with a boronic acid or boronate ester of structural formula (IX):

(IX)

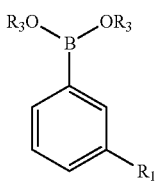

The coupling reaction in the presence of R-BINAP provided a diastereoisomeric mixture with a predominant isomer. The diastereoisomers may be separated by a variety of separation techniques, including crystallisation, chromatography or preferably preparative chiral HPLC. Compounds of structural formula (IX) may be used as the pure boronic acid ($R_3$=H), or as boronic acid ester ($R_3$=alkyl group, e.g. pinacol), which may be converted in situ to the boronic acid in the presence of water and a base, such as potassium hydroxide. The methyl ester group of compound (II) may be hydrolysed under the basic reaction conditions during the coupling process to provide compound (I) directly without the need of a separate hydrolysis step.

Where $R_1$ is the nitrogen linked aromatic heterocycle as defined previously and $R_3$ is hydrogen or a cyclic alcohol such as pinacol.

Compounds of structural formula (IX), where $R_3$ is pinacol, may be prepared from compounds of structural formula (X):

(X)

with bis(pinacolato)diboron (available from Aldrich), in the presence of palladium catalyst, such as tris(dibenzylideneacetone)dipalladium (available from Aldrich), and in the presence of a phosphine ligand, such as 2-dicyclohexylphosphino-2',4',6'-triisopropylbiphenyl (X-PHOS) (available from Aldrich), and in the presence of potassium acetate, in an inert solvent, such as 1,4-dioxane, at elevated temperature, for example 110° C., and in an inert atmosphere, such as nitrogen. Addition of water to the reaction mixture at the end of the reaction causes hydrolysis of the resulting pinacolato ester to provide the required boronic acid.

Compounds of structural formula (X) may be prepared by methods described herein.

Compound of structural formula (VIII) [(R)-tert-Butyl 3-(2-(1,8-naphthyridin-2-yl)ethyl)pyrrolidine-1-carboxylate] may be prepared by methods described in Scheme 1.

Scheme 1

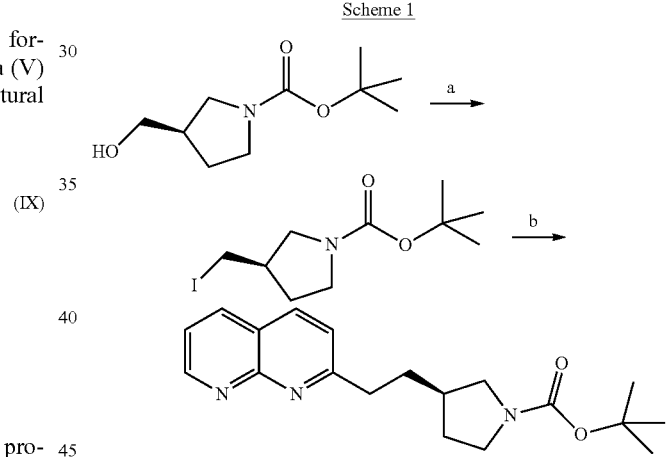

Reagents and conditions: (a) iodine, imidazole, triphenylphosphine, DCM, 0° C.; (b) 2-methyl-[1,8]-naphthyridine, LiN(TMS)$_2$, THF, 0° C.

It will be appreciated that in any of the routes described above it may be advantageous to protect one or more functional groups. Examples of protecting groups and the means for their removal can be found in T. W. Greene 'Protective Groups in Organic Synthesis' (3rd edition, J. Wiley and Sons, 1999). Suitable amine protecting groups include acyl (e.g. acetyl, carbamate (e.g. 2',2',2'-trichloroethoxycarbonyl, benzyloxycarbonyl or t-butoxycarbonyl) and arylalkyl (e.g. benzyl), which may be removed by hydrolysis (e.g. using an acid such as hydrochloric acid in dioxane or trifluoroacetic acid in dichloromethane) or reductively (e.g. hydrogenolysis of a benzyl or benzyloxycarbonyl group or reductive removal of a 2',2',2'-trichloroethoxycarbonyl group using zinc in acetic acid) as appropriate. Other suitable amine protecting groups include trifluoroacetyl (—COCF$_3$) which may be removed by base catalysed hydrolysis.

It will be appreciated that in any of the routes described above, the precise order of the synthetic steps by which the various groups and moieties are introduced into the molecule may be varied. It will be within the skill of the practitioner in the art to ensure that groups or moieties introduced at one stage of the process will not be affected by subsequent transformations and reactions, and to select the order of synthetic steps accordingly.

The absolute configuration of compound (I) may be obtained following an independent enantioselective asymmetric synthesis from an intermediate of known absolute configuration. Alternatively enantiomerically pure compound (I) may be converted into a compound whose absolute configuration is known. In either case comparison of spectroscopic data, optical rotation and retention times on analytical chiral HPLC may be used to confirm absolute configuration. A third option, where feasible, is determination of absolute configuration from an X-ray crystal structure.

Certain compounds of formulae (II) to (X) are also believed to be novel and therefore form yet a further aspect of the invention.

Methods of Use

The compounds of formula (I) and salts thereof are believed to have $\alpha_v$ integrin antagonist activity, particularly $\alpha_v\beta_6$ receptor activity, and thus have potential utility in the treatment of diseases or conditions for which an $\alpha_v \beta_6$ antagonist is indicated.

The present invention thus provides a compound of formula (I) or a pharmaceutically acceptable salt thereof for use in therapy. The compound of formula (I) or pharmaceutically acceptable salt thereof can be for use in the treatment of a disease or condition for which an $\alpha_v\beta_6$ integrin antagonist is indicated.

The present invention thus provides a compound of formula (I) or a pharmaceutically acceptable salt thereof for use in the treatment of a disease or condition for which an $\alpha_v\beta_6$ integrin antagonist is indicated.

Also provided is the use of a compound of formula (I) or a pharmaceutically acceptable salt thereof in the manufacture of a medicament for the treatment of a disease or condition for which an $\alpha_v\beta_6$ integrin antagonist is indicated.

Also provided is a method of treating a disease or conditions for which an $\alpha_v\beta_6$ integrin antagonist is indicated in a subject in need thereof which comprises administering a therapeutically effective amount of compound of formula (I) or a pharmaceutically acceptable salt thereof.

Suitably the subject in need thereof is a mammal, particularly a human.

As used herein, the term "effective amount" means that amount of a drug or pharmaceutical agent that will elicit the biological or medical response of a tissue, system, animal or human that is being sought, for instance, by a researcher or clinician. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

Fibrotic diseases involve the formation of excess fibrous connective tissue in an organ or tissue in a reparative or reactive process. $\alpha_v\beta_6$ antagonists are believed to be useful in the treatment of a variety of such diseases or conditions including those dependent on $\alpha_v\beta_6$ integrin function and on activation of transforming growth factor beta via alpha v integrins. Diseases may include but are not limited to pulmonary fibrosis (e.g. idiopathic pulmonary fibrosis, non-specific interstitial pneumonia (NSIP), usual interstitial pneumonia (UIP), Hermansky-Pudlak syndrome, progressive massive fibrosis (a complication of coal workers' pneumoconiosis), connective tissue disease-related pulmonary fibrosis, airway fibrosis in asthma and COPD, ARDS associated fibrosis, acute lung injury, radiation-induced fibrosis, familial pulmonary fibrosis, pulmonary hypertension); renal fibrosis (diabetic nephropathy, IgA nephropathy, lupus nephritis, focal segmental glomerulosclerosis (FSGS), transplant nephropathy, autoimmune nephropathy, drug-induced nephropathy, hypertension-related nephropathy, nephrogenic systemic fibrosis); liver fibrosis (virally-induced fibrosis (e.g. hepatitis C or B), autoimmune hepatitis, primary biliary cirrhosis, alcoholic liver disease, non-alcoholic fatty liver disease including non-alcoholic steatohepatitis (NASH), congenital hepatic fibrosis, primary sclerosing cholangitis, drug-induced hepatitis, hepatic cirrhosis); skin fibrosis (hypertrophic scars, scleroderma, keloids, dermatomyositis, eosinophilic fasciitis, Dupytrens contracture, Ehlers-Danlos syndrome, Peyronie's disease, epidermolysis bullosa dystrophica, oral submucous fibrosis); ocular fibrosis (age-related macular degeneration (AMD), diabetic macular oedema, dry eye, glaucoma) corneal scarring, corneal injury and corneal wound healing, prevention of filter bleb scarring post trabeculectomy surgery; cardiac fibrosis (congestive heart failure, atherosclerosis, myocardial infarction, endomyocardial fibrosis, hypertrophic cardiomyopathy (HCM)) and other miscellaneous fibrotic conditions (mediastinal fibrosis, myelofibrosis, retroperitoneal fibrosis, Crohn's disease, neurofibromatosis, uterine leiomyomas (fibroids), chronic organ transplant rejection. There may be additional benefits for additional inhibition of $\alpha_v\beta_1$, $\alpha_v\beta_5$ or $\alpha_v\beta_8$ integrins In addition, pre-cancerous lesions or cancers associated with $\alpha_v\beta_6$ integrins may also be treated (these may include but are not limited to endometrial, basal cell, liver, colon, cervical, oral, pancreas, breast and ovarian cancers, Kaposi's sarcoma, Giant cell tumours and cancer associated stroma). Conditions that may derive benefit from effects on angiogenesis may also benefit (e.g. solid tumours).

The term "disease or condition for which an $\alpha_v\beta_6$ antagonist is indicated", is intended to include any or all of the above disease states.

In one embodiment the disease or condition for which an $\alpha_v\beta_6$ antagonist is indicated is idiopathic pulmonary fibrosis.

In another embodiment the disease or condition for which an $\alpha_v\beta_6$ antagonist is indicated is selected from corneal scarring, corneal injury and corneal wound healing.

Compositions

While it is possible that for use in therapy, a compound of formula (I) as well as pharmaceutically acceptable salts thereof may be administered as the raw chemical, it is common to present the active ingredient as a pharmaceutical composition.

The present invention therefore provides in a further aspect a pharmaceutical composition comprising a compound of formula (I) or a pharmaceutically acceptable salt and one or more pharmaceutically acceptable carriers, diluents and/or excipients. The compounds of the formula (I) and pharmaceutically acceptable salts, are as described above. The carrier(s), diluent(s) or excipient(s) must be acceptable in the sense of being compatible with the other ingredients of the composition and not deleterious to the recipient thereof.

In accordance with another aspect of the invention there is also provided a process for the preparation of a pharmaceutical composition including admixing a compound of the formula (I), or a pharmaceutically acceptable salt thereof, with one or more pharmaceutically acceptable carriers, diluents or excipients. The pharmaceutical composition can be for use in the treatment of any of the conditions described herein.

Further provided is a pharmaceutical composition for the treatment of diseases or conditions for which an $\alpha_v\beta_6$ integrin antagonist is indicated comprising a compound of formula (I) or a pharmaceutically acceptable salt thereof.

Further provided is a pharmaceutical composition comprising 0.01 to 3000 mg of a compound of formula (I) or a pharmaceutical salt thereof and 0.1 to 2 g of one or more pharmaceutically acceptable carriers, diluents or excipients.

Since the compounds of formula (I) are intended for use in pharmaceutical compositions it will be readily understood that they are each preferably provided in substantially pure form, for example, at least 60% pure, more suitably at least 75% pure and preferably at least 85% pure, especially at least 98% pure (% in a weight for weight basis).

Pharmaceutical compositions may be presented in unit dose forms containing a predetermined amount of active ingredient per unit dose. Preferred unit dosage compositions are those containing a daily dose or sub-dose, or an appropriate fraction thereof, of an active ingredient. Such unit doses may therefore be administered more than once a day. Preferred unit dosage compositions are those containing a daily dose or sub-dose (for administration more than once a day), as herein above recited, or an appropriate fraction thereof, of an active ingredient.

Pharmaceutical compositions may be adapted for administration by any appropriate route, for example by the oral (including buccal or sublingual), rectal, inhaled, intranasal, topical (including buccal, sublingual or transdermal), vagina, ocular or parenteral (including subcutaneous, intramuscular, intravenous or intradermal) route. Such compositions may be prepared by any method known in the art of pharmacy, for example by bringing into association the active ingredient with the carrier(s) or excipient(s).

In one embodiment the pharmaceutical composition is adapted for oral administration.

Pharmaceutical compositions adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

For instance, for oral administration in the form of a tablet or capsule, the active drug component can be combined with an oral, non-toxic pharmaceutically acceptable inert carrier such as ethanol, glycerol, water and the like. Powders suitable for incorporating into tablets or capsules may be prepared by reducing the compound to a suitable fine particle size (e.g. by micronisation) and mixing with a similarly prepared pharmaceutical carrier such as an edible carbohydrate, as, for example, starch or mannitol. Flavoring, preservative, dispersing and coloring agent can also be present.

Capsules may be made by preparing a powder mixture, as described above, and filling formed gelatin sheaths. Glidants and lubricants such as colloidal silica, talc, magnesium stearate, calcium stearate or solid polyethylene glycol can be added to the powder mixture before the filling operation. A disintegrating or solubilising agent such as agaragar, calcium carbonate or sodium carbonate can also be added to improve the availability of the medicament when the capsule is ingested.

Moreover, when desired or necessary, suitable binders, glidants, lubricants, sweetening agents, flavours, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like.

Lubricants used in these dosage forms include sodium oleate, sodium stearate, magnesium stearate, sodium benzoate, sodium acetate, sodium chloride and the like.

Disintegrators include, without limitation, starch, methyl cellulose, agar, bentonite, xanthan gum and the like. Tablets are formulated, for example, by preparing a powder mixture, granulating or slugging, adding a lubricant and disintegrant and pressing into tablets. A powder mixture is prepared by mixing the compound, suitably comminuted, with a diluent or base as described above, and optionally, with a binder such as carboxymethylcellulose, an alginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acadia mucilage or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc or mineral oil. The lubricated mixture is then compressed into tablets. The compounds of the present invention can also be combined with a free flowing inert carrier and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solution, syrups and elixirs can be prepared in dosage unit form so that a given quantity contains a predetermined amount of the compound. Syrups can be prepared by dissolving the compound in a suitably flavoured aqueous solution, while elixirs are prepared through the use of a non-toxic alcoholic vehicle. Suspensions can be formulated by dispersing the compound in a non-toxic vehicle. Solubilizers and emulsifiers such as ethoxylated isostearyl alcohols and polyoxy ethylene sorbitol ethers, preservatives, flavour additive such as peppermint oil or natural sweeteners or saccharin or other artificial sweeteners, and the like can also be added.

Where appropriate, dosage unit compositions for oral administration can be microencapsulated. The formulation can also be prepared to prolong or sustain the release as for example by coating or embedding particulate material in polymers, wax or the like.

The compounds of the invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Pharmaceutical compositions adapted for transdermal administration may be presented as discrete patches intended to remain in intimate contact with the epidermis of the recipient for a prolonged period of time.

Pharmaceutical compositions adapted for topical administration may be formulated as ointments, creams, suspensions, lotions, powders, solutions, pastes, gels, sprays, aerosols or oils.

For treatments of the eye or other external tissues, for example mouth and skin, the compositions are preferably applied as a topical ointment or cream. When formulated in an ointment, the active ingredient may be employed with either a paraffinic or a water miscible ointment base. Alternatively, the active ingredient may be formulated in a cream with an oil-in-water cream base or a water-in-oil base. The compounds of this invention can be administered as topical eye drops. The compounds of this invention can be administered via sub-conjunctival, intracameral or intravitreal routes which would necessitate administration intervals that are longer than daily.

Pharmaceutical formulations adapted for topical administrations to the eye include eye drops wherein the active ingredient is dissolved or suspended in a suitable carrier, especially an aqueous solvent. Formulations to be administered to the eye will have ophthalmically compatible pH and osmolality. One or more ophthalmically acceptable pH adjusting agents and/or buffering agents can be included in a composition of the invention, including acids such as acetic, boric, citric, lactic, phosphoric and hydrochloric acids; bases such as sodium hydroxide, sodium phosphate, sodium borate, sodium citrate, sodium acetate, and sodium lactate; and buffers such as citrate/dextrose, sodium bicarbonate and ammonium chloride. Such acids, bases, and buffers can be included in an amount required to maintain pH of the composition in an ophthalmically acceptable range. One or more ophthalmically acceptable salts can be included in the composition in an amount sufficient to bring osmolality of the composition into an ophthalmically acceptable range. Such salts include those having sodium, potassium or ammonium cations and chloride, citrate, ascorbate, borate, phosphate, bicarbonate, sulfate, thiosulfate or bisulfite anions.

The ocular delivery device may be designed for the controlled release of one or more therapeutic agents with multiple defined release rates and sustained dose kinetics and permeability. Controlled release may be obtained through the design of polymeric matrices incorporating different choices and properties of biodegradable/bioerodable polymers (e.g. poly(ethylene vinyl) acetate (EVA), superhydrolyzed PVA), hydroxyalkyl cellulose (HPC), methylcellulose (MC), hydroxypropyl methyl cellulose (HPMC), polycaprolactone, poly(glycolic) acid, poly(lactic) acid, polyanhydride, of polymer molecular weights, polymer crystallinity, copolymer ratios, processing conditions, surface finish, geometry, excipient addition and polymeric coatings that will enhance drug diffusion, erosion, dissolution and osmosis.

Formulations for drug delivery using ocular devices may combine one or more active agents and adjuvants appropriate for the indicated route of administration. For example, the active agents may be admixed with any pharmaceutically acceptable excipient, lactose, sucrose, starch powder, cellulose esters of alkanoic acids, stearic acid, talc, magnesium stearate, magnesium oxide, sodium and calcium salts of phosphoric and sulphuric acids, acacia, gelatin, sodium alginate, polyvinylpyrrolidine, and/or polyvinyl alcohol, tableted or encapsulated for conventional administration. Alternatively, the compounds may be dissolved in polyethylene glycol, propylene glycol, carboxymethyl cellulose colloidal solutions, ethanol, corn oil, peanut oil, cottonseed oil, sesame oil, tragacanth gum, and/or various buffers. The compounds may also be mixed with compositions of both biodegradable and non-biodegradable polymers and a carrier or diluent that has a time delay property. Representative examples of biodegradable compositions can include albumin, gelatin, starch, cellulose, dextrans, polysaccharides, poly (D, L-lactide), poly (D, L-lactide-co-glycolide), poly (glycolide), poly (hydroxybutyrate), poly (alkylcarbonate) and poly (orthoesters) and mixtures thereof. Representative examples of non-biodegradable polymers can include EVA copolymers, silicone rubber and poly (methylacrylate), and mixtures thereof.

Pharmaceutical compositions for ocular delivery also include in situ gellable aqueous composition. Such a composition comprises a gelling agent in a concentration effective to promote gelling upon contact with the eye or with lacrimal fluid. Suitable gelling agents include but are not limited to thermosetting polymers. The term "in situ gellable" as used herein includes not only liquids of low viscosity that form gels upon contact with the eye or with lacrimal fluid, but also includes more viscous liquids such as semi-fluid and thixotropic gels that exhibit substantially increased viscosity or gel stiffness upon administration to the eye. See, for example, Ludwig (2005) Adv. Drug Deliv. Rev. 3; 57:1595-639, herein incorporated by reference for purposes of its teachings of examples of polymers for use in ocular drug delivery.

Pharmaceutical compositions adapted for topical administration in the mouth include lozenges, pastilles and mouth washes.

Pharmaceutical compositions adapted for rectal administration may be presented as suppositories or as enemas.

Dosage forms for nasal or inhaled administration may conveniently be formulated as aerosols, solutions, suspensions, gels or dry powders.

For compositions suitable and/or adapted for inhaled administration, it is preferred that the compound of the invention is in a particle-size-reduced form, and more preferably the size-reduced form is obtained or obtainable by micronisation. The preferable particle size of the size-reduced (e.g. micronised) compound or salt is defined by a D50 value of about 0.5 to about 10 microns (for example as measured using laser diffraction).

Aerosol formulations, e.g. for inhaled administration, can comprise a solution or fine suspension of the active substance in a pharmaceutically acceptable aqueous or non-aqueous solvent. Aerosol formulations can be presented in single or multidose quantities in sterile form in a sealed container, which can take the form of a cartridge or refill for use with an atomising device or inhaler. Alternatively the sealed container may be a unitary dispensing device such as a single dose nasal inhaler or an aerosol dispenser fitted with a metering valve (metered dose inhaler) which is intended for disposal once the contents of the container have been exhausted.

Where the dosage form comprises an aerosol dispenser, it preferably contains a suitable propellant under pressure such as compressed air, carbon dioxide or an organic propellant such as a hydrofluorocarbon (HFC). Suitable HFC propellants include 1,1,1,2,3,3,3-heptafluoropropane and 1,1,1,2-tetrafluoroethane. The aerosol dosage forms can also take the form of a pump-atomiser. The pressurised aerosol may contain a solution or a suspension of the active compound. This may require the incorporation of additional excipients e.g. co-solvents and/or surfactants to improve the dispersion characteristics and homogeneity of suspension formulations. Solution formulations may also require the addition of co-solvents such as ethanol. Other excipient modifiers may also be incorporated to improve, for example, the stability and/or taste and/or fine particle mass characteristics (amount and/or profile) of the formulation.

For pharmaceutical compositions suitable and/or adapted for inhaled administration, the pharmaceutical composition may be a dry powder inhalable composition. Such a composition can comprise a powder base such as lactose, glucose, trehalose, mannitol or starch, the compound of formula (I) or salt thereof (preferably in particle-size-reduced form, e.g. in micronised form), and optionally a performance modifier such as L-leucine or another amino acid and/or metals salts of stearic acid such as magnesium or calcium stearate. Preferably, the dry powder inhalable composition comprises a dry powder blend of lactose and the compound of formula (I) or salt thereof. The lactose is preferably lactose hydrate e.g. lactose monohydrate and/or is preferably inhalation-grade and/or fine-grade lactose. Preferably, the particle size of the lactose is defined by 90% or more (by weight or by volume) of the lactose particles being less than 1000 microns (micrometers) (e.g. 10-1000 microns e.g. 30-1000 microns) in diameter, and/or 50% or more of the lactose particles being less than 500 microns (e.g. 10-500 microns) in diameter. More preferably, the particle size of the lactose is defined by 90% or more of the lactose particles being less than 300 microns (e.g. 10-300 microns e.g. 50-300 microns) in diameter, and/or 50% or more of the lactose particles being less than 100 microns in diameter. Optionally, the particle size of the lactose is defined by 90% or more of the lactose particles being less than 100-200 microns in diameter, and/or 50% or more of the lactose particles being less than 40-70 microns in diameter. Most importantly, it is preferable that about 3 to about 30% (e.g. about 10%) (by weight or by volume) of the particles are less than 50 microns or less than 20 microns in diameter. For example, without limitation, a suitable inhalation-grade lactose is E9334 lactose (10% fines) (Borculo Domo Ingredients, Hanzeplein 25, 8017 JD Zwolle, Netherlands).

Optionally, in particular for dry powder inhalable compositions, a pharmaceutical composition for inhaled administration can be incorporated into a plurality of sealed dose containers (e.g. containing the dry powder composition) mounted longitudinally in a strip or ribbon inside a suitable inhalation device. The container is rupturable or peel-openable on demand and the dose of e.g. the dry powder composition can be administered by inhalation via the device such as the DISKUS™ device, marketed by Glaxo-SmithKline. The DISKUS™ inhalation device is for example described in GB 2242134 A, and in such a device at least one container for the pharmaceutical composition in powder form (the container or containers preferably being a plurality of sealed dose containers mounted longitudinally in a strip or ribbon) is defined between two members peelably secured to one another; the device comprises: a means of defining an opening station for the said container or containers; a means for peeling the members apart at the opening station to open the container; and an outlet, communicating with the opened container, through which a user can inhale the pharmaceutical composition in powder form from the opened container.

The compounds of the invention may be formulated for inhaled or intranasal administration as a fluid formulation for delivery from a fluid dispenser, for example a fluid dispenser having a dispensing nozzle or dispensing orifice through which a metered dose of the fluid formulation is dispensed upon the application of a user-applied force to a pump mechanism of the fluid dispenser. Such fluid dispensers are generally provided with a reservoir of multiple metered doses of the fluid formulation, the doses being dispensable upon sequential pump actuations. The dispensing nozzle or orifice may be configured for insertion into the nostrils of the user for spray dispensing of the fluid formulation into the nasal cavity. A fluid dispenser of the aforementioned type is described and illustrated in WO-A-2005/044354, the entire content of which is hereby incorporated herein by reference. The dispenser has a housing which houses a fluid discharge device having a compression pump mounted on a container for containing a fluid formulation. The housing has at least one finger-operable side lever which is movable inwardly with respect to the housing to cam the container upwardly in the housing to cause the pump to compress and pump a metered dose of the formulation out of a pump stem through a nasal nozzle of the housing. A particularly preferred fluid dispenser is of the general type illustrated in FIGS. 30-40 of WO-A-2005/044354.

Compositions for inhaled or intranasal administration may also be administered to the lung and other regions of the respiratory tract by nebulisation. Such compositions may be aqueous solutions or suspensions. Solutions for inhalation by nebulisation may be formulated with the addition of agents such as acid or alkali, buffer salts, isotonicity adjusting agents, surfactants or antimicrobials, such as benzylalkonium chloride (BAC). The composition may be sterile and free of antimicrobial preservative. They may be sterilised, for example, by filtration or heating in an autoclave. They may be presented as a non-sterile solution. A single unit dose of a therapeutically effective amount of the compound of the present invention may be provided as a pre-mixed, premeasured formulation, in a single container.

Pharmaceutical compositions adapted for vaginal administration may be presented as pessaries, tampons, creams, gels, pastes, foams or spray formulations.

Pharmaceutical compositions adapted for parenteral administration include aqueous and non-aqueous sterile injection solutions which may contain anti-oxidants, buffers, bacteriostats and solutes which render the composition isotonic with the blood of the intended recipient, and aqueous and non-aqueous sterile suspensions which may include suspending agents and thickening agents. The compositions may be presented in unitdose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

A therapeutically effective amount of a compound of the present invention will depend upon a number of factors including, for example, the age and weight of the subject, the precise condition requiring treatment and its severity, the nature of the formulation, and the route of administration, and will ultimately be at the discretion of the attendant physician or veterinarian. In the pharmaceutical composition, each dosage unit for oral or parenteral administration preferably contains from 0.01 to 3000 mg, 0.1 to 2000 mg, or more typically 0.5 to 1000 mg of a compound of the invention calculated as the parent compound.

Each dosage unit for nasal or inhaled administration preferably contains from 0.001 to 50 mg, more preferably 0.01 to 5 mg, yet more preferably 10 to 50 mg, of a compound of the formula (I) or a pharmaceutically acceptable salt thereof, calculated as the free base.

For administration of a nebulised solution or suspension, a dosage unit typically contains from 1 to 15 mg, for example, from 2 mg to 10 mg, or from 4 mg to 6 mg, which may suitably be delivered once daily, twice daily or more than twice daily. The compound of the present invention may be provided in a dry or lyophilised powder for reconstitution in the pharmacy or by the patient, or may, for example, be provided in an aqueous saline solution.

Each dosage unit for nasal or inhaled administration preferably contains from 0.001 to 50 mg, more preferably 0.01 to 50 mg, yet more preferably 10 to 50 mg, of a compound of the formula (I) or a pharmaceutically acceptable salt thereof, calculated as the free base.

The pharmaceutically acceptable compounds of the invention can be administered in a daily dose (for an adult patient) of, for example, an oral or parenteral dose of 0.01 mg to 3000 mg per day or 0.5 to 1000 mg per day, or a nasal or inhaled dose of 0.001 to 50 mg per day or 0.01 to 50 mg per day, or 10 to 50 mg, of the compound of the formula (I) or a pharmaceutically acceptable salt thereof, calculated as the free base. This amount may be given in a single dose per day or more usually in a number (such as two, three, four, five or six) of sub-doses per day such that the total daily dose is the same. An effective amount of a salt thereof may be determined as a proportion of the effective amount of the compound of formula (I) per se.

The compounds of the invention may be employed alone or in combination with other therapeutic agents. Combination therapies according to the present invention thus comprise the administration of at least one compound of formula (I) or a pharmaceutically acceptable salt thereof, and the use of at least one other pharmaceutically active agent. Preferably, combination therapies according to the present invention comprise the administration of at least one compound of formula (I) or a pharmaceutically acceptable salt thereof, and at least one other pharmaceutically active agent. The compound(s) of the invention and the other pharmaceutically active agent(s) may be administered together in a single pharmaceutical composition or separately and, when administered separately this may occur simultaneously or sequentially in any order. The amounts of the compound(s) of the invention and the other pharmaceutically active agent(s) and the relative timings of administration will be selected in order to achieve the desired combined therapeutic effect.

Thus in a further aspect, there is provided a combination comprising a compound of the invention and at least one other pharmaceutically active agent.

Thus in one aspect, the compound and pharmaceutical compositions according to the invention may be used in combination with or include one or more other therapeutic agents, including therapies for allergic disease, inflammatory disease, autoimmune disease, anti-fibrotic therapies and therapies for obstructive airway disease, therapies for diabetic ocular diseases, and therapies for corneal scarring, corneal injury and corneal wound healing.

Anti-allergic therapies include antigen immunotherapy (such as components and fragments of bee venom, pollen, milk, peanut, CpG motifs, collagen, other components of extracellular matrix which may be administered as oral or sublingual antigens), anti-histamines (such as cetirizine, loratidine, acrivastine, fexofenidine, chlorphenamine), and corticosteroids (such as fluticasone propionate, fluticasone furoate, beclomethasone dipropionate, budesonide, ciclesonide, mometasone furoate, triamcinolone, flunisolide, prednisolone, hydrocortisone).

Anti-inflammatory therapies include NSAIDs (such as aspirin, ibuprofen, naproxen), leukotriene modulators (such as montelukast, zafirlukast, pranlukast), and other anti-inflammatory therapies (such as iNOS inhibitors, tryptase inhibitors, IKK2 inhibitors, p38 inhibitors (losmapimod, dilmapimod), elastase inhibitors, beta2 agonists, DP1 antagonists, DP2 antagonists, pI3K delta inhibitors, ITK inhibitors, LP (lysophosphatidic) inhibitors or FLAP (5-lipoxygenase activating protein) inhibitors (such as sodium 3-(3-(tert-butylthio)-1-(4-(6-ethoxypyridin-3-yl)benzyl)-5-((5-methylpyridin-2-yl)methoxy)-1H-indol-2-yl)-2,2-dimethylpropanoate); adenosine a2a agonists (such as adenosine and regadenoson), chemokine antagonists (such as CCR3 antagonists or CCR4 antagonists), mediator release inhibitors.

Therapies for autoimmune disease include DMARDS (such as methotrexate, leflunomide, azathioprine), biopharmaceutical therapies (such as anti-IgE, anti-TNF, anti-interleukins (such as anti-IL-1, anti-IL-6, anti-IL-12, anti-IL-17, anti-IL-18), receptor therapies (such as etanercept and similar agents); antigen non-specific immunotherapies (such as interferon or other cytokines/chemokines, cytokine/chemokine receptor modulators, cytokine agonists or antagonists, TLR agonists and similar agents).

Other anti-fibrotic therapies includes inhibitors of TGFβ synthesis (such as pirfenidone), tyrosine kinase inhibitors targeting the vascular endothelial growth factor (VEGF), platelet-derived growth factor (PDGF) and fibroblast growth factor (FGF) receptor kinases (such as Nintedanib (BIBF-1120) and imatinib mesylate (Gleevec)), endothelin receptor antagonists (such as ambrisentan or macitentan), antioxidants (such as N-acetylcysteine (NAC); broad-spectrum antibiotics (such as cotrimoxazole, tetracyclines (minocycline hydrochloride)), phosphodiesterase 5 (PDE5) inhibitors (such as sildenafil), anti-αvβx antibodies and drugs (such as anti-αvβ6 monoclonal antibodies such as those described in WO2003100033A2 may be used in combination, intetumumab, cilengitide) may be used in combination.

Therapies for obstructive airway diseases include bronchodilators such as short-acting β2-agonists, such as salbutamol), long-acting β2-agonists (such as salmeterol, formoterol and vilanterol), short-acting muscarinic antagonists (such as ipratropium bromide), long-acting muscarinic antagonists, (such as tiotropium, umeclidinium).

In some embodiments, treatment can also involve combination of a compound of this invention with other existing modes of treatment, for example existing agents for treatment of diabetic ocular diseases, such as anti VEGF therapeutics e.g. Lucentis®, Avastin®, and Aflibercept- and steroids, e.g., triamcinolone, and steroid implants containing fluocinolone acetonide.

In some embodiments, treatment can also involve combination of a compound of this invention with other existing modes of treatment, for example existing agents for treatment of corneal scarring, corneal injury or corneal wound healing, such as Gentel®, calf blood extract, Levofloxacin®, and Ofloxacin®.

The compounds and compositions of the invention may be used to treat cancers alone or in combination with cancer therapies including chemotherapy, radiotherapy, targeted agents, immunotherapy and cell or gene therapy.

It will be clear to a person skilled in the art that, where appropriate, the other therapeutic ingredient(s) may be used in the form of salts, for example as alkali metal or amine salts or as acid addition salts, or prodrugs, or as esters, for example lower alkyl esters, or as solvates, for example hydrates, to optimise the activity and/or stability and/or physical characteristics, such as solubility, of the therapeutic ingredient. It will be clear also that, where appropriate, the therapeutic ingredients may be used in optically pure form.

The combinations referred to above may conveniently be presented for use in the form of a pharmaceutical composition and thus pharmaceutical compositions comprising a combination as defined above together with a pharmaceutically acceptable diluent or carrier represent a further aspect of the invention. The individual compounds of such combinations may be administered either sequentially or simultaneously in separate or combined pharmaceutical compositions. Preferably, the individual compounds will be administered simultaneously in a combined pharmaceutical composition. Appropriate doses of known therapeutic agents will be readily appreciated by those skilled in the art.

It will be appreciated that when the compound of the present invention is administered in combination with one or more other therapeutically active agents normally administered by the inhaled, intravenous, oral, intranasal, ocular topical or other route that the resultant pharmaceutical composition may be administered by the same route. Alternatively, the individual components of the composition may be administered by different routes.

The present inventions will now be illustrated by way of example only.

Abbreviations

The following list provides definitions of certain abbreviations as used herein. It will be appreciated that the list is not exhaustive, but the meaning of those abbreviations not herein below defined will be readily apparent to those skilled in the art.
Ac (acetyl)
BCECF-AM (2',7'-bis-(2-carboxyethyl)-5-(and -6)-carboxyfluorescein acetoxymethyl ester)
BEH (Ethylene Bridged Hybrid Technology)
Bu (butyl)
CHAPS (3-[(3-Cholamidopropyl)dimethylammonio]-1-propanesulfonate)
Chiralcel OD-H (cellulose tris (3, 5-dimethylphenylcarbamate) coated on 5 μm silica gel)
Chiralpak AD-H (amylose tris (3, 5-dimethylphenylcarbamate) coated on 5 μm silica gel)
Chiralpak ID (amylose tris (3-chlorophenylcarbamate) immobilised on 5 μm silica gel)
Chiralpak AS (amylose tris ((S)-alpha-methylbenzylcarbamate) coated on 5 μm silica gel)
CSH (Charged Surface Hybrid Technology)
CV (column volume)
DCM (dichloromethane)
DIPEA (diisopropylethylamine)
DMF (N, N-dimethylformamide)
DMSO (dimethylsulfoxide)
Et (ethyl)
EtOH (ethanol)
EtOAc (ethyl acetate)
h (hour/hours)
HCl (Hydrochloric acid)
HEPES (4-(2-hydroxyethyl)-1-piperazineethanesulfonic acid)
LCMS (liquid chromatography mass spectrometry)
LiHMDS (lithium hexamethyldisilazide)
MDAP (mass directed auto-preparative HPLC)
Me (methyl)
MeCN (acetonitrile)
MeOH (methanol)
min minute/minutes
MS (mass spectrum)
$PdCl_2(dppf)$-$CH_2Cl_2$ [1,1'-Bis(diphenylphosphino)ferrocene]dichloropalladium(II), complex with dichloromethane
Ph (phenyl)
$^i$Pr (isopropyl)
(R)-BINAP (R)-(+)-2,2'-Bis (diphenylphosphino)-1,1'-binaphthalene
Si (Silica)
SPE (solid phase extraction)
TBME (tert-butyl methyl ether)
TEA (triethylamine)
TFA (trifluoroacetic acid)
THF (tetrahydrofuran)
TLC (thin layer chromatography) All references to brine refer to a saturated aqueous solution of sodium chloride.
Experimental Details
Analytical LCMS Analytical LCMS was conducted on one of the following systems A to C.

The UV detection to all systems was an averaged signal from wavelength of 220 nm to 350 nm and mass spectra were recorded on a mass spectrometer using alternate-scan positive and negative mode electrospray ionization.

Experimental details of LCMS systems A-C as referred to herein are as follows:
System A
Column: 50 mm×2.1 mm ID, 1.7 μm Acquity UPLC BEH $C_{18}$ column
Flow Rate: 1 mL/min.
Temp.: 40° C.
Solvents: A: 10 mM ammonium bicarbonate in water adjusted to pH10 with ammonia solution
B: Acetonitrile
Gradient: Time (min) A % B %

| Time (min) | A % | B % |
| --- | --- | --- |
| 0 | 99 | 1 |
| 1.5 | 3 | 97 |
| 1.9 | 3 | 97 |
| 2.0 | 99 | 1 |

System B
Column: 50 mm×2.1 mm ID, 1.7 μm Acquity UPLC BEH C18 column
Flow Rate: 1 mL/min
Temp.: 40° C.
Solvents: A: 0.1% v/v solution of formic acid in water
B: 0.1% v/v solution of formic acid in acetonitrile
Gradient:

| Time (min) | A % | B % |
| --- | --- | --- |
| 0 | 97 | 3 |
| 1.5 | 0 | 100 |
| 1.9 | 0 | 100 |
| 2.0 | 97 | 3 |

System C
Column: 50 mm×2.1 mm ID, 1.7 m Acquity UPLC CSH C18 column
Flow Rate: 1 mL/min.
Temp.: 40° C.

Solvents: A: 10 mM ammonium bicarbonate in water adjusted to pH10 with ammonia solution
B: Acetonitrile
Gradient:

| Time (min) | A % | B % |
|---|---|---|
| 0 | 97 | 3 |
| 1.5 | 5 | 95 |
| 1.9 | 5 | 95 |
| 2.0 | 97 | 3 |

System D
Column: 50 mm×2.1 mm ID, 1.7 m Acquity UPLC CSH C18 column
Flow Rate: 1 mL/min.
Temp.: 40° C.
Solvents: A: 0.1% v/v solution of formic acid in water
B: 0.1% v/v formic acid in acetonitrile
Gradient:

| Time (min) | A % | B % |
|---|---|---|
| 0 | 97 | 3 |
| 1.5 | 5 | 95 |
| 1.9 | 5 | 95 |
| 2.0 | 97 | 3 |

Mass Directed Auto-Preparative HPLC

Crude products were purified by MDAP HPLC by the following method A. The run time was 15 min unless otherwise stated. The UV detection for all methods was an averaged signal from wavelength of 210 nm to 350 nm and mass spectra were recorded on a mass spectrometer using alternate-scan positive and negative mode electrospray ionization.
Method A:

Method A was conducted on an XBridge $C_{18}$ column (typically 100 mm×30 mm i.d. 5 μm packing diameter) at ambient temperature. The solvents employed were:
A=10 mM aqueous ammonium bicarbonate adjusted to pH 10 with ammonia solution.
B=acetonitrile.
The gradient employed was:

| Time (min) | Flow Rate (mL/min) | % A | % B |
|---|---|---|---|
| 0 | 40 | 85 | 15 |
| 1 | 40 | 85 | 15 |
| 10 | 40 | 45 | 55 |
| 11 | 40 | 1 | 99 |
| 15 | 40 | 1 | 99 |

Preparation of Intermediates

Intermediate 1: (R)-tert-butyl 3-(iodomethyl) pyrrolidine-1-carboxylate

A 5 L vacuum-jacketed glass reaction vessel (Radley's LARA) was charged with DCM (2 L), followed by triphenylphosphine (339 g, 1.29 mol) and imidazole (88 g, 1.29 mol), and the temperature was reduced to 0° C. Iodine (328 g, 1.29 mol) was then added portionwise over 30 min whilst maintaining the reaction temperature at between 0-5° C. to control the exotherm. During the addition, a thick brown precipitate formed. The precipitate was allowed to warm to room temperature over 15 min and was then stirred at room temperature for a further 30 min. A solution of (R)-tert-butyl 3-(hydroxymethyl pyrrolidine-1-carboxylate (200 g, 994 mmol) (available from Fluorochem or BePharm Ltd) in DCM (200 mL) was added portionwise over 15 min, whilst maintaining the reaction temperature between 24-30° C. The reaction mixture was stirred for 2 h, then diluted with TBME (8 L), and filtered. The filtrate was concentrated under reduced pressure, and the residue (700 g) was triturated in diethyl ether (2 L) in an ice-water bath to give 333 g of crude product. A 27 g portion of the crude product was purified by chromatography on a silica cartridge (100-g) eluting with a gradient of 0-50% ethyl acetate-cyclohexane over 30 min. The appropriate fractions were combined and evaporated in vacuo to give the title compound (16.33 g, 5%) as a yellow oil. The remaining crude material (~306 g) was purified by chromatography on a silica cartridge (1.5 kg) eluting with a gradient of 0-30% ethyl acetate-cyclohexane over 9.5 column volumes. The appropriate fractions were combined and evaporated in vacuo to give the title compound (233.94 g, 76%) as a pale yellow oil: LCMS (System A) RT=1.19 min, 100%, ES+ve m/z 312 (M+H)$^+$; $[\alpha]_D^{20}$=+23 (c 1.00 in EtOH).

Intermediate 2: (R)-tert-Butyl 3-(2-(1, 8-naphthyridin-2-yl) ethyl) pyrrolidine-1-carboxylate A stirred solution of 2-methyl-1,8-naphthyridine (57.5 g, 399 mmol) (available from Manchester Organics) and (R)-tert-butyl 3-(iodomethyl)pyrrolidine-1-carboxylate (124.2 g, 399 mmol) (Intermediate 1) in THF (1 L) was cooled to 0° C. and treated under nitrogen with a solution of lithium bis(trimethylsilyl)amide in THF (1M, 399 mL, 399 mmol) over 20 min and the reaction mixture was stirred at 0° C. for 3 h. The reaction was quenched with saturated ammonium chloride solution (500 mL) and water (500 mL) and ethyl acetate (1 L) was added. The layers were separated and the aqueous phase was extracted with further ethyl acetate (1 L). The combined organic layers were dried (MgSO$_4$), filtered and evaporated in vacuo. The residual brown oil (162 g) was purified by chromatography on a silica cartridge (750 g) eluting with a gradient of 0-100% [ethyl acetate in (5% MeOH-95% ethyl acetate)] over 8 column volumes. The appropriate fractions were combined and evaporated in vacuo to give the title compound (46.65 g, 36%) as an orange solid: LCMS (System A) RT=0.99 min, 97%, ES+ve m/z 328 (M+H)$^+$, $[\alpha]_D^{20}$=+22 (c 1.00 in EtOH).

Intermediate 3. (R)-tert-butyl 3-(2-(5, 6, 7, 8-tetrahydro-1, 8-naphthyridin-2-yl) ethyl) pyrrolidine-1-carboxylate A solution of (R)-tert-butyl 3-(2-(1,8-naphthyridin-2-yl) ethyl)pyrrolidine-1-carboxylate (Intermediate 2) (4.0 g, 12 mmol) in EtOH (20 mL) was hydrogenated over wet 5% Rh/C catalyst (1.2 g) at room temperature overnight. The catalyst was collected by filtration through celite and the filtrate was concentrated in vacuo to give the title compound (4.0 g, 99%) as a brown gum: LCMS (System A) RT=1.20 min, 95.5%, ES+ve m/z 332 (M+H)$^+$.

Intermediate 4. (R)-7-(2-(pyrrolidin-3-yl) ethyl)-1, 2, 3, 4-tetrahydro-1, 8-naphthyridine To a solution of (R)-tert-butyl 3-(2-(5, 6, 7, 8-tetrahydro-1, 8-naphthyridin-2-yl) ethyl) pyrrolidine-1-carboxylate (Intermediate 3) (18.92 g, 57.1 mmol) in DCM (120 mL) in a cold water bath under nitrogen was added dropwise 4M HCl in 1, 4-dioxane (57.1 mL, 228 mmol). Once addition was complete, the water bath was removed. The reaction was left to stir at room temperature overnight and then concentrated in vacuo. The residue (15.5 g) was purified in several batches on SCX cartridges washing first with methanol and then eluting with 2M ammonia in methanol to give the title compound (8.94 g, 68%) as an orange oil: LCMS (System A) RT=0.70 min, 100% ES+ve m/z 232 (M+H)$^+$.

Intermediate 5. (R, E)-methyl 4-(3-(2-(5, 6, 7, 8-tetrahydro-1, 8-naphthyridin-2-yl) ethyl) pyrrolidin-1-yl) but-2-enoate A solution of (R)-7-(2-(pyrrolidin-3-yl) ethyl)-1, 2, 3, 4-tetrahydro-1, 8-naphthyridine (Intermediate 4) (10.6 g, 45.8 mmol) in DCM (200 mL) was added DIPEA (14.40 mL, 82 mmol) under nitrogen.

The reaction mixture was cooled to 0° C. and (E)-methyl 4-bromobut-2-enoate (5.39 mL, 45.8 mmol) was added dropwise. The reaction was stirred at room temperature for 3.75 h and then the reaction mixture was diluted with water (250 mL). The organic layer was separated and the aqueous layer was further extracted with DCM (2×100 mL). The combined organic fractions were dried (MgSO$_4$) and evaporated in vacuo. The residue (13.94 g) was purified by chromatography on a silica cartridge (330 g) eluting with 0-100% EtOAc-(3:1 EtOAc-EtOH) containing 1% Et$_3$N.

Appropriate fractions were combined and evaporated to give the title compound (7.66 g, 51%) as a yellow oil, which solidified on storage in the fridge. LCMS (System A) RT=1.02 min, 100%, ES+ve m/z 330 (M+H)$^+$.

Intermediate 6. Methyl 3-(3-bromophenyl)-4-((R)-3-(2-(5,6,7,8-tetrahydro-1,8-naphthyridin-2-yl)ethyl) pyrrolidin-1-yl)butanoate A solution of (R,E)-methyl 4-(3-(2-(5,6,7,8-tetrahydro-1, 8-naphthyridin-2-yl)ethyl)pyrrolidin-1-yl)but-2-enoate (Intermediate 5) (2.8 g, 8.5 mmol) in 1,4-dioxane (60 mL) was treated with (3-bromophenyl)boronic acid (available from Aldrich) (5.97 g, 29.7 mmol), (R)-BINAP (0.529 g, 0.850 mmol), aqueous solution KOH (3.8M, 4.47 mL, 17.00 mmol) and chloro(1,5-cyclooctadiene)rhodium(I) dimer (210 mg, 0.425 mmol) and the mixture was heated at 95° C. for 1 h. The reaction mixture was allowed to cool down and concentrated in vacuo. The residue was partitioned between water (50 mL) and DCM (50 mL). To the aqueous fractions, brine (50 mL) was added and extracted with more DCM (50 mL). The combined organic solutions were washed with brine (50 mL), passed through hydrophobic frit and concentrated in vacuo. The residue was purified by chromatography on aminopropyl column (70 g) eluting with a gradient of 0-100% EtOAc-cyclohexane and then by reverse phase chromatography on a Biotage SNAP cartridge (120 g) eluting with a gradient of 65-95% acetonitrile-(10 mM aqueous ammonium bicarbonate adjusted to pH 10 with ammonia solution). Appropriate fractions were combined and concentrated in vacuo to afford (400 mg) of the title compound as a diastereoisomeric mixture. LCMS (System A) RT=1.39 min, ES+ve m/z 486, 488 (M+H)$^+$. The diastereoisomers were separated by preparative chiral HPLC on Chiralcel OJ-H column (30 mm×25 cm) eluting with 20% EtOH (containing 0.2% isopropylamine)-heptane, flow rate 30 mL/min, detecting at 215 nm. Appropriate fractions were combined and evaporated to give the title compound:

Isomer 1
(S)-methyl 3-(3-bromophenyl)-4-((R)-3-(2-(5,6,7,8-tetrahydro-1,8-naphthyridin-2-yl)ethyl)pyrrolidin-1-yl)butanoate (650 mg, 16%): LCMS (System B) RT=0.46 min, ES+ve m/z 486, 488 (M+H)$^+$. Analytical chiral HPLC RT=17.9 min on Chiralcel OJ-H column (4.6 mm id×25 cm) eluting with 20% EtOH (containing 0.2% isopropylamine)-heptane flow rate 1 mL/min, detecting at 215 nm.

Isomer 2
(R)-methyl 3-(3-bromophenyl)-4-((R)-3-(2-(5,6,7,8-tetrahydro-1,8-naphthyridin-2-yl)ethyl)pyrrolidin-1-yl)butanoate (103 mg, 2%): Analytical chiral HPLC RT=14.3 min on Chiralcel OJ-H column (4.6 mm id×25 cm) eluting with 20% EtOH (containing 0.2% isopropylamine)-heptane flow rate 1 mL/min, detecting at 215 nm.

Intermediate 7. 1-(3-bromophenyl)-1H-imidazole

A stirred suspension of 1-bromo-3-iodobenzene (available from Apollo) (2.252 mL, 17.67 mmol), 1H-imidazole (2.166 g, 31.8 mmol), copper(I) iodide (0.673 g, 3.53 mmol) and caesium carbonate (11.52 g, 35.3 mmol) in MeCN (70 mL) was degassed (3 times) and then was refluxed overnight under nitrogen. The reaction mixture was allowed to cool down to room temperature, filtered and the filtrate was concentrated in vacuo. The residue was purified by chromatography on a KP-silica cartridge (100 g) eluting with 0-100% EtOAc-cyclohexane. The appropriate fractions were combined and concentrated in vacuo to give the title compound (3.55 g, 90%) as a colourless oil: LCMS (System C) RT=0.92 min, 99%, ES+ve m/z 223, 225 (M+H)$^+$.

Intermediate 8. 1-(3-(4, 4, 5, 5-tetramethyl-1, 3, 2-dioxaborolan-2-yl) phenyl)-1H-imidazole To a solution of 1-(3-bromophenyl)-1H-imidazole (Intermediate 7) (1.0 g, 4.5 mmol) in 1,4-dioxane (25 mL), bis(pinacolato)diboron (available from Aldrich) (1.25 g, 4.93 mmol), dicyclohexyl-(2',4',6'-triisopropyl-[1,1'-biphenyl]-2-yl)phosphine (0.103 g, 0.215 mmol), Pd$_2$dba$_3$ (0.062 g, 0.067 mmol), potassium acetate (1.1 g, 11 mmol) were added. The reaction mixture was heated at 110° C. The reaction was concentrated in vacuo and kept in the freezer over the weekend. The residue was partitioned between DCM (50 mL) and water (50 mL). Brine (30 mL) was added to the aqueous layer, and further extracted with DCM (30 mL). The combined organic fractions were washed with brine (30 mL), passed through a hydrophobic frit and concentrated in vacuo. The residue was purified by reverse phase chromatography on C18 Biotage SNAP cartridge (60 g) eluting with 30-60% acetonitrile (containing 0.1% formic acid)-water (containing 0.1% formic acid) (6 CV). The appropriate fractions were combined and concentrated in vacuo to afford the title compound (594 mg, 49%) as a pale yellow gum: LCMS (System D) RT=0.33 min, ES+ve m/z 189 (M+H)$^+$.

Intermediate 9. (1-(3-bromophenyl)-5-methyl-1H-pyrazol-3-yl)methanol

To a stirred solution of ethyl 1-(3-bromophenyl)-5-methyl-1H-pyrazole-3-carboxylate (reported in WO02004092140) (500 mg, 1.62 mmol) in THF (10 mL) was added DIBAL-H (1M solution in THF) (7.12 mL, 7.12 mmol) at 0° C. and the resulting mixture was stirred at ambient temperature for 16 h. The reaction mixture was quenched with water (10 mL) and diluted with ethyl acetate (10 mL). The organic phase was concentrated and the residue was purified by column chromatography on silica gel (100-200 mesh) eluting with 50% ethyl acetate in hexane to afford the title compound (300 mg, 66%) as an off-white solid: $^1$H NMR (400 MHz, CDCl$_3$) 7.65 (1H, s), 7.50 (1H, d, J 7.5 Hz), 7.42-7.35 (2H, m), 6.20 (1H, s), 4.68 (2H, m), 2.35 (3H, s).

Intermediate 10. (5-methyl-1-(3-(4,4,5,5-tetramethyl-1,3,2-dioxaborolan-2-yl)phenyl)-1H-pyrazol-3-yl)methanol To a stirred solution of (1-(3-bromophenyl)-5-methyl-1H-pyrazol-3-yl)methanol (Intermediate 9) (4.0 g, 15 mmol), bis(pinacolato)diboron (3.8 g, 15 mmol), potassium acetate (4.41 g, 45 mmol) in 1,4-dioxane (40 mL) was added PdCl$_2$(dppf)-CH$_2$Cl$_2$ adduct (1.22 g, 1.5 mmol) and resulting mixture was stirred at 90° C. for 6 h. The reaction mixture was cooled to room temperature and filtered through a celite bed. The filtrate was concentrated under vacuum and the residue was dissolved in ethyl acetate (100 mL) and filtered through celite. The filtrate was concentrated under vacuum and the residue was purified by column chromatography on florisil silica eluting with a gradient of 0-5% ethyl acetate in petroleum ether. Appropriate fractions were concentrated under vacuum to afford the title compound (1.4 g, 23%) as a brown oil: MS ES+ve m/z 315 (M+H)$^+$.

Intermediate 11.
1-(3-bromophenyl)-3,5-dimethyl-1H-1,2,4-triazole

N-acetylacetamide (2.0 g, 20 mmol), (3-bromophenyl) hydrazine hydrochloride (8.84 g, 39.6 mmol) and pyridine (4 mL) were placed in a 30 ml microwave vial (Anton Paar). The vial was irradiated for 2 min (300 W, 200° C.) with stirring. Ethyl acetate (15 mL) was added to the reaction mixture to precipitate residual hydrazine hydrochloride, and then filtered. The filtrate was concentrated under reduced pressure and the residue was purified by column chromatography on silica gel eluting with 15% EtOAc-hexanes to give the title compound (2.4 g, 43%) as a pale yellow solid: $^1$H NMR (400 MHz, CDCl$_3$) 7.65 (1H, br s), 7.55 (1H, m), 7.38-7.34 (2H, m), 2.50 (3H, s), 2.41 (3H, s).

Intermediate 12. 3,5-dimethyl-1-(3-(4,4,5,5-tetramethyl-1,3,2-dioxaborolan-2-yl)phenyl)-1H-1,2,4-triazole was prepared from Intermediate 11 (1.5 g, 5.9 mmol) by a similar method to the one described for Intermediate 10 to give the title compound (936 mg, 37%): MS ES+ve m/z 300 (M+H)+.

Intermediate 13.
4-(3-bromophenyl)-3-methyl-4H-1,2,4-triazole

A mixture of (3-bromophenyl)boronic acid (available from Apollo Scientific) (9.43 g, 46.9 mmol), 3-methyl-4H-1,2,4-triazole (available from Chemimpex) (3.0 g, 36 mmol), Cs$_2$CO$_3$ (23.53 g, 72.2 mmol), copper (I) iodide (688 mg, 3.61 mmol) in DMF (30 mL) was sealed in a tube and heated to 100° C. for 16 h. Reaction was diluted with water (150 mL) and extracted with EtOAc (3×50 mL). The organic layer was washed with water (2×50 mL), dried (Na$_2$SO$_4$) and evaporated in vacuo. The residue was purified by Prep TLC eluting with 20% EtOAc-hexane to give the title compound (1.3 g, 15%) as a white solid. TLC R$_F$=0.5 (Mobile Phase: 30% EtOAc-hexane).

Intermediate 14. 3-methyl-4-(3-(4,4,5,5-tetramethyl-1,3,2-dioxaborolan-2-yl)phenyl)-4H-1,2,4-triazole was prepared from Intermediate 13 (1.2 g, 5 mmol) by a similar method to the one described for Intermediate 10 to give the title compound (700 mg, 44%): MS ES+ve m/z 286 (M+H)+.

Intermediate 15. 2-(1-(3-bromophenyl)-5-methyl-1H-pyrazol-3-yl)propan-2-ol

A suspension of ethyl 1-(3-bromophenyl)-5-methyl-1H-pyrazole-3-carboxylate (reported in WO2004092140) (3.1 g, 10.03 mmol) in THF (7 mL) was treated dropwise with methyl magnesium bromide (60.2 mL, 60.2 mmol) at 0° C. and stirred for 2 h. The reaction mixture was treated dropwise with 1M KHSO$_4$ (20 mL) and concentrated under reduced pressure. The residue was dissolved in ethyl acetate and washed with water (20 mL). The organic layer was concentrated under reduced pressure and purified by column chromatography on silica gel (100-200) eluting with 15% ethyl acetate in petroleum. ether. The appropriate fractions were concentrated under reduced pressure to give the title compound (2.45 g, 79%) as a pale yellow liquid: MS ES+ve m/z 295 (M+H)$^+$.

Intermediate 16. 2-(5-methyl-1-(3-(4,4,5,5-tetramethyl-1,3,2-dioxaborolan-2-yl)phenyl-1H-pyrazol-3-yl)propan-2-ol was prepared from Intermediate 15 (300 mg, 1 mmol) by a similar method to the one described for Intermediate 10 to give the title compound (120 mg, 32%): MS ES+ve m/z 343 (M+H)$^+$.

Intermediate 17.
1-(3-bromophenyl)-3-(trifluoromethyl)-1H-pyrazole

A mixture of 1-bromo-3-iodobenzene (available from Apollo Scientific) (1.351 mL, 10.60 mmol), 3-(trifluoromethyl)-1H-pyrazole (available from Aldrich) (2.164 g, 15.91 mmol), Cs$_2$CO$_3$ (10.37 g, 31.8 mmol) and CuI (404 mg, 2.121 mmol) in acetonitrile (28 mL) was heated to 106° C. The reaction mixture was allowed to cool to room temperature and filtered. The filtrate was concentrated in vacuo and the residue was purified by chromatography on a silica column (100 g) eluting with 0-100% EtOAc-cyclohexane to give the title compound (2.67 g, 87%) as a pale yellow oil: LCMS (System C) RT=1.37 min, 96%, ES+ve m/z 291, 293 (M+H)+; $^1$H NMR (600 MHz, DMSO-d$_6$) δ 8.75 (dd, J 2.6, 1.1 Hz, 1H), 8.10-8.05 (m, 1H), 7.88 (ddd, J 8.3, 2.2, 0.9 Hz, 1H), 7.56-7.50 (m, 1H), 7.44 (t, J 8.1 Hz, 1H), 6.97 (d, J 2.9 Hz, 1H).

Intermediate 18. 1-(3-(4,4,5,5-tetramethyl-1,3,2-dioxaborolan-2-yl)phenyl)-3-(trifluoromethyl)-1H-pyrazole To a solution of 1-(3-bromophenyl)-3-(trifluoromethyl)-1H-pyrazole (Intermediate 17) (1.32 g, 4.54 mmol) in 1,4-dioxane (24 mL), dicyclohexyl(2',4',6'-triisopropyl-[1,1'-biphenyl]-2-yl)phosphine (0.104 g, 0.218 mmol), Pd$_2$dba$_3$ (62 mg, 0.068 mmol), potassium acetate (1.113 g, 11.34 mmol) and 4,4,4',4',5,5,5',5'-octamethyl-2,2'-bi(1,3,2-dioxaborolane) (1.267 g, 4.99 mmol) were added. The reaction mixture was refluxed at 110° C. for 3 h. After cooling, the reaction mixture was concentrated in vacuo and the residue was partitioned between water (30 mL) and EtOAc (30 mL). Brine (30 mL) was added to the aqueous fraction and this was further extracted with EtOAc (40 mL). The combined organic fractions were washed with brine (30 mL), passed through hydrophobic frit and concentrated in vacuo. The residue was purified by reverse phase column chromatography on C18 Biotage SNAP cartridge (60 g) eluting with 40-85% MeCN-10 mM ammonium bicarbonate (containing 0.1% ammonia) (14 CV). The appropriate fractions were combined and concentrated in vacuo to afford the title compound (700 mg): LCMS (System D) RT=1.49 min, ES+ve m/z 339 (M+H)+.

Intermediate 19. 4-(3-(4,4,5,5-tetramethyl-1,3,2-dioxaborolan-2-yl)phenyl)-4H-1,2,4-triazole was prepared from 4-(3-bromophenyl)-4H-1,2,4-triazole (available from Fluorochem) (3.0 g, 13 mmol), in a similar way to the method described for the preparation of Intermediate 10 to give the title compound (1.3 g, 36%) as a white solid: $^1$H NMR (400 MHz, DMSO-d$_6$) 9.13 (2H, s), 7.84-7.80 (2H, m), 7.58 (1H, br d, J 7.5 Hz), 7.59 (1H, br t, J 7.5 Hz), 1.32 (12H, s).

Intermediate 20.
1-(3-bromophenyl)-1H-1,2,3-triazole

A solution of 1,3-dibromobenzene (20 g, 85 mmol) in DMF (200 mL) was treated with 1H-1,2,3-triazole (6.97 g, 101 mmol), copper (I) iodide (1.62 g, 8.48 mmol), Fe (III) acetyl acetonate (6.78 g, 25.4 mmol) and Cs$_2$CO$_3$ (55.2 g, g, 170 mmol). The reaction mixture was heated at 120° C. for 18 h, filtered through celite and washed with EtOAc (3×200 mL), and concentrated under reduced pressure. The residue was purified by column chromatography on silica gel eluting with 20% EtOAc in hexane. Appropriate fractions were concentrated under reduced pressure to afford the title compound (4 g, 17%) as a pale yellow solid: MS ES+ve m/z 224, 226 (M+H)+.

Intermediate 21. 1-(3-(4,4,5,5-tetramethyl-1,3,2-dioxaborolan-2-yl)phenyl)-1H-1,2,3-triazole was prepared from 1-(3-bromophenyl)-1H-1,2,3-triazole (Intermediate 20) by a method similar to that described for Intermediate 10 to give the title compound (1.5 g, 30%) as a white solid: MS ES+ve m/z 272 (M+H)+.

Intermediate 22. (RE)-tert-butyl 7-(2-(1-(4-methoxy-4-oxobut-2-en-1-yl)pyrrolidin-3-yl)ethyl)-3,4-dihydro-1,8-naphthyridine-1(2H)-carboxylate A solution of Intermediate 5 (270 mg, 0.820 mmol) and di-tert-butyl dicarbonate (247 μL, 1.065 mmol) in THF at 0° C. under nitrogen was treated dropwise with LHMDS (1065 μL, 1.065 mmol) during 5 min. The solution was stirred at 0° C. for 30 min. The solution was treated with aqueous NH$_4$Cl (10%, 5 mL) and extracted with 2-MeTHF (5 mL). The organic phase was directly applied to a silica cartridge (10 g) eluted with toluene-ethanol-ammonia (80-10-1) to give the title compound (302 mg, 86%) as a yellow gum: LCMS (System C) RT=1.27 min, ES+ve m/z 430 (M+H)+.

Intermediate 23. Mixture of tert-butyl 7-(2-((R)-1-((S)-2-(3-(3-(hydroxymethyl)-5-methyl-1H-pyrazol-1-yl)phenyl)-4-methoxy-4-oxobutyl)pyrrolidin-3-yl)ethyl)-3,4-dihydro-1,8-naphthyridine-1(2H)-carboxylate and tert-butyl 7-(2-((R)-1-((R)-2-(3-(3-(hydroxymethyl)-5-methyl-1H-pyrazol-1-yl)phenyl)-4-methoxy-4-oxobutyl)pyrrolidin-3-yl)ethyl)-3,4-dihydro-1,8-naphthyridine-1(2H)-carboxylate-(9:1)

A solution of (5-methyl-1-(3-(4,4,5,5-tetramethyl-1,3,2-dioxaborolan-2-yl)phenyl)-1H-pyrazol-3-yl)methanol (Intermediate 10) (549 mg, 1.746 mmol) in dioxane (1 mL) was treated with KOH aqueous (0.404 mL, 1.536 mmol) followed by a solution of (R,E)-tert-butyl 7-(2-(1-(4-methoxy-4-oxobut-2-en-1-yl)pyrrolidin-3-yl)ethyl)-3,4-dihydro-1,8-naphthyridine-1(2H)-carboxylate (Intermediate 22) (300 mg, 0.698 mmol) in dioxane (1 mL). The solution was degassed under nitrogen/vacuum and was treated with R-BINAP (43.5 mg, 0.070 mmol) and chloro(1,5-cyclooctadiene)rhodium(I) dimer (17.22 mg, 0.035 mmol). The mixture was again degassed under nitrogen/vacuum and was heated at 50° C. for 3 h. The cooled mixture was added to water/brine (30 mL; 1:1) and extracted with EtOAc (2×25 mL). The dried (MgSO$_4$) extract was evaporated and the residue was purified on a silica cartridge (20 g) eluted with 0-100% [(3:1) EtOAc-isopropanol]-EtOAc to give the title compound (205 mg, 47%) as a pale brown gum. Stereoisomer ratio at benzylic centre is not evident from NMR, but can be determined from the deprotected material (Example 10) as 9:1: LCMS (System C) RT=1.30 min, ES+ve m/z 618 (M+H)+.

Intermediate 24. tert-Butyl 7-(2-((3R)-1-(2-(3-(3-(fluoromethyl)-5-methyl-1H-pyrazol-1-yl)phenyl)-4-methoxy-4-oxobutyl)pyrrolidin-3-yl)ethyl)-3,4-dihydro-1,8-naphthyridine-1(2H)-carboxylate (9:1 mixture of Isomer 1:Isomer 2)

A solution of methanesulfonyl chloride (0.018 mL, 0.227 mmol) in DCM (0.1 mL) was added to a solution of tert-butyl 7-(2-((3R)-1-(2-(3-(3-(hydroxymethyl)-5-methyl-1H-pyrazol-1-yl)phenyl)-4-methoxy-4-oxobutyl)pyrrolidin-3-yl)ethyl)-3,4-dihydro-1,8-naphthyridine-1(2H)-carboxylate (Intermediate 23) (140 mg, 0.227 mmol) and triethylamine (0.063 mL, 0.453 mmol) in DCM (1.5 mL). The solution was stirred for 1 h and analysis shows mostly complete with evidence for partial chloride replacement for mesyl. The solution was treated with acetonitrile (2 mL), potassium fluoride (13.17 mg, 0.227 mmol) and Kryptofix™ (5,6-benzo-4,7,13,16,21,24-hexaoxa-1,10-diazabicyclo [8.8.8]hexacos-5-ene) (85 mg, 0.227 mmol) and heated to 60° C. for 1 h. Analysis shows only chloride present, and no fluoro displacement. The mixture was partitioned between aq NaHCO$_3$ (5 mL) and EtOAc (2×5 mL) and the dried (MgSO$_4$) extract was evaporated. The residue was dissolved in DMF (1.5 mL) was treated with 4 equivalents of KF and Kryptofix™ and heated in a sealed microwave vessel at 120° C. for 30 min. The solution was added to water (10 mL) and extracted with EtOAc (2×5 mL). The dried (MgSO$_4$) extract was evaporated and the residue was taken directly to the next step (Example 11): LCMS (System C) RT=1.46 min, ES+ve m/z 620 (M+H)+.

Intermediate 25.
2-(3-bromophenyl)-4-methyl-1H-imidazole

A solution of 3-bromobenzimidamide (available from Fluorochem) (22 g, 111 mmol), 1-chloropropan-2-one (16.36 g, 177 mmol) and ammonium chloride (21.88 g, 409 mmol) in THF (200 mL) was treated under nitrogen with ammonium hydroxide (176 mL, 4532 mmol) and the reaction mixture was stirred at 80° C. for 12 h. The reaction mixture was concentrated in vacuo and the residue (11.5 g) was purified by column chromatography on silica gel (100-200 mesh) eluting with 30% ethyl acetate in petroleum ether. The appropriate fractions were concentrated and the resulting pale yellow solid was triturated in diethyl ether to afford the title compound (5.2 g, 20%) as a brown solid: $^1$H NMR (400 MHz, CDCl$_3$) 9.2 (1H, br), 7.95 (1H, s), &70 (1H, d), 7.42 (1H, d), 7.27 (1H, m), 6.83 (1H, s), 2.35 (3H, s).

Intermediate 26.
2-(3-bromophenyl)-1,4-dimethyl-1H-imidazole

A solution of 2-(3-bromophenyl)-4-methyl-1H-imidazole (Intermediate 25) (5 g, 21 mmol) and potassium tert-butoxide (2.366 g, 21.09 mmol) in THF (100 mL) was treated with a solution of 18-crown-6 (0.557 g, 2.109 mmol) and iodomethane (1.319 mL, 21.09 mmol) in THF (20 mL) and the mixture was stirred at room temperature for 16 h. Reaction mixture was poured into brine solution and extracted with ethyl acetate (100 mL). The organic phase was separated, dried (Na$_2$SO$_4$) and concentrated in vacuo. The residue (5.2 g) was purified by column chromatography on silica gel (100-200) eluting with 20% ethyl acetate in petroleum ether. Appropriate fractions were evaporated to afford the title compound (2.0 g, 38%) as pale yellow liquid: 1H NMR (400 MH, DMSO-d$_6$) 7.85 (1H, s), 7.69 (1H, d, J 7.5 Hz), 7.60 (1H, d, J 7.5 Hz), 7.40 (1H, t, J 7.5 Hz), 6.97 (1H, s), 3.70 (3H, s), 2.15 (3H, s).

Intermediate 27. 1,4-dimethyl-2-(3-(4,4,5,5-tetramethyl-1,3,2-dioxaborolan-2-ylphenyl)-1H-imidazole The title compound was prepared from Intermediate 26 (1 g, 4 mmol) by a process similar to that described for Intermediate 8 to give (420 mg, 83%): $^1$H NMR (400 MHz, CDCl$_3$) 8.04 (1H, br s), 7.82 (1H, br d, J 7.5 Hz), 7.70 (1H, br d, J 7.5 Hz), 7.45 (1H, t, J 7.5 Hz), 6.66 (1H, s), 3.66 (3H, s), 2.26 (3H, s), 1.35 (12H, s).

Intermediate 28.
5-(3-Bromophenyl)-2,4-dimethyl-1H-imidazole

To a solution of (E)-1-bromo-3-(2-nitroprop-1-en-1-yl) benzene (U. Jana et. al. *Europ. J. Org. Chem.* 2013, (22), 4823) (20 g, 83 mmol) in ethanol (200 mL) was added acetamidine hydrochloride (7.81 g, 83 mmol), potassium carbonate (11.42 g, 83 mmol) and indium(III)oxide (1.147 g, 4.13 mmol) and the reaction was stirred under nitrogen at 70° C. for 6 h. The reaction was monitored by TLC.
TLC Mobile Phase: 10% MeOH in DCM, Rf Value: 0.5, Detection: UV. Workup: Ethanol was removed under reduced pressure. The crude reaction mixture was diluted with water (150 mL) and extracted with EtOAc (3×200 mL), washed with brine solution (250 mL). The organic layer was separated, dried (Na$_2$SO$_4$) and concentrated under reduced pressure. The residue was triturated in diethyl ether (50 mL), the solid was collected by filtration and dried to afford the title compound (4.4 g, 21%) as a white solid ES+ve m/z 251, 253 (M+H)$^+$.

Intermediate 29 tert-Butyl 5-(3-bromophenyl)-2,4-dimethyl-1H-imidazole-1-carboxylate A suspension of 5-(3-bromophenyl)-2,4-dimethyl-1H-imidazole (4 g, 16 mmol) (Intermediate 28) in DCM (40 mL) was treated with TEA (5.55 mL, 39.8 mmol), di-tert-butyl dicarbonate (5.55 mL, 23.9 mmol), DMAP (0.195 g, 1.593 mmol) at 0° C. and the mixture was stirred under nitrogen. The mixture was stirred at room temperature for 2 h, diluted with DCM and washed with water, citric acid solution, brine, dried (Na$_2$SO$_4$), filtered and concentrated under reduced pressure. The residue was purified by column chromatography to give the title compound analysis. LCMS: ES+ve m/z 351 (M+H)$^+$.

Intermediate 30. tert-Butyl 2,4-dimethyl-5-(3-(4,4,5,5-tetramethyl-1,3,2-dioxaborolan-2-yl)phenyl)-1H-imidazole-1-carboxylate To a stirred solution of tert-butyl 5-(3-bromophenyl)-2,4-dimethyl-1H-imidazole-1-carboxylate (4.5 g, 12.8 mmol) in 1,4-dioxane (50 mL) was added potassium acetate (2.51 g, 25.6 mmol) and 4,4,4',4',5,5,5',5'-octamethyl-2,2'-bi(1,3,2-dioxaborolane) (3.90 g, 15.37 mmol). The solution was purged with argon gas for 15 min. 1,1'-bis(diphenylphosphino)ferrocenedichloro palladium(II) dichloromethane complex (0.937 g, 1.281 mmol) was added. Again purged with Argon gas for 15 min. The reaction mixture was stirred at 90° C. for 16 h. The reaction mixture was filtered through a celite bed, washed with EtOAc (3×100 mL), and concentrated under reduced pressure. The residue was purified by column chromatography on silica gel eluting with 10% EtOAc in hexane. The required fractions were concentrated under reduced pressure to afford the title compound (4.0 g, 78%) as a white solid: LCMS ES+ve m/z 399 (M+H)$^+$.

Intermediate 31. 2,4-Dimethyl-5-(3-(4,4,5,5-tetramethyl-1,3,2-dioxaborolan-2-yl)phenyl)-1H-imidazole A solution of tert-butyl 2,4-dimethyl-5-(3-(4,4,5,5-tetramethyl-1,3,2-dioxaborolan-2-yl)phenyl)-1H-imidazole-1-carboxylate (Intermediate 30) (3.9 g, 9.79 mmol) in 1,4-dioxane (40 mL) was cooled under nitrogen to 0° C. and then treated with dropwise with 4M HCl in 1,4-dioxane (40 mL) over 10 min. The reaction mixture was stirred at room temperature for 16 h. The solvent was removed under reduced pressure and the residue was treated with diethyl ether (50 mL). The resulting solid was collected by filtration and washed with diethyl ether (50 mL). The solid was dissolved in DCM (200 mL) and washed with NaHCO$_3$ solution (100 mL). The organic layer was separated, dried (Na$_2$SO$_4$) and concentrated under reduced pressure. The residue was triturated with pentane (50 mL) to afford the title compound (1.27 g, 37%) as white solid: LCMS ES+ve m/z 299 (M+H)$^+$.

Intermediate 32. Methyl 3-(3-(2,4-dimethyl-1H-imidazol-5-yl)phenyl)-4-((R)-3-(2-(5,6,7,8-tetrahydro-1,8-naphthyridin-2-yl)ethyl) pyrrolidin-1-yl) butanoate A mixture of 2,4-dimethyl-5-(3-(4,4,5,5-tetramethyl-1,3,2-dioxaborolan-2-yl)phenyl)-1-imidazole (Intermediate 31) (543 mg, 1.821 mmol), (R,E)-methyl 4-(3-(2-(5,6,7,8-tetrahydro-1,8-naphthyridin-2-yl)ethyl)pyrrolidin-1-yl)but-2-enoate (Intermediate 5) (200 mg, 0.607 mmol), (R)-BINAP (41.6 mg, 0.067 mmol) and bis(norbornadiene)rhodium(I) tetrafluoroborate (22.70 mg, 0.061 mmol) were added to a microwave vial. These were dissolved in 1,4-dioxane (10 mL) followed by addition of 3.8M KOH solution (0.320 mL, 1.21 mmol). The reaction mixture was immediately heated at 95° C. for 45 min using the Biotage microwave system.

The sample was diluted with MeOH and loaded onto an SCX column (10 g). This was washed with MeOH (2 CV) and then eluted using 2M $NH_3$ in MeOH. The solvent was removed under reduced pressure and the residue (504 mg) was dissolved in 1:1 DMSO:MeOH and loaded onto a reverse phase (C18) column (12 g), and eluted using a 30-85% gradient of 10 mM aq. ammonium bicarbonate solution-MeCN over 12CV. The appropriate fractions were combined and the solvent evaporated under reduced pressure to afford the title compound as a mixture of diastereoisomers (101 mg, 33%). LCMS (System C) RT=1.16 min, 95%, ES+ve m/z 502 (M+H)+. The isomers were separated by preparative chiral HPLC on a Chiralpak IC column (250 mm×30 mm) eluting with 10% EtOH containing 0.2% isopropylamine-heptane flow-rate 30 mL/min, detecting at 215 nm to give:

Isomer 1

(2 mg)) [(R)-methyl 3-(3-(2,4-dimethyl-1H-imidazol-5-yl)phenyl)-4-((R)-3-(2-(5,6,7,8-tetrahydro-1,8-naphthyridin-2-yl)ethyl)pyrrolidin-1-yl)butanoate]. Anal. Chiral HPLC RT=26.3 min, 100% on Chiralpak IC column (250 mm×4.6 mm) eluting with 10% EtOH containing 0.2% isopropylamine-heptane, flow-rate=1 mL/min, detecting at 215 nm.

Isomer 2

(18 mg) [(S)-methyl 3-(3-(2,4-dimethyl-1H-imidazol-5-yl)phenyl)-4-((R)-3-(2-(5,6,7,8-tetrahydro-1,8-naphthyridin-2-yl)ethyl)pyrrolidin-1-yl)butanoate]. Anal. Chiral HPLC RT=29.4 min, 100% on Chiralpak IC column (250 mm×4.6 mm) eluting with 10% EtOH containing 0.2% isopropylamine-heptane, flow-rate=1 mL/min, detecting at 215 nm.

Intermediate 33. 1-(3-(4,4,5,5-tetramethyl-1,3,2-dioxaborolan-2-yl)phenyl)-1H-1,2,4-triazole To a solution of 1-(3-bromophenyl)-1H,1,2,4-triazole (WO2001090108, page 62) (27 g, 121 mmol) in 1,4-dioxane (600 mL) was added 4,4,4',4',5,5,5',5'-octamethyl-2,2'-bi(1,3,2-dioxaborolane) (30.6 g, 121 mmol) and potassium acetate (23.65 g, 241 mmol) and the reaction mixture was stirred for 15 min before $PdCl_2(dppf)$-$CH_2Cl_2$ adduct was added (9.84 g, 12.05 mmol). The mixture was heated to 100° C. for 18 h, then was allowed to cool to room temperature and filtered through celite. The solid was washed with 1,4-dioxane (50 mL) and the combined filtrate and washings were concentrated under reduced pressure. The residue was dissolved in DCM (30 mL) and adsorbed on silica gel (100-200 mesh (30 g) and column eluted with 5% ethyl acetate-petroleum ether. The appropriate fractions were combined and concentrated under reduced pressure to give the title compound (10.3 g, 31%) as a pale brown coloured solid: ES+ve m/z 272 (M+H)+; HPLC RT=5.0 min, 98.9% on a Zorbax CN (250 mm×4.6 mm) eluting isocratically with 20% EtOH in n-hexane, flow-rate 1 mL/min.

Intermediate 34. (S)-Methyl 3-(3-(1H-1,2,4-triazol-1-yl)phenyl)-4-((R)-3-(2-(5,6,7,8-tetrahydro-1,8-naphthyridin-2-yl)ethyl)pyrrolidin-1-yl)butanoate A solution of (3-(1H-1,2,4-triazol-1-yl)phenyl)boronic acid (Intermediate 33) (344 mg, 1.82 mmol), (R,E)-methyl 4-(3-(2-(5,6,7,8-tetrahydro-1,8-naphthyridin-2-yl)ethyl)pyrrolidin-1-yl)but-2-enoate (Intermediate 5) (200 mg, 0.607 mmol), (R)-BINAP (41.6 mg, 0.067 mmol) and bis(norbornadiene)rhodium(I) tetrafluoroborate (22.7 mg, 0.061 mmol) in 1,4-dioxane (4 mL) were added to a microwave vial and then 3.8M KOH solution (0.320 mL, 1.214 mmol) was added and the reaction mixture was heated at 95° C. for 60 min in a Biotage microwave system. The mixture was diluted with MeOH and loaded onto a SCX column (10 g). This was washed with MeOH (2CV) and then eluted using 2M $NH_3$ in MeOH. The ammoniacal fractions were evaporated under reduced pressure and the resulting orange oil (472 mg) was dissolved in 1:1 DMSO-MeOH (2.5 mL) and purified by MDAP (Method A). The appropriate fractions were evaporated under nitrogen in a blown-down unit to afford the title compound (64 mg, 22%) as a yellow oil. LCMS (System C) RT=1.15 min, 82%, ES+ve m/z 475 (M+H)+. The product (60 mg) was dissolved in EtOH (1 mL) and the main diastereoisomer was separated by preparative chiral HPLC on a Chiralpak AD-H column (250 mm×30 mm) eluting with 40% EtOH (containing 0.2% isopropylamine)-heptane (containing 0.2% isopropylamine), flow-rate=30 mL/min, detecting at 215 nm to give (S)-methyl-3-(3-(1H-1,2,4-triazol-1-yl)phenyl)-4-((R)-3-(2-(5,6,7,8-tetrahydro-1,8-naphthyridin-2-yl)ethyl)pyrrolidin-1-yl)butanoate (15 mg): Anal. Chiral HPLC RT=20.0 min, 100%, on a Chiralpak AD-H column (4.6 mm×250 mm) eluting with 40% EtOH-heptane containing 0.2% isopropylamine, flow rate=1 mL/min, detecting at 215 nm.

Intermediate 35. (E)-tert-Butyl 4-bromobut-2-enoate

Isobutylene gas (363 mL, 3.82 mol) was bubbled through a stirred solution of (E)-4-bromobut-2-enoic acid (Tetrahedron Asymmetry, 2010, 21, 1574) (210 g, 1.27 mmol) and conc. $H_2SO_4$ (20.35 mL, 382 mmol) in diethyl ether (1 L) at −40° C. for 30 min in a steal autoclave. The mixture was sealed in the autoclave and the mixture was stirred at room temperature for 24 h. The reaction was cooled to 0° C. then basified with triethylamine (250 mL) and extracted with DCM (3×200 mL). The organic layer was dried and concentrated in vacuo. The residue was triturated in n-pentane (200 mL) to give the title compound (140 g, 50%) as brown syrup: $^1$H NMR δ ($CDCl_3$, 400 MHz) 6.89 (dt, J=15, 7.5 Hz, 1H), 5.95 (dt, J=15, 1 Hz, 1H), 3.99 (dd, J=7.5, 1 Hz, 2H), 1.48 (s, 9H).

Intermediate 36. (E)-tert-Butyl 4-acetoxybut-2-enoate

A stirred solution of (E)-tert-butyl 4-bromobut-2-enoate (Intermediate 35) (280 g, 1.27 mol) in acetonitrile (1.2 L) was treated with potassium acetate (186 g, 1.9 mol) at room temperature. The mixture was stirred at 60° C. for 4 h and the reaction was monitored by TLC (10% diethyl ether in petroleum ether, $R_f$=0.4, detection by UV). The reaction mixture was cooled to room temperature, the solid was removed by filtration and washed with diethyl ether (600 mL). The filtrate was concentrated under reduced pressure, and the residue was purified by flash column chromatography on silica gel eluting with 10% diethyl ether in petroleum ether. Appropriate fractions were combined and evaporated to give the title compound (148 g, 58% yield) as a colourless liquid: $^1$H NMR δ ($CDCl_3$, 400 MHz) 6.80 (dt, J=15.5, 5 Hz, 1H), 5.93 (dt, J=15.5, 2 Hz, 1H), 4.70 (dd, 3=5, 2 Hz, 2H), 2.09 (s, 3H), 1.46 (s, 9H).

Intermediate 37. (R,E)-tert-Butyl 4-(3-(2-(5,6,7,8-tetrahydro-1,8-naphthyridin-2-yl)ethyl)pyrrolidin-1-yl)but-2-enoate

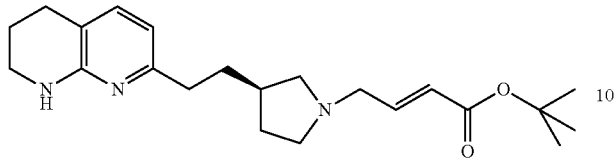

A mixture of (R)-7-(2-(pyrrolidin-3-yl)ethyl)-1,2,3,4-tetrahydro-1,8-naphthyridine (Intermediate 4) (1.305 g, 5.64 mmol), (E)-tert-butyl 4-acetoxybut-2-enoate (Intermediate 36) (1.13 g, 5.64 mmol), 1,1'-bis(diphenylphosphino)ferrocene]dichloropalladium(II) (0.207 g, 0.282 mmol) and DIPEA (2.96 mL, 16.92 mmol) in DCM (20 mL) were stirred for 3 h. The reaction mixture was partitioned between ammonium chloride solution (50 mL) and DCM (50 mL). The aqueous layer was further extracted with DCM (50 mL). The combined organic layers were passed through a hydrophobic frit and concentrated in vacuo. The crude residue was purified by chromatography (KPNH, 110 g, 0-100% TBME-cyclohexane) eluting for 60 min. Product containing fractions were combined and concentrated to give the title compound (1.65 g, 79%) as a yellow oil (E:Z ratio 7.5:1). $^1$H NMR (400 MHz, CDCl$_3$) 7.06 (d, J=7.3 Hz, 1H), 6.89 (dt, 0.7=15.6, 6.2 Hz, 1H), 6.35 (d, J=7.3 Hz, 1H), 5.90 (dt, J=15.6, 1.6 Hz, 1H), 4.66-4.80 (m, 1H), 3.38-3.44 (m, 2H), 3.20 (ddd, J=6.2, 4.8, 1.8 Hz, 2H), 2.87 (dd, J=8.4, 7.4 Hz, 1H), 2.66-2.74 (m, 3H), 2.50-2.57 (m, J=8.2, 4.0, 4.0 Hz, 2H), 2.41-2.50 (m, J=8.7, 8.7, 6.0 Hz, 1H), 1.98-2.26 (m, J=8.6 Hz, 3H), 1.87-1.96 (m, J=11.7, 6.0, 6.0 Hz, 2H), 1.74 (q, J=7.6 Hz, 2H), 1.50 (s, 9H).

Intermediate 38. (R,E)-tert-Butyl 7-(2-(1-(4-(tert-butoxy)-4-oxobut-2-en-1-yl)pyrrolidin-3-yl)ethyl)-3,4-dihydro-1,8-naphthyridine-1(2H)-carboxylate

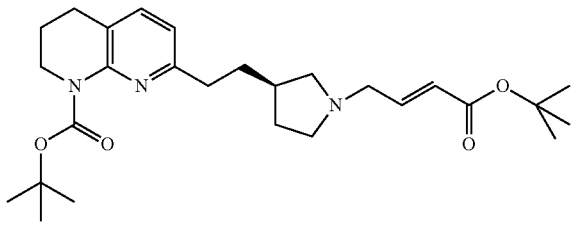 [SMILES: CC(C)(C)OC(=O)/C=C/CN1CC[C@@H](CCc2ccc3c(n2)N(C(=O)OC(C)(C)C)CCC3)C1]

A solution of (R,E)-tert-butyl 4-(3-(2-(5,6,7,8-tetrahydro-1,8-naphthyridin-2-yl)ethyl)pyrrolidin-1-yl)but-2-enoate (Intermediate 37) (1.20 g, 3.23 mmol) and di-tert-butyl dicarbonate (0.890 mL, 3.88 mmol) in THF (10 mL) at 0° C. was treated with LiHMDS solution (1.0M, 3.23 mL, 3.23 mmol) and stirred for 0.5 h. The reaction was quenched with sat. aq. ammonium chloride solution (10 mL) and extracted with DCM (2×15 mL). The combined organic layers were passed through a hydrophobic frit and concentrated in vacuo. The residue was purified by column chromatography (KPNH, 11 g) eluting with 0-25% EtOAc-cyclohexane over 40 min. The relevant fractions were combined and concentrated in vacuo to give the title compound (1.29 g, 85%) as a yellow gum: LCMS (System C) RT=1.46 min, 95%, ES+ve m/z 472 (M+H)$^+$.

Intermediate 39. tert-Butyl 7-(2-((R)-1-((S)-4-(tert-butoxy)-2-(3-(3-(hydroxymethyl)-5-methyl-1H-pyrazol-1-yl)phenyl)-4-oxobutyl)pyrrolidin-3-yl)ethyl)-3,4-dihydro-18-naphthyridine-1(2H)-carboxylate

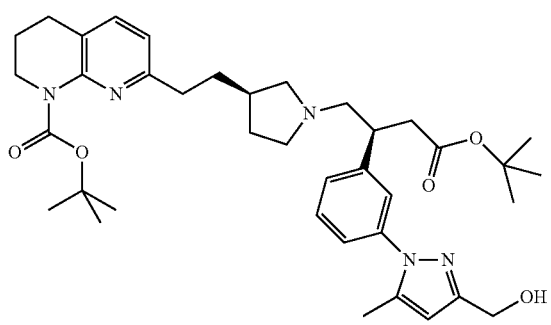 [SMILES: Cc1cc(CO)nn1-c1cccc([C@H](CC(=O)OC(C)(C)C)CN2CC[C@@H](CCc3ccc4c(n3)N(C(=O)OC(C)(C)C)CCC4)C2)c1]

A mixture of (R,E)-tert-butyl 7-(2-(1-(4-(tert-butoxy)-4-oxobut-2-en-1-yl)pyrrolidin-3-yl)ethyl)-3,4-dihydro-1,8-naphthyridine-1(2 h)-carboxylate (5.1 g, 10.8 mmol), 5-methyl-1-(3-(4,4,5,5-tetramethyl-1,3,2-dioxaborolan-2-yl)phenyl)-1H-pyrazol-3-yl)methanol (Intermediate 10) (6.21 g, 20 mmol), KOH (5.69 mL, 21.6 mmol) were dissolved in 1,4-dioxane (20 mL). The flask was purged with nitrogen for 5 min and then (R)-BINAP (0.673 g, 1.08 mmol) and [Rh(COD)Cl]$_2$ (0.267 g, 0.541 mmol) were added. The reaction was heated to 90° C. for 1 h. The solvent was removed in vacuo and the residue was partitioned between DCM and water. The organic layer was passed through a hydrophobic frit and was again concentrated in vacuo. The residue was purified by reverse-phase chromatography on C-18 column (400 g) eluting with a gradient of 50-90% (0.1% aq. NH$_3$ in MeCN)-aqueous 10 mM NH$_4$HCO$_3$, over 15CV. The relevant fractions were combined and concentrated in vacuo to give the product as a mixture of diastereoisomers (4.11 g, 58%). LCMS (System C) RT=1.45 min, 98%, ES+ve m/z 660 (M+H)$^+$. The two diastereoisomers were separated by preparative chiral HPLC on a Chiralcel OD-H column (30 mm×250 mm) eluting with 10% EtOH-heptane, flow-rate 30 mL/min, detecting at 215 nm to give the title compound (3.26 g, 46%) (major diastereoisomer): Anal. Chiral HPLC RT=16.6 min, 99.8% on a Chiralcel OD-H column (4.6 mm×250 mm) eluting with 10% EtOH-heptane, flow-rate 1 mL/min, detecting at 215 nm, and tert-butyl 7-(2-((R)-1-((R)-4-(tert-butoxy)-2-(3-(3-(hydroxymethyl)-5-methyl-1H-pyrazol-1-yl)phenyl)-4-oxobutyl)pyrrolidin-3-yl)ethyl)-3,4-dihydro-1,8-naphthyridine-1(2H)-carboxylate (minor diastereoisomer) (260 mg, 4%): Anal. Chiral HPLC RT=12.4 min, 100%.

PREPARATION OF EXAMPLES

Example 1. (S)-3-(3-(3-methyl-1H-pyrazol-5-yl)phenyl)-4-((R)-3-(2-(5,6,7,8-tetrahydro-1,8-naphthyridi-2-yl)ethyl)Pyrrolidin-1-yl)butanoic acid

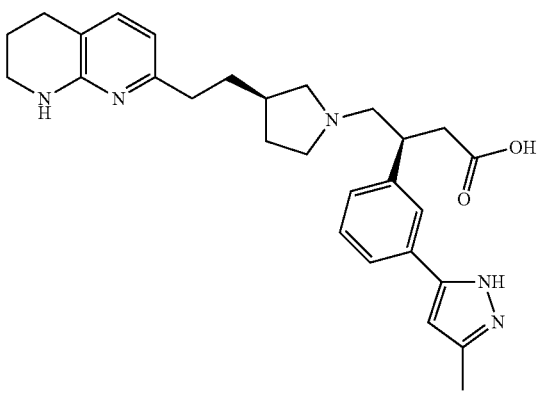 [SMILES: Cc1cc(-c2cccc([C@H](CC(=O)O)CN3CC[C@@H](CCc4ccc5c(n4)NCCC5)C3)c2)[nH]n1]

A mixture of 3-methyl-5-(4,4,5,5-tetramethyl-1,3,2-dioxaborolan-2-yl)-1H-pyrazole (available from CombiPhos) (43 mg, 0.21 mmol), (5)-methyl-3-(3-(bromophenyl)-4-((R)-3-(2-(5,6,7,8-tetrahydro-1,8-naphthyridin-2-yl)ethyl)pyrrolidin-1-yl)butanoate (Intermediate 6) (50 mg, 0.10 mmol), tripotassium phosphate (65.5 mg, 0.31 mmol), chloro(di-norbonylphosphino)(2'-dimethylamino-1,1'-biphenyl-2-yl)palladium (II) (6 mg, 0.01 mmol) was taken up in ethanol (0.5 ml) and water (0.2 ml) and heated at 130° C. for 30 min in a microwave reactor (Anton Paar, 600 W). The cooled reaction mixture was purified by MDAP (Method A) to give the title compound (17.7 mg, 33%): LCMS (System B) RT=0.52 min, ES+ve m/z 474 (M+H)$^+$; $^1$H NMR (400 MHz, DMSO-d$_6$) includes 7.61 (s, 1H), 7.56 (br d, J=7.5 Hz, 1H), 7.29 (t, J=7.5 Hz, 1H), 7.14 (br d, J=7.5 Hz, 1H), 7.01 (d, J=7.5 Hz, 1H), 6.44 (s, 1H), 6.32 (br s, 1H), 6.25 (d, J=7.5 Hz, 1H), 3.19-3.26 (m, 3H), 2.88-2.93 (m, 1H), 2.78-2.85 (m, 2H), 2.70-2.76 (m, 1H), 2.51-2.62 (m, 4H), 2.33-2.46 (m, 4H), 2.24 (s, 3H), 1.98-2.07 (m, 1H), 1.88-1.95 (m, 1H), 1.74 (quin, J=6.0 Hz, 2H), 1.55-1.67 (m, 2H), 1.31-1.39 (m, 1H).

Example 2. (S)-3-(3-(1,4-dimethyl-1H-pyrazol-5-yl)phenyl)-4-((R)-3-(2-(5, 6, 7, 8-tetrahydro-1,8-naphthyridin-2-yl) ethyl) pyrrolidin-1-yl) butanoic acid

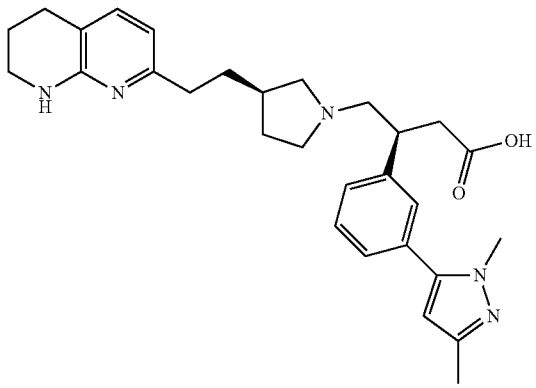 [SMILES: Cc1cc(-c2cccc([C@H](CC(=O)O)CN3CC[C@@H](CCc4ccc5c(n4)NCCC5)C3)c2)n(C)n1]

Was prepared from (S)-methyl 3-(3-bromophenyl)-4-((R)-3-(2-(5, 6, 7, 8-tetrahydro-1, 8-naphthyridin-2-yl)ethyl)pyrrolidin-1-yl)butanoate (Intermediate 6) (98.4 mg, 0.202 mmol) and 1,4-dimethyl-5-(4,4,5,5-tetramethyl-1,3,2-dioxaborolan-2-yl)-1H-pyrazole (available from CombiPhos) (0.192 mL, 0.809 mmol) in a similar way to the preparation of Example 1 to give the title compound (13.3 mg, 13%): LCMS (system A) RT=0.80 min, 97%, ES+ve m/z 488 (M+H)$^+$; $^1$H NMR (400 MHz, DMSO-d$_6$) includes 7.50 (t, J=7.5 Hz, 1H), 7.43 (br d, J=7.5 Hz, 1H), 7.39 (br s, 1H), 7.34 (s, 1H), 7.32 (br d, J=7.5 Hz, 1H), 7.20 (br d, J=7.0 Hz, 1H), 6.36 (br d, J=7.0 Hz, 1H), 3.71 (s, 3H), 2.83 (dd, J=16.5, 6.0 Hz, 1H), 2.62-2.66 (m, 2H), 2.59 (dd, J=16.5, 7.5 Hz, 1H), 2.15-2.24 (m, 1H), 2.02-2.10 (m, 1H), 1.98 (s, 3H), 1.74-1.80 (m, 2H), 1.63-1.70 (m, 2H), 1.49-1.59 (m, 1H).

Example 3. (S)-3-(3-(4H-1,2,4-triazol-4-yl)phenyl)-4-((R)-3-(2-(5,6,7,8-tetrahydro-1,8-naphthyridin-2-yl)ethyl)pyrrolidin-1-yl)butanoic acid

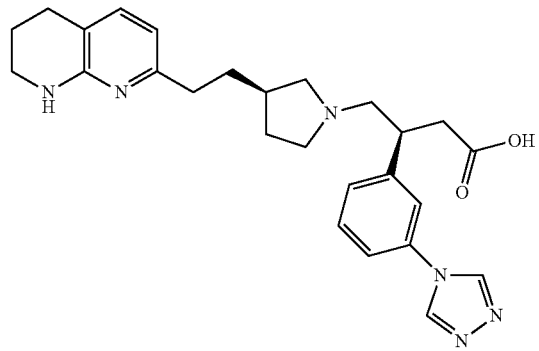 [SMILES: O=C(O)C[C@H](CN1CC[C@@H](CCc2ccc3c(n2)NCCC3)C1)c1cccc(-n2cnnc2)c1]

To a degassed mixture of (R, E)-methyl 4-(3-(2-(5, 6, 7, 8-tetrahydro-1, 8-naphthyridin-2-yl) ethyl) pyrrolidin-1-yl) but-2-enoate (Intermediate 6) (170 mg, 0.516 mmol), 4-(3-(4,4,5,5-tetramethyl-1,3,2-dioxaborolan-2-yl)phenyl)-1H-1,2,4-triazole (Intermediate 19) (420 mg, 1.55 mmol), (R)-BINAP (32.1 mg, 0.052 mmol) and aqueous KOH (3.8M, 0.407 mL) in 1,4-dioxane (24 mL), chloro(1,5-cyclooctadiene)rhodium(I) dimer (12.72 mg, 0.026 mmol) were added. The reaction mixture was heated to 100° C. for 2 h and then applied to a SCX cartridge (50 g) washed with MeOH (2CV) and then eluted with 2M ammonia in MeOH (4CV). The basic fractions were concentrated and the residue was purified by column chromatography (20 g) eluting with a gradient of 0-100% EtOAc-cyclohexane. The appropriate fractions were concentrated under reduced pressure and the residue (66.8 mg) was dissolved in MeCN (4 mL) and treated with aqueous NaOH (2M, 1.0 mL) and heated in a microwave reactor at 80° C. for 2 h. The reaction mixture was neutralised using aqueous solution of 2M HCl and concentrated in vacuo. The residue was applied to a SCX cartridge (10 g), washed with MeOH (1 CV), and eluted with 2M ammonia in methanol (2CV). The basic fractions were concentrated in vacuo to give the two diastereoisomers of the title compound (80 mg). The isomers were separated by preparative chiral HPLC on a Chiralpak ID column (30 mm×25 cm) eluting with 50% EtOH (containing 0.2% isopropylamine)-heptane, flow-rate 30 mL/min, detecting at 215 nm to give after evaporation of the appropriate fractions the title compound: (40 mg, 16%) as a gum: LCMS (System D) RT=0.34 min, 98%, ES+ve m/z 461 (M+H)$^+$; $^1$H NMR (500 MHz, CDCl₃) includes 8.48 (s, 2H), 7.45 (t, J=7.5 Hz, 1H), 7.34 (d, J=7.5 Hz, 1H), 7.27 (s, 1H), 7.20 (d, J=7.5 Hz, 1H), 7.17 (d, J=7.0 Hz, 1H), 6.27 (br d, J=7.0 Hz, 1H), 3.60-3.67 (m, 1H), 3.52-3.60 (m, 1H), 3.38-3.45 (m, 2H), 2.87-2.98 (m, 2H), 2.75-2.84 (m, 1H), 2.38-2.48 (m, 2H), 2.22-2.33 (m, 1H), 1.46-1.58 (m, 1H), 1.34-1.45 (m, 1H); Analytical chiral HPLC RT=13.5 min, on a Chiralpak ID column (4.6 mm id×25 cm) eluting with 50% EtOH (containing 0.2% isopropylamine)-heptane, flow-rate 1.0 mL/min, detecting at 215 nm.

Examples 4-9

The following examples were prepared in array format by the following generic method.

A solution of (R, E)-methyl 4-(3-(2-(5, 6, 7, 8-tetrahydro-1, 8-naphthyridin-2-yl) ethyl) pyrrolidin-1-yl) but-2-enoate (100 mg, 0.304 mmol) in 1, 4-dioxane (1 mL) and the appropriate boronate ester (0.607 mmol) selected from: 3,5-dimethyl-1-(3-(4,4,5,5-tetramethyl-1,3,2-dioxaborolan-2-yl)phenyl)-1H-1,2,4-triazole (Intermediate 12), 3-methyl-4-(3-(4,4,5,5-tetramethyl-1,3,2-dioxaborolan-2-yl)phenyl)-4H-1,2,4-triazole (Intermediate 14), 2-(5-methyl-1-(3-(4,4,5,5-tetramethyl-1,3,2-dioxaborolan-2-yl)phenyl)-1H-pyrazol-3-yl)propan-2-ol (Intermediate 16), 1-(3-(4,4,5,5-tetra methyl-1,3,2-dioxaborolan-2-yl)phenyl)-3-(trifluoromethyl)-1H-pyrazole (Intermediate 18), 1-(3-(4,4,5,5-tetramethyl-1,3,2-dioxaborolan-2-yl)phenyl)-1H-1,2,3-triazole (Intermediate 21) and 1-(3-(4,4, 5,5-tetramethyl-1,3,2-dioxaborolan-2-yl)phenyl)-1H-imidazole (Intermediate 8) was treated with (R)-BINAP (9.45 mg, 0.015 mmol), chloro(1,5-cyclooctadiene)rhodium(I) dimer (14.97 mg, 0.030 mmol) and aqueous potassium hydroxide (0.160 mL, 0.608 mmol), the mixture was heated to 80° C. for 5 h, and then stood at room temperature for 18 h. The mixture was filtered to remove any insoluble material, diluted with DMF (1 ml), and purified by MDAP (Method A). The solvent was removed under a stream of nitrogen in a plate blowdown apparatus to give the products as diastereoisomeric mixtures. The diastereoisomers were separated by preparative chiral HPLC on a Chiralcel OJ-H column (30 mm×250 mm) eluting with 20% EtOH (containing 0.2% isopropylamine)-heptane, flow rate 30 mL/min, detecting at 215 nm to give:

Example 4. 3-(3-(3,5-dimethyl-1H-1,2,4-triazol-1-yl)phenyl)-4-((R)-3-(2-(5,6,7,8-tetrahydro-1,8-naphthyridin-2-yl)ethyl)pyrrolidin-1-yl)butanoic acid

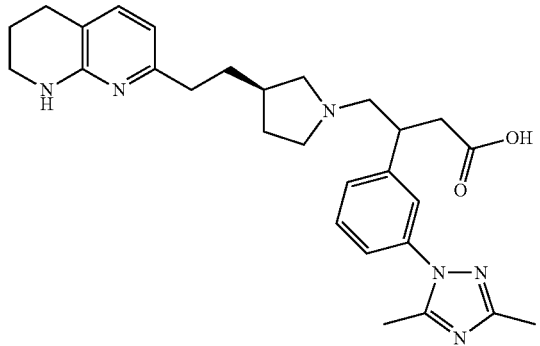 [SMILES: Cc1nc(C)n(-c2cccc(C(CC(=O)O)CN3CC[C@@H](CCc4ccc5c(n4)NCCC5)C3)c2)n1]

Isomer 1 (S)-3-(3-(3,5-dimethyl-1H-1,2,4-triazol-1-yl)phenyl-4-((R)-3-(2-(5,6,78-tetrahydro-1,8-naphthyridin-2-yl)ethyl)pyrrolidin-1-yl)butanoic acid (20 mg, 62%): LCMS (System C) RT=0.75 min, ES+ve m/z 489 (M+H)⁺; Analytical chiral HPLC on a Chiralcel OJ-H column (4.6 mm id×25 cm) eluting with 20% EtOH (containing 0.2% isopropylamine)-heptane, flow rate 1 mL/min, detecting at 215 nm: RT=22.7 min, 99.5%;
¹H NMR δ (500 MHz, DMSO-d₆) includes 7.42-7.47 (m, 1H), 7.41 (s, 1H), 7.31-7.38 (m, 2H), 7.01 (d, J=7.0 Hz, 1H), 6.21-6.28 (m, 2H), 3.19-3.25 (m, 2H), 2.40 (s, 3H), 2.26 (s, 3H), 1.94-2.05 (m, 1H), 1.83-1.93 (m, 1H), 1.69-1.78 (m, 2H), 1.53-1.65 (m, 2H), 1.28-1.38 (m, 1H).

Isomer 2 (R)-3-(3-(3,5-dimethyl-1H-1,2,4-triazol-1-yl)phenyl)-4-((R)-3-(2-(5,6,7,8-tetrahydro-1,8-naphthyridin-2-yl)ethyl)pyrrolidin-1-yl)butanoic acid (10 mg, 31%): Analytical chiral HPLC on a Chiralcel OJ-H column (4.6 mm id×25 cm) 20% EtOH (containing 0.2% isopropylamine)-heptane, flow rate 1 mL/min, detecting at 215 nm RT=13.1 min, 99.5%.

Example 5. (S)-3-(3-(3-methyl-4H-1,2,4-triazol-4-yl)phenyl)-4-((R)-3-(2-(5,6,7,8-tetrahydro-1,8-naphthyridin-2-yl)ethyl)pyrrolidin-1-yl)butanoic acid

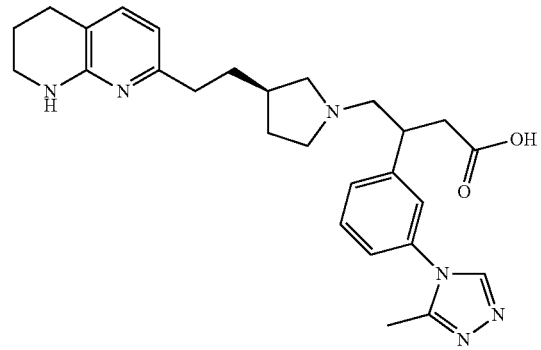 [SMILES: Cc1nncn1-c1cccc(C(CC(=O)O)CN2CC[C@@H](CCc3ccc4c(n3)NCCC4)C2)c1]

Isomer 1
(S)-3-(3-(3-methyl-4H-1,2,4-triazol-4-yl)phenyl)-4-((R)-3-(2-(5,6,7, 8-tetrahydro-1,8-naphthyridin-2-yl)ethyl)pyrrolidin-1-yl)butanoic acid (9 mg): LCMS (System C) RT=0.77 min, ES+ve m/z 475 (M+H)⁺; Analytical chiral HPLC on a Chiralcel OJ-H column (4.6 mm id×25 cm) 20% EtOH (containing 0.2% isopropylamine)-heptane, flow rate 1 mL/min, detecting at 215 nm: RT=18.1 min, 99.4%; ¹H NMR (500 MHz, DMSO) includes 9.12 (s, 1H), 7.69 (s, 1H), 7.63 (br d, J=7.5 Hz, 1H), 7.43 (t, J=7.5 Hz, 1H), 7.25 (br d, J=7.5 Hz, 1H), 7.00 (br d, J=7.0 Hz, 1H), 6.21-6.28 (m, 2H), 3.19-3.25 (m, 2H), 2.36 (s, 3H), 1.95-2.06 (m, 1H), 1.83-1.94 (m, 1H), 1.69-1.78 (m, 2H), 1.53-1.66 (m, 2H), 1.28-1.38 (m, 1H).
Isomer 2
(R)-3-(3-(3-methyl-4H-1,2,4-triazol-4-yl)phenyl)-4-((R)-3-(2-(5,6,7,8-tetrahydro-1,8-naphthyridin-2-yl)ethyl)pyrrolidin-1-yl)butanoic acid_(4 mg): Analytical chiral HPLC on a Chiralcel OJ-H column (4.6 mm id×25 cm) 20% EtOH (containing 0.2% isopropylamine)-heptane, flow rate 1 mL/min, detecting at 215 nm RT=14.0 min, 99.4%.

Example 6. (S)-3-(3-(3-(2-hydroxypropan-2-yl)-5-methyl-1H-pyrazol-1-yl)phenyl)-4-((R)-3-(2-(5,6,7,8-tetrahydro-1,8-naphthyridin-2-yl) ethyl)pyrrolidin-1-yl) butanoic acid

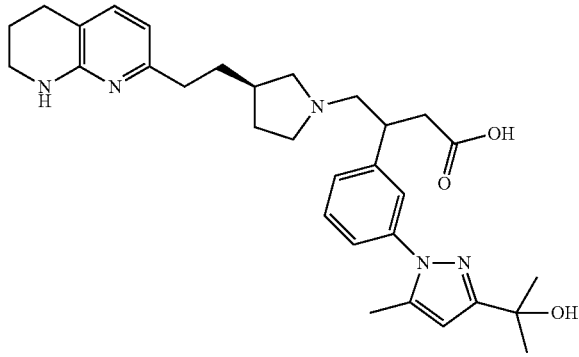 [SMILES: Cc1cc(C(C)(C)O)nn1-c1cccc(C(CC(=O)O)CN2CC[C@@H](CCc3ccc4c(n3)NCCC4)C2)c1]

Isomer 1

(S)-3-(3-(3-(2-hydroxypropan-2-yl)-5-methyl-1H-pyrazol-1-yl)phenyl)-4-((R)-3-(2-(5,6,7,8-tetrahydro-1,8-naphthyridin-2-yl)ethyl)pyrrolidin-1-yl)butanoic acid_(6 mg): LCMS (System D) RT=0.82 min, ES+ve m/z 532 (M+H)$^+$; $^1$H NMR (500 MHz, DMSO) includes 7.36-7.42 (m, 1H), 7.29 (br d, J=7.5 Hz, 1H), 7.25 (br d, J=7.5 Hz, 1H), 7.00 (br d, J=7.0 Hz, 1H), 4.86 (br s, 1H), 2.28 (s, 3H), 1.94-2.06 (m, 1H), 1.83-1.94 (m, 1H), 1.69-1.79 (m, 2H), 1.53-1.66 (m, 2H), 1.43 (s, 6H), 1.28-1.36 (m, 1H); Analytical chiral HPLC on a Chiralcel OJ-H column (4.6 mm id×25 cm) 20% EtOH (containing 0.2% isopropylamine)-heptane, flow rate 1 mL/min, detecting at 215 nm RT=22.5 min, 99.5%.

Isomer 2

(R)-3-(3-(3-(2-hydroxypropan-2-yl)-5-methyl-1H-pyrazol-1-yl)phenyl)-4-((R)-3-(2-(5,6,7,8-tetrahydro-1,8-naphthyridin-2-yl)ethyl)pyrrolidin-1-yl)butanoic acid_(4 mg): Analytical chiral HPLC RT=11.5 min, 99.5%.

Example 7. 4-((R)-3-(2-(5, 6, 7, 8-tetrahydro-1, 8-naphthyridin-2-yl) ethyl)pyrrolidin-1-yl)-3-(3-(3-(trifluoromethyl)-1H-pyrazol-1-yl) phenyl) butanoic acid

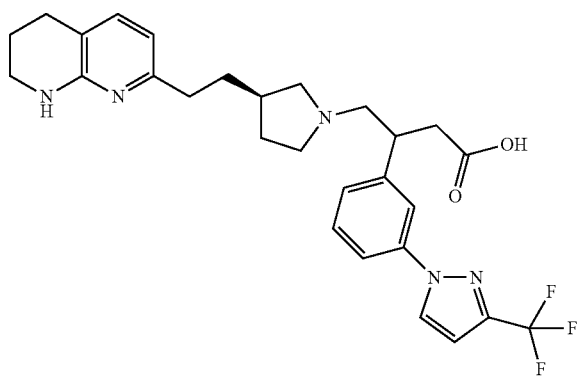 [SMILES: O=C(O)CC(CN1CC[C@@H](CCc2ccc3c(n2)NCCC3)C1)c1cccc(-n2ccc(C(F)(F)F)n2)c1]

Isomer 1

(25 mg): LCMS (System C) RT=1.01 min, ES+ve m/z 528 (M+H)$^+$; $^1$H NMR (500 MHz, DMSO-d$_6$) includes 8.72 (br s, 1H), 7.75 (br s, 1H), 7.70 (d, J=7.5 Hz, 1H), 7.45 (t, J=7.5 Hz, 1H), 7.30 (d, J=7.5 Hz, 1H), 7.03 (br s, 1H), 7.00 (d, J=7.0 Hz, 1H), 6.26 (br s, 1H), 6.23 (d, J=7.0 Hz, 1H), 1.95-2.05 (m, 1H), 1.83-1.94 (m, 1H), 1.69-1.78 (m, 2H), 1.53-1.67 (m, 2H), 1.28-1.38 (m, 1H); Analytical chiral HPLC on a Chiralcel OJ-H column (4.6 mm id×25 cm) 25% EtOH (containing 0.2% isopropylamine)-heptane, flow rate 1 mL/min, detecting at 215 nm RT=14.0 min, 99.5%.

Isomer 2

(23 mg): Analytical chiral HPLC RT=8.5 min, 99.3%

Example 8. (S)-3-(3-(1H-1,2,3-triazol-1-yl)phenyl)-4-((R)-3-(2-(5,6,7,8-tetrahydro-1,8-naphthyridin-2-yl)ethyl)pyrrolidin-1-yl)butanoic acid

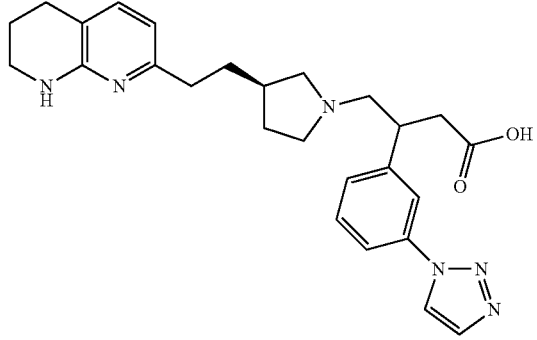 [SMILES: O=C(O)CC(CN1CC[C@@H](CCc2ccc3c(n2)NCCC3)C1)c1cccc(-n2ccnc2)c1]

Isomer 1

(S)-3-(3-(1H-1,2,3-triazol-1-yl)phenyl)-4-((R)-3-(2-(5,6,7,8-tetrahydro-1,8-naphthyridin-2-yl)ethyl)pyrrolidin-1-yl) butanoic acid_(16 mg): LCMS (System C) RT=0.76 min, ES+ve m/z 461 (M+H)$^+$; $^1$H NMR (DMSO-d$_6$) 8.81 (s, 1H), 7.96 (s, 1H), 7.79 (br s, 1H), 7.73 (br d, J=7.5 Hz, 1H), 7.50 (br t, J=7.5 Hz, 1H), 7.36 (br d, J=7.5 Hz, 1H), 7.00 (br d, J=7.0 Hz, 1H), 6.20-6.28 (m, 2H), 3.22 (br s, 2H), 2.39 (br t, J=7.5 Hz, 2H), 2.23-2.32 (m, 1H), 1.95-2.06 (m, 1H), 1.83-1.94 (m, 1H), 1.68-1.78 (m, 2H), 1.53-1.66 (m, 2H), 1.27-1.38 (m, 1H); Analytical chiral HPLC on a Chiralcel AD-H column (4.6 mm id×25 cm) 20% EtOH (containing 0.2% isopropylamine)-heptane, flow rate 1 mL/min, detecting at 215 nm RT=19.5 min, 98.8%.

Isomer 2

(R)-3-(3-(1H-1,2,3-triazol-1-yl)phenyl)-4-((R)-3-(2-(5,6,7,8-tetrahydro-1,8-naphthyridin-2-yl)ethyl)pyrrolidin-1-yl) butanoic acid_(5 mg): Analytical chiral HPLC RT=16.0 min, 99.5%

Example 9. 3-(3-(1H-imidazol-1-yl) phenyl)-4-((R)-3-(2-(5, 6, 7, 8-tetrahydro-1, 8-naphthyridin-2-yl) ethyl)pyrrolidin-1-yl) butanoic acid

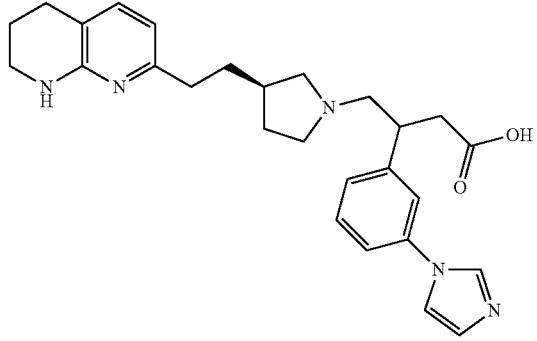

Example 9 was isolated as a mixture of diastereoisomers (2.6 mg): LCMS (System C) RT=0.76 min, 100%, ES+ve m/z 460 (M+H)+; $^1$H NMR (500 MHz, DMSO-$d_6$) includes 8.25 (br s, 1H), 7.74 (br s, 1H), 6.94-7.68 (m, 6H+), 6.15-6.40 (m, 1H+), 3.25-3.33 (m, 1H), 3.22 (br s, 2H), 2.34-2.42 (m, 2H), 2.12-2.28 (m, 1H), 1.95-2.04 (m, 1H), 1.82-1.93 (m, 1H), 1.69-1.78 (m, 2H), 1.54-1.65 (m, 2H), 1.27-1.38 (m, 1H) (spectrum shows a mixture of diastereoisomers, which are grouped together with some variation in integral values).

Example 10. 3-(3-(3-(hydroxymethyl)-5-methyl-1H-pyrazol-1-yl)phenyl)-4-((R)-3-(2-(5,6,7,8-tetrahydro-1,8-naphthyridin-2-yl)ethyl)pyrrolidin-1-yl) butanoic acid 9:1 mixture of Isomer 1:Isomer 2

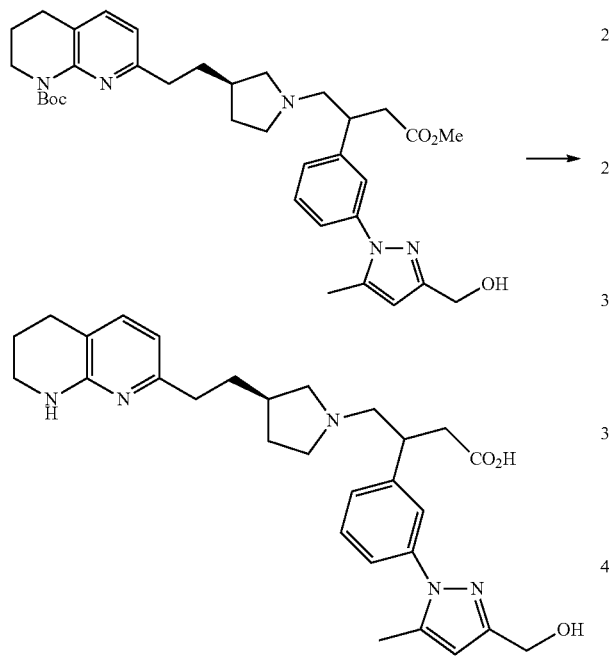

A solution of tert-butyl 7-(2-((3R)-1-(2-(3-(3-(hydroxymethyl)-5-methyl-1H-pyrazol-1-yl)phenyl)-4-methoxy-4-oxobutyl)pyrrolidin-3-yl)ethyl)-3,4-dihydro-1,8-naphthyridine-1(2H)-carboxylate (Intermediate 23) (20 mg, 0.032 mmol) in TFA (0.5 mL, 6.49 mmol) was allowed to stir for 2 h. The solution was evaporated under a stream of nitrogen and the residue was dissolved in methanol (0.5 mL) and treated with NaOH (0.5 mL, 1.0 mmol) and stirred for 15 h. The mixture was evaporated under a stream of nitrogen to remove methanol and was acidified with 2N HCl (0.7 mL). The solution was freeze-dried and the residual solid was treated with 1:1 DMSO-MeOH (1 mL). The suspension was filtered and the solution was purified by MDAP (Method A) to give, after freeze-drying, the title compound (9.5 mg, 58%) as a 9:1 mixture of diastereoisomers by NMR: LCMS (System C) RT=0.77 min, ES+ve m/z 504 (M+H)+; $^1$H NMR (CD$_3$OD) includes 7.51 (t, J=7.5 Hz, 1H), 7.32-7.43 (m, 3H), 7.15 (d, J=7.0 Hz, 1H), 6.39 (d, J=7.0 Hz, 1H), 6.30 (s, 1H), 3.45-3.63 (m, 2H), 3.35-3.40 (m, 2H), 2.86 (dd, J=16.5, 10.0 Hz, 1H), 2.66-2.73 (m, 2H), 2.61-2.67 (m, 1H), 2.53-2.59 (m, 2H), 2.32 (s, 3H), 2.15-2.26 (m, 1H), 1.83-1.91 (m, 2H), 1.74-1.83 (m, 2H), 1.63-1.72 (m, 1H).

The diastereoisomers (62 mg) obtained from another experiment were separated by preparative chiral HPLC on Chiralcel OJ-H (30 mm×250 mm) eluting with 20% EtOH (containing 0.2% isopropylamine)-heptane (containing 0.2% isopropylamine), flow-rate 30 mL/min, detecting at 215 nm to give the title compound Isomer 1

(20 mg). LCMS (System C) RT=0.76 min, ES+ve m/z 504 (M+H)+; $^1$H NMR (500 MHz, DMSO-d) δ 7.44-7.39 (1H, m), 7.34 (1H, s), 7.31 (1H, d, J 8.0 Hz), 7.27 (1H, d, J 7.4 Hz), 7.02 (1H, d, J 7.1 Hz), 6.28-6.21 (3H, m), 4.43 (2H, s), 3.50-3.27 (3H, m), 2.91-2.75 (3H, m), 2.74-2.64 (1H, m), 2.64-2.53 (4H, m), 2.48-2.36 (3H, m), 2.35-2.23 (4H, m), 2.08-1.96 (1H, m), 1.95-1.83 (1H, m), 1.79-1.70 (2H, m), 1.66-1.55 (2H, m), 1.40-1.28 (1H, m); Analytical chiral HPLC RT=11.9 min, 99.5% on Chiralcel OJ-H (4.6 mm id×250 mm) eluting with 20% EtOH (containing 0.2% isopropylamine)-heptane, flow-rate 1 mL/min, detecting at 215 nm.

Isomer 2.

Analytical chiral HPLC RT=7 min, 99.5%.

Example 11. 3-(3-(3-(fluoromethyl)-5-methyl-1H-pyrazol-1-yl)phenyl)-4-((R)-3-(2-(5,6,7,8-tetrahydro-18-naphthyridin-2-yl)ethyl)pyrrolidin-1-yl) butanoic acid (9:1 mixture of Isomer 1:Isomer 2)

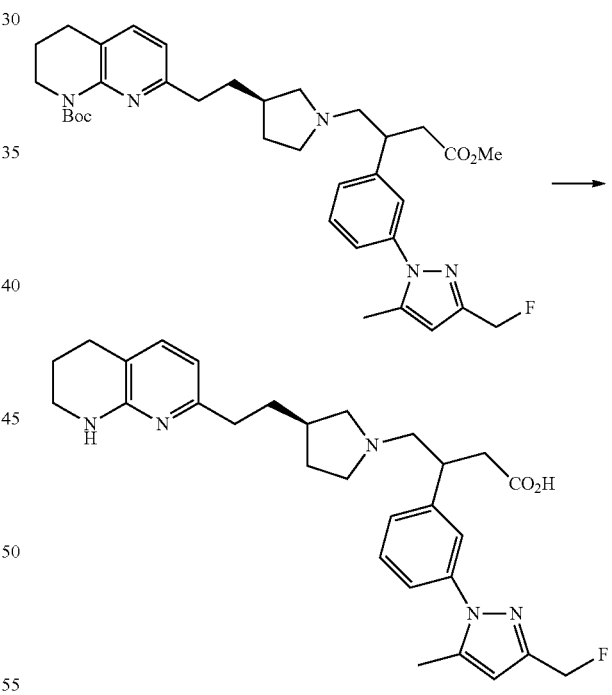

A solution of tert-butyl 7-(2-((3R)-1-(2-(3-(3-(fluoromethyl)-5-methyl-1H-pyrazol-1-yl)phenyl)-4-methoxy-4-oxobutyl)pyrrolidin-3-yl)ethyl)-3,4-dihydro-1,8-naphthyridine-1(2H)-carboxylate (Intermediate 24) (42 mg, 0.068 mmol) in TFA (0.5 mL, 6.5 mmol) was stirred at room temperature for 2 h. TFA was removed under a stream of nitrogen and the residue in methanol (0.7 mL) was treated with NaOH (1 mL, 2.0 mmol) and stirred at room temperature for 2 h. The solution was acidified with aq HCl (2N 1.3 mL) and methanol was removed under a stream of nitrogen. The aqueous solution was freeze-dried and the residue was treated with DMSO/MeOH (1:1; 1 mL), filtered and purified by MDAP (Method A) to give the title compound (20 mg, 59%): LCMS (System C) RT=0.89 min, ES+ve m/z 506 (M+H)$^+$; $^1$H NMR (400 MHz, CD$_3$OD) includes 7.49-7.56 (m, 1H), 7.35-7.45 (m, 3H), 7.14 (d, J=7.5 Hz, 1H), 6.36-6.42 (m, 2H), 5.33 (d, J=48.5 Hz, 2H), 2.86 (br dd, J=16.0, 10.0 Hz, 1H), 2.56 (t, J=7.5 Hz, 2H), 2.34 (s, 3H), 1.82-1.91 (m, 2H), 1.74-1.83 (m, 2H), 1.61-1.71 (m, 1H) (the peaks listed are associated with the major isomer).

[18F]3-(3-(3-(fluoromethyl)-5-methyl-1H pyrazol-1-yl) phenyl)-4-((R)-3-(2-(5,6,7,8-tetrahydro-1,8-naphthyridin-2-yl)ethyl)pyrrolidin-1-yl)butanoic acid maybe similarly prepared for use as a positron emission tomography (PET) ligand for diagnostic purposes.

Alternative Preparation of Example 11

(S)-3-(3-(3-(fluoromethyl)-5-methyl-1H-pyrazol-1-yl) phenyl)-4-((R)-3-(2-(5, 6, 7, 8-tetrahydro-1, 8-naphthyridin-2-yl) ethyl) pyrrolidin-1-yl) butanoic acid

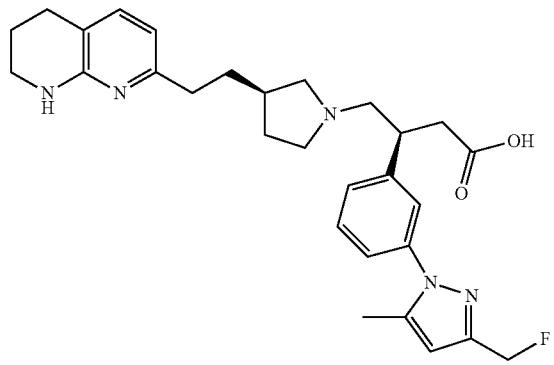 [SMILES: Cc1cc(CF)nn1-c1cccc([C@H](CC(=O)O)CN2CC[C@@H](CCc3ccc4c(n3)NCCC4)C2)c1]

To a solution of tert-butyl 7-(2-((R)-1-((S)-4-(tert-butoxy)-2-(3-(3-(hydroxymethyl)-5-methyl-1H-pyrazol-1-yl)phenyl)-4-oxobutyl)pyrrolidin-3-yl)ethyl)-3,4-dihydro-1,8-naphthyridine-1(2H)-carboxylate (Intermediate 39) (100 mg, 0.152 mmol) in acetonitrile (3 mL) at room temperature was added triethylamine (0.127 mL, 0.909 mmol) and methanesulfonyl chloride (0.059 mL, 0.758 mmol). The reaction was heated to 65° C. After 30 min LCMS indicated conversion to alkyl chloride intermediate. The reaction was partitioned between ethyl acetate and sodium bicarbonate solution. The organic layer was dried over MgSO$_4$ and concentrated in vacuo. The residual light orange coloured oil was dissolved in DMF (5.0 mL) and added potassium fluoride (35.2 mg, 0.606 mmol) and 4,7, 13,16,21,24-hexaoxa-1,10-diazabicyclo[8.8.8]hexacosane (available from Aldrich) (228 mg, 0.606 mmol), the resulting solution was heated in a microwave reactor at 120° C. for 0.5 h, LCMS indicated displacement of chloride by fluoride. The reaction mixture was partitioned between water and ethyl acetate. The organic layer was dried (MgSO$_4$) and concentrated in vacuo to give a brown oil. The crude oil was dissolved in DCM (1 mL) and treated with TFA (2 mL) and stirred for 2 h. The solution was concentrated under a stream of nitrogen to give an orange gum and purified by MDAP (Method A), the relevant fractions were collected and concentrated to give (S)-3-(3-(3-(fluoromethyl)-5-methyl-1-pyrazol-1-yl)phenyl)-4-((R)-3-(2-(5,6,7,8-tetra hydro-1,8-naphthyridin-2-yl)ethyl)pyrrolidin-1-yl)butanoic acid (39.8 mg, 52%) as a colourless gum: LCMS (System C) RT=0.97 min, 100%, ES+ve m/z 506 (M+H)$^+$.

Example 12. 3-(3-(1,4-dimethyl-1H-imidazol-2-yl)phenyl)-4-((R)-3-(2-(5,6,7,8-tetrahydro-1,8-naphthyridin-2-yl)ethyl)pyrrolidin-1-yl)butanoic acid

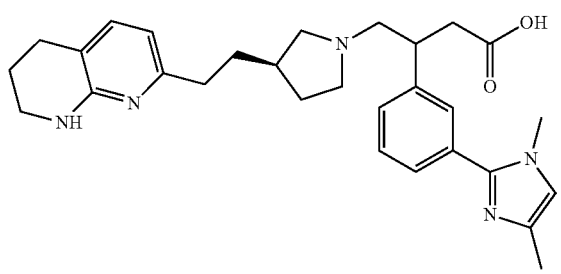 [SMILES: Cc1cn(C)c(-c2cccc(C(CC(=O)O)CN3CC[C@@H](CCc4ccc5c(n4)NCCC5)C3)c2)n1]

A degassed mixture of (R,E)-methyl 4-(3-(2-(5,6,7,8-tetrahydro-1,8-naphthyridin-2-yl)ethyl)pyrrolidin-1-yl)but-2-enoate (Intermediate 5) (100 mg, 0.304 mmol), 1,4-dimethyl-2-(3-(4,4,5,5-tetramethyl-1,3,2-dioxaborolan-2-yl)phenyl)-1H-imidazole (Intermediate 27) (272 mg, 0.911 mmol), (R)-BINAP (9.45 mg, 0.015 mmol) and aq. 3.8M KOH (0.240 mL, 0.911 mmol) in 1,4-dioxane (1 mL) was treated with chloro(1,5-cyclooctadiene)rhodium(I) dimer (14.97 mg, 0.030 mmol). The reaction mixture was heated at 100° C. for 3.5 h. An aqueous solution of KOH (0.240 mL, 0.911 mmol) was added and the mixture was heated at 100° C. for 30 min. The mixture was filtered to remove insoluble material, diluted with DMF (1 mL), and purified by MDAP (Method A). The appropriate fractions were evaporated under a stream of nitrogen in a blowdown apparatus. The residue (35 mg) was dissolved in EtOH (1 mL) and the diastereoisomers were separated by chiral HPLC on a Chiralcel OJ-H column (30 mm×250 mm) eluting with 25% EtOH (containing 0.2% isopropylamine)-heptane (containing 0.2% isopropylamine), flow rate=30 mL/min, detecting at 215 nm. After evaporation of the appropriate fractions the two isomers of the title compound were obtained:

Isomer 1

(S)-3-(3-(1,4-dimethyl-1H-imidazol-2-yl)phenyl)-4-((R)-3-(2-(5,6,7,8-tetrahydro-1,8-naphthyridin-2-yl)ethyl)pyrrolidin-1-yl)butanoic acid (16 mg): LCMS (System C) RT=0.81 min, 100%, ES+ve m/z 488 (M+H)$^+$; Analytical Chiral HPLC on Chiralcel OJ-H column (4.6 mm id×25 cm) eluting with 25% EtOH (containing 0.2% isopropylamine)-heptane (containing 0.2% isopropylamine), flow-rate 1 mL/min, detecting at 215 nm RT=13.2 min, 99.5%; $^1$H NMR (500 MHz, DMSO-d$_6$) δ 7.48 (1H, s), 7.44 (1H, d, J 7.7 Hz), 7.35 (1H, t, J 7.6 Hz), 7.26 (1H, d, J 7.7 Hz), 7.01 (1H, d, J 6.6 Hz), 6.92 (1H, s), 6.32-6.21 (2H, m), 3.30-3.21 (4H, m), 3.18 (3H, s), 2.85-2.76 (2H, m), 2.75-2.63 (2H, m), 2.63-2.54 (3H, m), 2.46-2.30 (3H, m), 2.23 (1H, t, J 8.0 Hz), 2.12 (3H, s), 2.04-1.92 (1H, m), 1.92-1.82 (1H, m), 1.79-1.69 (2H, m), 1.67-1.53 (2H, m), 1.37-1.27 (1H, m).

Isomer 2

(R)-3-(3-(1,4-dimethyl-1H-imidazol-2-yl)phenyl)-4-((R)-3-(2-(5,6,7,8-tetrahydro-1,8-naphthyridin-2-yl)ethyl)pyrrolidin-1-yl)butanoic acid (6 mg): Analytical chiral HPLC RT=7.6 min, 99.3%.

Example 13. (S)-3-(3-(2,4-dimethyl-1H-imidazol-5-yl)phenyl)-4-((R)-3-(2-(5,6,7,8-tetrahydro-1,8-naphthyridin-2-yl)ethyl)pyrrolidin-1-yl)butanoic acid sodium salt

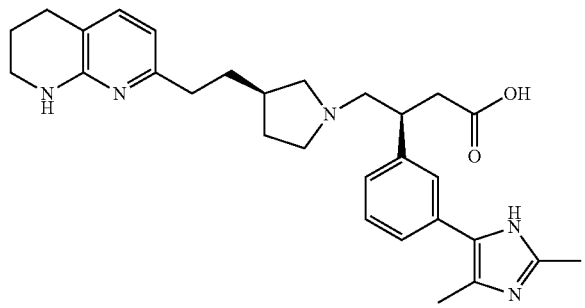 [SMILES: Cc1nc(C)c(-c2cccc([C@H](CC(=O)O)CN3CC[C@@H](CCc4ccc5c(n4)NCCC5)C3)c2)[nH]1]

NaOH (2M in MeOH) (108 μL, 0.215 mmol) was added to a stirring solution of methyl 3-(3-(2,4-dimethyl-1H-imidazol-5-yl)phenyl)-4-((R)-3-(2-(5,6,7,8-tetrahydro-1,8-naphthyridin-2-yl)ethyl)pyrrolidin-1-yl)butanoate (Intermediate 32 Isomer 2) (18 mg, 0.036 mmol) in methanol (40 μL) and DCM (320 μL). The solution was allowed to stir at room temperature in a stoppered flask overnight. The solvent was blown down under nitrogen to give an off-white solid (47 mg). The sample was dissolved in 1:1 DMSO:MeOH and purified by MDAP (Method A). The solvent was removed from the appropriate fractions to afford the title compound (8.49 mg, 49%) as a colourless gum: LCMS (System C) RT=0.77 min, 99%, ES+ve m/z 488 (M+H)$^+$. $^1$H NMR (DMSO-$d_6$, 400 MHz) 7.47-7.30 (m, 2H), 7.30-7.23 (m, 1H), 7.01 (d, J=7.3 Hz, 1H), 6.25 (d, J=7.3 Hz, 1H), 3.25-3.20 (m, 3H), 2.90-2.67 (m, 4H), 2.60 (t, J=6 Hz, 2H), 2.55-2.52 (m, 2H), 2.45-2.37 (m, 3H), 2.35-2.27 (m, 3H), 2.26 (s, 3H), 2.08-1.99 (m, 1H), 1.96-1.86 (m, 1H), 1.77-1.70 (m, 2H), 1.65-1.57 (m, 2H), 1.39-1.29 (m, 1H).

Example 14, (S)-3-(3-(1H-1,2,4-triazol-1-yl)phenyl)-4-((R)-3-(2-(5,6,7,8-tetrahydro-1,8-naphthyridin-2-yl)ethyl)pyrrolidin-1-yl)butanoic acid sodium salt

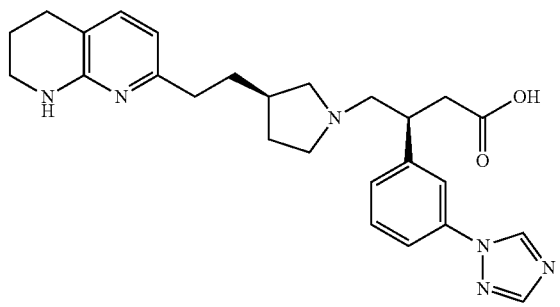 [SMILES: O=C(O)C[C@H](CN1CC[C@@H](CCc2ccc3c(n2)NCCC3)C1)c1cccc(-n2cncn2)c1]

NaOH (2M in MeOH) (31.6 μL, 0.063 mmol) was added to a stirring solution of (S)-methyl 3-(3-(1H-1,2,4-triazol-1-yl)phenyl)-4-((R)-3-(2-(5,6,7,8-tetrahydro-1,8-naphthyridin-2-yl)ethyl)pyrrolidin-1-yl)butanoate (15 mg, 0.032 mmol) in MeOH (60 μL) and DCM (0.32 mL). The solution was allowed to stir at room temperature in a sealed vessel for 6 h. The solvent was evaporated in a blown-down unit under nitrogen overnight. The residual white solid was dissolved in 1:1 DMSO-MeOH (0.8 mL) and purified by MDAP (Method A). The solvent was removed from the appropriate fractions to afford the title compound (12 mg, 82%) as an off-white solid. LCMS (System C) RT=0.75 min, 100%, ES+ve m/z 461 (M+H)$^+$. $^1$H NMR (DMSO-$d_6$, 400 MHz) δ 9.29 (s, 1H), 8.23 (s, 1H), 8.15 (s, 1H), 7.77 (m, 1H), 7.70 (br d, J=8.5 Hz, 1H), 7.48 (t, J=7.8 Hz, 1H), 7.32 (d, J=7.8 Hz, 1H), 7.02 (d, J=7.3 Hz, 1H), 6.32 (br, 1H), 6.25 (d, J=7.3 Hz, 1H), 3.36-3.29 (m, 1H), 3.23 (br, 3H), 2.92 (d, J=12.1 Hz, 1H), 2.86-2.81 (m, 2H), 2.75-2.69 (m, 1H), 2.65 (m, 1H), 2.60 (m, 3H), 2.47-2.45 (m, 1H, obscured by DMSO), 2.41 (t, J=7.7 Hz, 2H), 2.37-2.32 (m, 1H), 2.07-2.00 (m, 1H), 1.91 (m, 1H), 1.75 (m, 2H), 1.66-1.58 (m, 2H), 1.40-1.32 (m, 1H).

Biological Assays
Cell Adhesion Assays

Reagents and methods utilised were as described [Ludbrook et al, *Biochem. J.* 2003, 369, 311), with the following points of clarification. The following cell lines were used, with ligands in brackets: K562-$\alpha_5\beta_1$ (Fibronectin), K562-$\alpha_v\beta_3$ (LAP-$b_1$), K562-$\alpha_v\beta_5$ (Vitronectin), K562-$\alpha_v\beta_6$ (LAP-$b_1$), K562-$\alpha_v\beta_8$ (LAP-$b_1$). The divalent cation used to facilitate adhesion was 2 mM $MgCl_2$. Adhesion was quantified by cell labelling with the fluorescent dye BCECF-AM (Life Technologies), where cell suspensions at 3×10$^6$ cells/mL were incubated with 0.33 mL/mL of 30 mM BCECF-AM at 37° C. for 10 minutes, before dispensing into the assay plate. At the assay conclusion cells that adhered were lysed using 50 μL/well of 0.5% Triton X-100 in $H_2O$ to release fluorescence. Fluorescence intensity was detected using an Envision® plate reader (Perkin Elmer). For active antagonists in the assay, data were fitted to a 4 parameter logistic equation for IC$_{50}$ determinations.

The mean affinities (pIC$_{50}$) of Example 1 in the Cell Adhesion Assays were, for $\alpha_v\beta_6$ pIC$_{50}$=8.5; $\alpha_v\beta_3$ pIC$_{50}$=7.2; $\alpha_v\beta_5$ pIC$_{50}$=8.1; $\alpha_v\beta_8$ pIC$_{50}$=8.2.

The mean affinities (pIC$_{50}$) of Example 2 in the cell Adhesion Assays were, for $\alpha_v\beta_6$ pIC$_{50}$=8.0; $\alpha_v\beta_3$ pIC$_{50}$=5.8; $\alpha_v\beta_5$ pIC$_{50}$=7.2; $\alpha_v\beta_8$ pIC$_{50}$=7.9.

The mean affinities (pIC$_{50}$) of Example 3 in the cell Adhesion Assays were, for $\alpha_v\beta_6$ pIC$_{50}$=8.7; $\alpha_v\beta_3$ pIC$_{50}$=6.3; $\alpha_v\beta_5$ pIC$_{50}$=7.3; $\alpha_v\beta_8$ pIC$_{50}$=8.2; $\alpha_v\beta_1$ pIC$_{50}$=7.6.

The mean affinities (pIC$_{50}$) of Example 4 in the cell Adhesion Assays were, for $\alpha_v\beta_6$ pIC$_{50}$=8.5; $\alpha_v\beta_3$ pIC$_{50}$=5.9; $\alpha_v\beta_5$ pIC$_{50}$=6.8; $\alpha_v\beta_8$ pIC$_{50}$=7.9; $\alpha_v\beta_1$ pIC$_{50}$=7.3.

The mean affinities (pIC$_{50}$) of Example 5 in the cell Adhesion Assays were, for $\alpha_v\beta_6$ pIC$_{50}$=8.3; $\alpha_v\beta_3$ pIC$_{50}$=6.4; $\alpha_v\beta_5$ pIC$_{50}$=7.5; $\alpha_v\beta_8$ pIC$_{50}$=8.0; $\alpha_v\beta_1$ pIC$_{50}$=7.1.

The mean affinities (pIC$_{50}$) of Example 6 in the cell Adhesion Assays were, for $\alpha_v\beta_6$ pIC$_{50}$=7.9; $\alpha_v\beta_3$ pIC$_{50}$=5.4; $\alpha_v\beta_5$ pIC$_{50}$=6.7; $\alpha_v\beta_8$ pIC$_{50}$=7.3.

The mean affinities (pIC$_{50}$) of Example 7 in the cell Adhesion Assays were, for $\alpha_v\beta_6$ pIC$_{50}$=8.2; $\alpha_v\beta_3$ pIC$_{50}$=6.2; $\alpha_v\beta_5$ pIC$_{50}$=7.3; $\alpha_v\beta_8$ pIC$_{50}$=7.6.

The mean affinities (pIC$_{50}$) of Example 8 in the cell Adhesion Assays were, for $\alpha_v\beta_6$ pIC$_{50}$=8.5; $\alpha_v\beta_3$ pIC$_{50}$=6.6; $\alpha_v\beta_5$ pIC$_{50}$=7.5; $\alpha_v\beta_8$ pIC$_{50}$=8.2; $\alpha_v\beta_1$ pIC$_{50}$=7.3.

The mean affinities (pIC$_{50}$) of Example 9 in the cell Adhesion Assays were, for $\alpha_v\beta_6$ pIC$_{50}$=8.2; $\alpha_v\beta_3$ pIC$_{50}$=5.9; $\alpha_v\beta_5$ pIC$_{50}$=7.3; $\alpha_v\beta_8$ pIC$_{50}$=7.6.

The mean affinities (pIC$_{50}$) of Example 10 in the cell Adhesion Assays were, for $\alpha_v\beta_6$ pIC$_{50}$=8.6; $\alpha_v\beta_3$ pIC$_{50}$=6.2; $\alpha_v\beta_5$ pIC$_{50}$=6.8; $\alpha_v\beta_8$ pIC$_{50}$=8.0

The mean affinities (pIC$_{50}$) of Example 11 in the cell Adhesion Assays were, for $\alpha_v\beta_6$ pIC$_{50}$=8.5; $\alpha_v\beta_3$ pIC$_{50}$=5.9; $\alpha_v\beta_5$ pIC$_{50}$=6.8; $\alpha_v\beta_8$ pIC$_{50}$=7.8; $\alpha_v\beta_1$ pIC$_{50}$=7.2.

The mean affinities (pIC$_{50}$) of Example 12 in the cell Adhesion Assays were, for α$_v$β$_6$ pIC$_{50}$=8.6; α$_v$β$_3$ pIC$_{50}$=5.6; α$_v$β$_5$ pIC$_{50}$=6.7; α$_v$β$_8$ pIC$_{50}$=8.0.

The mean affinities (pIC$_{50}$) of Example 13 in the cell Adhesion Assays were, for α$_v$β$_6$ pIC$_{50}$=8.6; α$_v$β$_3$ pIC$_{50}$=6.5; α$_v$β$_5$ pIC$_{50}$=7.0; α$_v$β$_8$ pIC$_{50}$=8.0; α$_v$β$_1$ pIC$_{50}$=7.0.

The mean affinities (pIC$_{50}$) of Example 14 in the cell Adhesion Assays were, for α$_v$β$_6$ pIC$_{50}$=8.9; α$_v$β$_3$ pIC$_{50}$=6.6; α$_v$β$_5$ pIC$_{50}$=7.5; α$_v$β$_8$ pIC$_{50}$=8.2; α$_v$β$_1$ pIC$_{50}$=7.0.

The invention claimed is:

1. A compound of formula (I) or a pharmaceutically acceptable salt thereof:

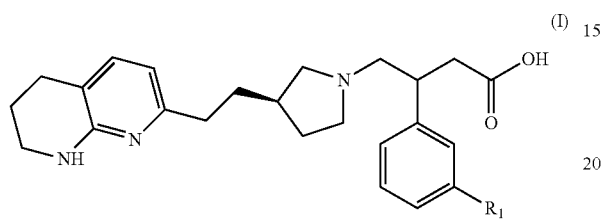

wherein
R$_1$ is an optionally substituted five-membered aromatic heterocycle, wherein the optionally substituted five-membered aromatic heterocycle is selected from an optionally substituted N- or a C-linked pyrazole, an optionally substituted N- or a C-linked triazole, and an optionally substituted N- or C-linked imidazole,
wherein the optionally substituted N- or a C-linked pyrazole, the optionally substituted N- or a C-linked triazole, and the optionally substituted N- or C-linked imidazole is optionally substituted by 1 or 2 substituents independently selected from methyl, ethyl, fluoro, hydroxymethyl, 2-hydroxypropan-2-yl, trifluoromethyl, difluoromethyl, and fluoromethyl;
wherein R$_1$ is not 3,5-dimethyl-1H-pyrazol-1-yl, 5-methyl-1H-pyrazol-1-yl, 5-ethyl-3-methyl-1H-pyrazol-1-yl, 3,5-diethyl-1H-pyrazol-1-yl, 4-fluoro-3,5-dimethyl-1H-pyrazol-1-yl, 3-methyl-1H-pyrazol-1-yl, or 1H-pyrazol-1-yl.

2. The compound according to claim 1, wherein R$_1$ is:

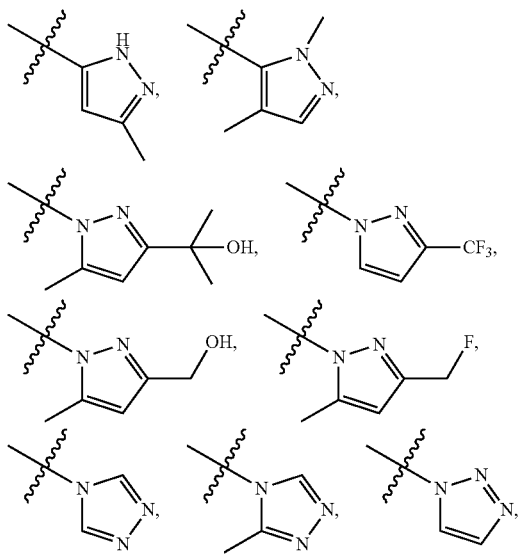

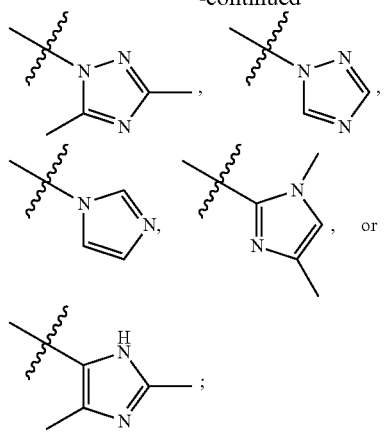

or a pharmaceutically acceptable salt thereof.

3. The compound according to claim 1, wherein R$_1$ is an optionally substituted C-linked pyrazole selected from 3-methyl-1H-pyrazol-5-yl and 1,4-dimethyl-1H-pyrazol-5-yl; or a pharmaceutically acceptable salt thereof.

4. The compound according to claim 1, wherein R$_1$ is an optionally substituted N-linked pyrazole selected from 3-(2-hydroxypropan-2-yl)-5-methyl-1H-pyrazol-1-yl, 3-(trifluoromethyl)-1H-pyrazol-1-yl, 3-(hydroxymethyl)-5-methyl-1H-pyrazol-1-yl, and 3-(fluoromethyl)-5-methyl-1H-pyrazol-1-yl; or a pharmaceutically acceptable salt thereof.

5. The compound according to claim 1, wherein R$_1$ is an optionally substituted N-linked triazole selected from 4H-1,2,4-triazol-4-yl, 3,5-dimethyl-1H-1,2,4-triazol-1-yl, 3-methyl-4H-1,2,4-triazol-4-yl, 1H-1,2,3-triazol-1-yl, and 1H-1,2,4-triazol-1-yl; or a pharmaceutically acceptable salt thereof.

6. The compound according to claim 1, wherein R$_1$ is an optionally substituted N- or C-linked imidazole selected from 1H-imidazol-1-yl, 1-methyl-1H-imidazol-2-yl, 4-methyl-1H-imidazol-2-yl, (1,4-dimethyl-1H-imidazol-2-yl), and (2,4-dimethyl-1H-imidazol-5-yl); or a pharmaceutically acceptable salt thereof.

7. A method of treating a disorder in a human, wherein the disorder is responsive to antagonism of an α$_v$β$_6$ receptor, the method comprising administering to the human in need thereof a therapeutically effective amount of the compound or pharmaceutically acceptable salt according to claim 1, wherein the disorder is a fibrotic disease or condition.

8. A method of treating a disorder in a human, wherein the disorder is responsive to antagonism of an αvβ6 receptor, the method comprising administering to the human in need thereof a therapeutically effective amount of the compound or pharmaceutically acceptable salt according to claim 2, wherein the disease is a fibrotic disease or condition.

9. A pharmaceutical composition comprising the compound or pharmaceutically acceptable salt according to claim 1, and a pharmaceutically acceptable excipient.

10. A pharmaceutical composition comprising the compound or pharmaceutically acceptable salt according to claim 2, and a pharmaceutically acceptable excipient.

11. A compound which is [18F] labelled 3-(3-(3-(fluoromethyl)-5-methyl-1H-pyrazol-1-yl)phenyl)-4-((R)-3-(2-(5,6,7,8-tetrahydro-1,8-naphthyridin-2-yl)ethyl)pyrrolidin-1-yl)butanoic acid.

12. A method of treating a disorder in a human, wherein the disorder is responsive to antagonism of an α$_v$β$_6$ receptor, the method comprising administering to the human in need thereof a therapeutically effective amount of the compound or pharmaceutically acceptable salt according to claim 1, wherein the disorder is idiopathic pulmonary fibrosis.

13. A method of treating a disorder in a human, wherein the disorder is responsive to antagonism of an αvβ6 receptor, the method comprising administering to the human in need thereof a therapeutically effective amount of the compound or pharmaceutically acceptable salt according to claim 2, wherein the disorder is idiopathic pulmonary fibrosis.

* * * * *